US012558257B2

(12) United States Patent
Christopherson et al.

(10) Patent No.: US 12,558,257 B2
(45) Date of Patent: Feb. 24, 2026

(54) SYSTEMS AND METHODS FOR TREATMENT OF OBSTRUCTIVE SLEEP APNEA

(71) Applicant: CRYOSA, INC., Shoreview, MN (US)

(72) Inventors: Mark Christopherson, Shoreview, MN (US); Orhan Soykan, Lino Lakes, MN (US); Donald A. Gonzales, Folsom, LA (US); Stefan Skorich, St. Louis Park, MN (US)

(73) Assignee: CRYOSA, INC., Shoreview, MN (US)

( * ) Notice: Subject to any disclaimer, the term of this patent is extended or adjusted under 35 U.S.C. 154(b) by 605 days.

(21) Appl. No.: 17/419,822

(22) PCT Filed: Dec. 31, 2019

(86) PCT No.: PCT/US2019/069113
§ 371 (c)(1),
(2) Date: Jun. 30, 2021

(87) PCT Pub. No.: WO2020/142519
PCT Pub. Date: Jul. 9, 2020

(65) Prior Publication Data
US 2022/0071802 A1 Mar. 10, 2022

Related U.S. Application Data

(60) Provisional application No. 62/890,884, filed on Aug. 23, 2019, provisional application No. 62/787,125, filed on Dec. 31, 2018.

(51) Int. Cl.
*A61F 7/12* (2006.01)
*A61F 7/00* (2006.01)

(52) U.S. Cl.
CPC ................ *A61F 7/12* (2013.01); *A61F 7/007* (2013.01); *A61F 7/0085* (2013.01); *A61F 7/123* (2013.01);
(Continued)

(58) Field of Classification Search
CPC ............................................. A61F 2007/0054
See application file for complete search history.

(56) References Cited

U.S. PATENT DOCUMENTS 3,674,031 A 7/1972 Weiche
3,712,306 A 1/1973 Bryne
(Continued)

FOREIGN PATENT DOCUMENTS

AU 2011279923 B2 2/2016
AU 2018226785 A1 10/2019
(Continued)

OTHER PUBLICATIONS

Avram et al., Cryolipolysis for Subcutaneous Fat Layer Reduction, Lasers in Surgery and Medicine, 41: 703-708; Dec. 2009.
(Continued)

*Primary Examiner* — Kaitlyn E Smith
(74) *Attorney, Agent, or Firm* — Perkins Coie LLP

(57) ABSTRACT
Methods, devices, and systems employ cryolysis of oropharyngeal adipose tissues to selectively remove fat cells from the tissues causing obstructive sleep apnea. In various embodiments, a chilled liquid—e.g., a liquid or air—is applied to the target tissue at a temperature and for a duration sufficient to cause cryolysis.

15 Claims, 42 Drawing Sheets

(52) U.S. Cl.
CPC . *A61F 2007/001* (2013.01); *A61F 2007/0017* (2013.01); *A61F 2007/0063* (2013.01); *A61F 2007/0069* (2013.01); *A61F 2007/0075* (2013.01); *A61F 2007/0091* (2013.01); *A61F 2007/126* (2013.01)

(56) References Cited

U.S. PATENT DOCUMENTS

| | | | |
|---|---|---|---|
| 3,889,680 A | 6/1975 | Armao |
| 5,245,023 A | 9/1993 | Peoples et al. |
| 5,250,430 A | 10/1993 | Peoples et al. |
| 5,534,432 A | 7/1996 | Peoples et al. |
| 5,663,063 A | 9/1997 | Peoples et al. |
| 5,743,904 A | 4/1998 | Edwards |
| 5,800,379 A | 9/1998 | Edwards |
| 6,017,337 A | 1/2000 | Pira |
| 6,032,675 A | 3/2000 | Rubinsky |
| 6,041,787 A | 3/2000 | Rubinsky |
| 6,045,549 A | 4/2000 | Smethers et al. |
| 6,126,657 A | 10/2000 | Edwards et al. |
| 6,245,537 B1 | 6/2001 | Williams et al. |
| 6,316,262 B1 | 11/2001 | Huisman et al. |
| 6,378,525 B1 | 4/2002 | Beyar et al. |
| 6,408,851 B1 | 6/2002 | Karell |
| 6,514,515 B1 | 2/2003 | Williams |
| 6,548,569 B1 | 4/2003 | Williams et al. |
| 6,555,123 B2 | 4/2003 | Williams et al. |
| 6,585,994 B2 | 7/2003 | Williams et al. |
| 6,592,892 B1 | 7/2003 | Williams |
| 6,593,116 B1 | 7/2003 | Huisman et al. |
| 6,610,764 B1 | 8/2003 | Martin et al. |
| 6,623,749 B2 | 9/2003 | Williams et al. |
| 6,689,589 B2 | 2/2004 | Huisman et al. |
| 6,746,447 B2 | 6/2004 | Davison et al. |
| 6,746,685 B2 | 6/2004 | Williams et al. |
| 6,770,071 B2 | 8/2004 | Wołoszko et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,878,758 B2 | 4/2005 | Martin et al. |
| D568,258 S | 5/2008 | Adam |
| 7,367,341 B2 | 5/2008 | Anderson et al. |
| 7,458,932 B2 | 12/2008 | Sun |
| 7,507,235 B2 | 3/2009 | Keogh et al. |
| 7,575,870 B1 | 8/2009 | Lalvani et al. |
| 7,713,266 B2 | 5/2010 | Elkins et al. |
| 7,842,029 B2 | 11/2010 | Anderson et al. |
| 7,850,683 B2 | 12/2010 | Elkins et al. |
| 7,854,754 B2 | 12/2010 | Ting et al. |
| 7,862,558 B2 | 1/2011 | Elkins et al. |
| 7,998,137 B2 | 8/2011 | Elkins et al. |
| 8,192,474 B2 | 6/2012 | Levinson |
| 8,275,442 B2 | 9/2012 | Allison |
| 8,285,390 B2 | 10/2012 | Levinson et al. |
| 8,287,579 B2 | 10/2012 | Nimitz |
| 8,298,216 B2 | 10/2012 | Burger et al. |
| 8,337,539 B2 | 12/2012 | Ting et al. |
| 8,409,185 B2 | 4/2013 | Burger et al. |
| 8,523,927 B2 | 9/2013 | Levinson et al. |
| 8,603,073 B2 | 12/2013 | Allison |
| 8,676,338 B2 | 3/2014 | Levinson |
| 8,702,774 B2 | 4/2014 | Baker et al. |
| 8,715,275 B2 | 5/2014 | Burger et al. |
| 8,768,468 B2 | 7/2014 | Garcia et al. |
| 8,834,547 B2 | 9/2014 | Anderson et al. |
| 8,840,608 B2 | 9/2014 | Anderson et al. |
| 9,033,966 B2 | 5/2015 | McKay |
| 9,039,688 B2 | 5/2015 | Palmer et al. |
| 9,072,498 B2 | 7/2015 | Elkins et al. |
| 9,078,634 B2 | 7/2015 | Gonzales et al. |
| 9,101,346 B2 | 8/2015 | Burger et al. |
| 9,113,855 B2 | 8/2015 | Burger et al. |
| 9,254,162 B2 | 2/2016 | Burger et al. |
| 9,295,512 B2 | 3/2016 | Allison et al. |
| 9,308,120 B2 | 4/2016 | Anderson et al. |
| 9,314,290 B2 | 4/2016 | Fourkas et al. |
| 9,345,526 B2 | 5/2016 | Elkins et al. |
| 9,402,676 B2 | 8/2016 | Babkin et al. |
| 9,408,745 B2 | 8/2016 | Levinson et al. |
| 9,439,805 B2 | 9/2016 | Gonzales et al. |
| 9,545,523 B2 | 1/2017 | Nanda |
| 9,610,112 B2 | 4/2017 | Karnik et al. |
| 9,717,546 B2 | 8/2017 | Varady |
| 9,844,461 B2 | 12/2017 | Levinson et al. |
| 9,861,421 B2 | 1/2018 | O'Neil et al. |
| 9,907,693 B2 | 3/2018 | Burger et al. |
| 9,980,765 B2 | 5/2018 | Avram et al. |
| 10,085,881 B2 | 10/2018 | Karnik et al. |
| 10,092,346 B2 | 10/2018 | Levinson et al. |
| 10,111,774 B2 | 10/2018 | Gonzales et al. |
| 10,201,380 B2 | 2/2019 | DeBenedictis et al. |
| 10,213,244 B2 | 2/2019 | Fourkas et al. |
| 10,363,080 B2 | 7/2019 | Elkins et al. |
| 10,441,459 B2 | 10/2019 | Aronhalt et al. |
| 10,470,813 B2 | 11/2019 | Allison et al. |
| 10,568,759 B2 | 2/2020 | Yee et al. |
| 10,575,890 B2 | 3/2020 | DeBenedictis et al. |
| 10,582,960 B2 | 3/2020 | Avram et al. |
| 10,596,030 B2 | 3/2020 | Karnik et al. |
| 10,646,666 B2 | 5/2020 | Cohn et al. |
| 10,675,178 B2 | 6/2020 | Levinson et al. |
| 10,806,500 B2 | 10/2020 | DeBenedictis et al. |
| 10,864,112 B2 | 12/2020 | Burger et al. |
| 10,869,779 B2 | 12/2020 | Burger et al. |
| 10,888,366 B2 | 1/2021 | Allison et al. |
| 10,912,599 B2 | 2/2021 | O'Neil et al. |
| 10,939,947 B2 | 3/2021 | Burger et al. |
| 11,076,879 B2 | 8/2021 | Yee et al. |
| 11,116,566 B2 | 9/2021 | Dinger et al. |
| 11,154,418 B2 | 10/2021 | Frangineas |
| 11,253,393 B2 | 2/2022 | Karnik et al. |
| 11,272,972 B2 | 3/2022 | Allison et al. |
| 11,284,934 B2 | 3/2022 | Lazarus et al. |
| 11,324,673 B2 | 5/2022 | Velis et al. |
| 11,437,150 B2 | 9/2022 | Rondoni et al. |
| 11,439,532 B2 | 9/2022 | Velis |
| 11,446,175 B2 | 9/2022 | Jimenez Lozano et al. |
| 11,446,178 B2 | 9/2022 | Velis |
| D967,164 S | 10/2022 | Mairs et al. |
| 11,457,971 B2 | 10/2022 | Wolf et al. |
| 11,478,643 B2 | 10/2022 | Verzal et al. |
| 11,504,322 B2 | 11/2022 | Garibyan et al. |
| 11,510,722 B2 | 11/2022 | Wolf et al. |
| 11,511,117 B2 | 11/2022 | Ni et al. |
| D971,935 S | 12/2022 | Mairs et al. |
| D971,936 S | 12/2022 | Mairs et al. |
| D971,937 S | 12/2022 | Mairs et al. |
| D971,950 S | 12/2022 | Mairs et al. |
| 11,517,365 B1 | 12/2022 | Mazor et al. |
| 11,583,438 B1 | 2/2023 | Levinson et al. |
| 2001/0051783 A1 | 12/2001 | Edwards et al. |
| 2002/0026226 A1 | 2/2002 | Ein |
| 2002/0062831 A1 | 5/2002 | Beyar et al. |
| 2002/0164729 A1 | 11/2002 | Skral et al. |
| 2003/0060685 A1 | 3/2003 | Houser |
| 2003/0069572 A1 | 4/2003 | Wellman |
| 2003/0220374 A1 | 11/2003 | Needleman |
| 2003/0220674 A1 | 11/2003 | Anderson et al. |
| 2004/0234576 A1 | 11/2004 | Martin et al. |
| 2004/0249416 A1 | 12/2004 | Yun et al. |
| 2005/0043682 A1 | 2/2005 | Kucklick |
| 2005/0133026 A1 | 6/2005 | Seleznev et al. |
| 2006/0235264 A1 | 10/2006 | Vassallo |
| 2007/0010861 A1 | 1/2007 | Anderson et al. |
| 2007/0129714 A1 | 6/2007 | Elkins et al. |
| 2007/0144539 A1 | 6/2007 | van der Burg et al. |
| 2007/0154538 A1 | 7/2007 | Neuberger et al. |
| 2007/0163603 A1 | 7/2007 | Sikora |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0023012 A1 | 1/2008 | Dineen et al. |
| 2008/0058584 A1 | 3/2008 | Hirotsuka et al. |

(56)　　　　　　References Cited

U.S. PATENT DOCUMENTS

| | | |
|---|---|---|
| 2008/0066769 A1 | 3/2008 | Dineen et al. |
| 2008/0066864 A1 | 3/2008 | Ballantine et al. |
| 2008/0077201 A1 | 3/2008 | Levinson et al. |
| 2008/0077202 A1 | 3/2008 | Levinson et al. |
| 2008/0077211 A1 | 3/2008 | Levinson et al. |
| 2008/0083461 A1 | 4/2008 | Viken |
| 2008/0132891 A1 | 6/2008 | Nobis |
| 2008/0183164 A1 | 7/2008 | Elkins et al. |
| 2008/0188947 A1 | 8/2008 | Sanders |
| 2008/0200910 A1 | 8/2008 | Burger et al. |
| 2008/0287839 A1 | 11/2008 | Rosen et al. |
| 2009/0014012 A1 | 1/2009 | Sanders |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0107001 A1 | 4/2009 | McCarthy |
| 2009/0118722 A1 | 5/2009 | Ebbers et al. |
| 2009/0120446 A1 | 5/2009 | Vaska et al. |
| 2009/0123886 A1 | 5/2009 | Vaska et al. |
| 2009/0149929 A1 | 6/2009 | Levinson et al. |
| 2009/0192504 A1 | 7/2009 | Askew |
| 2009/0287060 A1 | 11/2009 | Pell et al. |
| 2009/0287210 A1 | 11/2009 | Kauphusman |
| 2010/0057065 A1 | 3/2010 | Krimsky |
| 2010/0081971 A1 | 4/2010 | Allison |
| 2010/0100089 A1 | 4/2010 | Niethammer |
| 2010/0152824 A1 | 6/2010 | Allison |
| 2010/0280582 A1 | 11/2010 | Baker |
| 2011/0066216 A1 | 3/2011 | Ting et al. |
| 2011/0155143 A1 | 6/2011 | Shantha |
| 2011/0166598 A1 | 7/2011 | Gonazles et al. |
| 2011/0224761 A1 | 9/2011 | Manstein |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2012/0022518 A1 | 1/2012 | Levinson et al. |
| 2012/0085174 A1 | 4/2012 | Urbano |
| 2012/0239123 A1 | 9/2012 | Weber et al. |
| 2012/0265186 A1 | 10/2012 | Burger |
| 2013/0066309 A1 | 3/2013 | Levinson et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0158440 A1 | 6/2013 | Allison |
| 2013/0158636 A1 | 6/2013 | Ting et al. |
| 2013/0245731 A1 | 9/2013 | Allison |
| 2013/0253384 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2014/0005760 A1 | 1/2014 | Levinson et al. |
| 2014/0067025 A1 | 3/2014 | Levinson et al. |
| 2014/0257443 A1 | 9/2014 | Baker et al. |
| 2014/0277219 A1 | 9/2014 | Nanda |
| 2014/0277302 A1* | 9/2014 | Weber .................. A61F 7/0085 |
| | | 607/104 |
| 2014/0316393 A1 | 10/2014 | Levinson et al. |
| 2015/0047301 A1 | 2/2015 | Messersi' |
| 2015/0148791 A1 | 5/2015 | Birdsall et al. |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0251120 A1 | 9/2015 | Jakop |
| 2016/0022345 A1 | 1/2016 | Baust et al. |
| 2016/0051401 A1 | 2/2016 | Yee et al. |
| 2016/0183997 A1 | 6/2016 | Burnett et al. |
| 2016/0324576 A1 | 11/2016 | Ebbutt |
| 2016/0338752 A1 | 11/2016 | Sperling |
| 2016/0354234 A1* | 12/2016 | Dabrowiak ........... A61F 7/0085 |
| 2016/0354237 A1* | 12/2016 | Gonzales ............... A61B 18/02 |
| 2017/0079833 A1 | 3/2017 | Frangineas et al. |
| 2017/0105869 A1 | 4/2017 | Frangineas |
| 2017/0196731 A1 | 7/2017 | DeBenedictis et al. |
| 2017/0239079 A1 | 8/2017 | Root et al. |
| 2017/0246032 A1* | 8/2017 | Gonzales .................. A61F 7/12 |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'Neil et al. |
| 2018/0206900 A1 | 7/2018 | Sperling |
| 2018/0228646 A1 | 8/2018 | Gonzales et al. |
| 2018/0235805 A1 | 8/2018 | Burger et al. |
| 2019/0069949 A1 | 3/2019 | Vrba et al. |
| 2019/0151006 A1 | 5/2019 | Fourkas et al. |
| 2019/0192873 A1 | 6/2019 | Schwarz et al. |
| 2019/0197361 A1 | 6/2019 | Gonzales et al. |
| 2019/0254867 A1 | 8/2019 | Gonzales et al. |
| 2019/0290347 A1 | 9/2019 | Elkins et al. |
| 2020/0046552 A1 | 2/2020 | Velis et al. |
| 2020/0069458 A1 | 3/2020 | Pham |
| 2020/0138501 A1 | 5/2020 | DeBenedictis et al. |
| 2020/0206024 A1 | 7/2020 | Karnik et al. |
| 2020/0222103 A1 | 7/2020 | Manstein |
| 2020/0268439 A1 | 8/2020 | Frazier et al. |
| 2020/0323682 A1 | 10/2020 | O'Connor et al. |
| 2020/0375647 A1 | 12/2020 | Alphandery et al. |
| 2021/0030457 A1 | 2/2021 | Avram et al. |
| 2021/0038278 A1 | 2/2021 | DeBenedictis et al. |
| 2021/0128219 A1 | 5/2021 | Allison et al. |
| 2021/0186585 A1 | 6/2021 | Burger et al. |
| 2021/0282829 A1 | 9/2021 | O'Neil et al. |
| 2021/0315626 A1 | 10/2021 | Xiao et al. |
| 2021/0322084 A1 | 10/2021 | Velis et al. |
| 2021/0353351 A1 | 11/2021 | Mazor et al. |
| 2022/0008110 A1 | 1/2022 | Velis et al. |
| 2022/0047315 A1 | 2/2022 | Baker et al. |
| 2022/0125630 A1 | 4/2022 | Karnik et al. |
| 2022/0133531 A1 | 5/2022 | Salma et al. |
| 2022/0226206 A1 | 7/2022 | Velis et al. |
| 2022/0233863 A1 | 7/2022 | Rondoni et al. |
| 2022/0257272 A1 | 8/2022 | Wolf et al. |
| 2022/0265344 A1 | 8/2022 | Wolf, II et al. |
| 2022/0280788 A1 | 9/2022 | Verzal et al. |
| 2022/0288388 A1 | 9/2022 | Rondoni |
| 2022/0296887 A1 | 9/2022 | Johnson et al. |
| 2022/0338892 A1 | 10/2022 | Iyer et al. |
| 2022/0346852 A1 | 11/2022 | Anderson et al. |
| 2022/0387091 A1 | 12/2022 | DeBenedictis et al. |
| 2022/0401725 A1 | 12/2022 | Dieken et al. |
| 2022/0401727 A1 | 12/2022 | Rondoni et al. |
| 2023/0000669 A1 | 1/2023 | Babkin et al. |
| 2023/0028322 A1 | 1/2023 | Velis et al. |
| 2023/0031549 A1 | 2/2023 | Velis et al. |
| 2023/0046154 A1 | 2/2023 | Mazor et al. |
| 2023/0046673 A1 | 2/2023 | Velis et al. |
| 2023/0054472 A1 | 2/2023 | Hill et al. |
| 2023/0240887 A1 | 8/2023 | Gonzales et al. |
| 2024/0341830 A1 | 10/2024 | Kannan et al. |
| 2024/0341831 A1 | 10/2024 | Kannan et al. |
| 2025/0134915 A1 | 5/2025 | Gonzales et al. |
| 2025/0135004 A1 | 5/2025 | Gonzales et al. |

FOREIGN PATENT DOCUMENTS

| | | |
|---|---|---|
| AU | 2020272238 A1 | 10/2021 |
| AU | 2020412601 A1 | 7/2022 |
| AU | 2021324991 A1 | 3/2023 |
| CA | 3023821 A1 | 11/2017 |
| CA | 3044020 A1 | 7/2018 |
| CA | 3065606 A1 | 9/2018 |
| CA | 3115260 A1 | 4/2020 |
| CA | 3135707 A1 | 10/2020 |
| CA | 3162660 A1 | 7/2021 |
| CN | 108836619 A | 11/2018 |
| EP | 1890627 B1 | 6/2012 |
| EP | 2111172 B1 | 10/2013 |
| EP | 2094328 B1 | 8/2014 |
| EP | 2676623 B1 | 9/2015 |
| EP | 2162083 B1 | 12/2015 |
| EP | 2499984 B1 | 1/2016 |
| EP | 2967706 A1 | 1/2016 |

(56) References Cited

FOREIGN PATENT DOCUMENTS

| EP | 2687174 B1 | 10/2016 |
|---|---|---|
| EP | 3099258 A1 | 12/2016 |
| EP | 3099260 A2 | 12/2016 |
| EP | 3182918 A1 | 6/2017 |
| EP | 2802279 B1 | 8/2017 |
| EP | 3104796 B | 4/2019 |
| EP | 3488833 A1 | 5/2019 |
| EP | 3541345 A1 | 9/2019 |
| EP | 3342379 B1 | 10/2019 |
| EP | 3506846 A4 | 1/2021 |
| EP | 3099262 B1 | 2/2022 |
| EP | 4081746 A1 | 11/2022 |
| GB | 2423023 B | 10/2009 |
| HK | 40011648 A | 7/2020 |
| IL | 266662 A | 6/2019 |
| IL | 269038 A | 10/2019 |
| JP | H01-223961 A | 9/1989 |
| JP | 2022126649 A | 8/2022 |
| MX | 2019010396 A | 7/2020 |
| SG | 11201908076 | 9/2019 |
| SG | 11202103368 | 4/2021 |
| SG | 11202103636 | 5/2021 |
| WO | WO97/44092 A1 | 11/1997 |
| WO | WO99/003411 A1 | 1/1999 |
| WO | WO2003/078596 A2 | 9/2003 |
| WO | 2007101039 A1 | 9/2007 |
| WO | 2007127924 A2 | 11/2007 |
| WO | 2007133839 A1 | 11/2007 |
| WO | 2008016730 A2 | 2/2008 |
| WO | 2008039556 A1 | 4/2008 |
| WO | 2008039557 A1 | 4/2008 |
| WO | 2008060423 A2 | 5/2008 |
| WO | WO2008/055243 A2 | 5/2008 |
| WO | 2008143678 A1 | 11/2008 |
| WO | 2009011708 A1 | 1/2009 |
| WO | WO2009/026471 A1 | 2/2009 |
| WO | WO2010/036732 A1 | 4/2010 |
| WO | WO2010/127315 A2 | 11/2010 |
| WO | WO2011/091293 A1 | 7/2011 |
| WO | WO2011/091431 A1 | 7/2011 |
| WO | 2012012296 A1 | 1/2012 |
| WO | WO2012/103242 A1 | 8/2012 |
| WO | WO2012/103315 A2 | 8/2012 |
| WO | 2014151850 A2 | 9/2014 |
| WO | 2014151872 A2 | 9/2014 |
| WO | WO2016/033384 A1 | 3/2016 |
| WO | WO2017/223417 A1 | 12/2017 |
| WO | WO2018/044825 A1 | 3/2018 |
| WO | 2019046236 A2 | 3/2019 |
| WO | WO2020/142519 A1 | 7/2020 |
| WO | 2022169699 A1 | 8/2022 |
| WO | 2022229277 A1 | 11/2022 |
| WO | 2023278891 A1 | 1/2023 |
| WO | 2023064528 A1 | 4/2023 |
| WO | 2023130069 A2 | 7/2023 |

OTHER PUBLICATIONS

Coleman et al., Clinical Efficacy of Noninvasive Cryolipolysis and Its Effects on Peripheral Nerves, Aesth. Plast. Surg., 33: 482-488; Mar. 2009.

Day et al.; Popsicle Panniculitis; Pediatric Emergency Care; 8(2); 91-93; Apr. 1992.

Epstein et al.; Popsicle Panniculitis; NEJM; 282(17); 966-967; Apr. 23, 1970.

Gage et al.; Critical temperature for skin necrosis in experimental cryosurgery; Cryobiology; 19(3); pp. 273-282; Jun. 1982.

Kim et al.; Tongue fat and its relationship to obstructive sleep apnea; Sleep; 37(10); pp. 1639-1648; Oct. 2014.

Medicalxpress; Study shows that tongue size and fat may predict sleep apnea risk in obese adults; 3 pages retrived from the interenet (https://medicalxpress.com/news/2014-09-tongue-size-fat-apnea-obese.html) on Nov. 27, 2018.

Nelson et al., Cryolipolysis for Reduction of Excess Adipose Tissue; Semin. Cutan. Med. Surg., 28(4): 244-249; Dec. 1, 2009.

Rajkumar et al.; Popsicle Panniculitis of the Cheeks; Clinical Pediatrics.; 15 (7); 619-621; Jul. 1976.

Zelickson et al., Cryolipolysis for Noninvasive Fat Cell Destruction: Initial Results from a Pig Model; Dermatol, Surg., 35: 1462-1470; Oct. 2009.

Gonzalez et al., U.S. Appl. No. 18/058,159 entitled "Apparatus and Methods for Treatment of Obstructive Sleep Apnea Utilizing Cryolysis of Adipose Tissues," filed Nov. 22, 2022.

Soykan et al.; U.S. Appl. No. 17/793,154 entitled "Systems and methods for treatment of obstructive sleep apnea," filed Jul. 15, 2022.

Extended European Search Report mailed Apr. 9, 2018 in European Patent Application No. 15846755.5, 9 pages.

Extended European Search Report mailed Aug. 19, 2022 in European Patent Application No. 19907538.3, 8 pages.

Extended European Search Report mailed Dec. 15, 2023 in European Patent Application No. 21756850.0, 8 pages.

International Search Report mailed Dec. 28, 2015 in International Patent Application No. PCT/US15/51903, 10 pages.

International Search Report mailed Jun. 29, 2021 in International Patent Application No. PCT/US21/18926, 12 pages.

International Search Report mailed Jun. 6, 2023 in International Patent Application No. PCT/US22/82620, 11 pages.

International Search Report mailed May 1, 2020 in International Patent Application No. PCT/US19/69113, 11 pages.

International Search Report mailed May 16, 2012 in International Patent Application No. PCT/US12/22697.

Office Action mailed Jul. 18, 2017 in Canadian Patent Application No. 2,825,624, 3 pages.

Office Action mailed Jul. 18, 2018 in Canadian Patent Application No. 2,825,624, 4 pages.

Office Action mailed Oct. 27, 2021 in Canadian Patent Application No. 2,962,920, 5 pages.

Office Action mailed Sep. 13, 2023 in Canadian Patent Application No. 3,168,812, 4 pages.

Office Action mailed Sep. 22, 2023 in Canadian Patent Application No. 3,125,291, 5 pages.

Office Action mailed Jul. 25, 2023 in Japanese Patent Application No. 2021-538451, 7 pages, English translation.

Chakrabarti, P. et al., "FoxO1 controls insulin-dependent adipose triglyceride lipase (ATGL) expression and lipolysis in adipocytes," Journal of biological chemistry, 2009, vol. 284, No. 20, pp. 13296-13300.

Decision of Dismissal of Amendment mailed Nov. 12, 2024 in Japanese Patent Application No. 2021-538451, 4 pages, with English Translation.

Examination Report mailed Aug. 15, 2024 in Canadian Patent Application No. 3,125,291, 5 pages.

Examination Report mailed Aug. 15, 2024 in Canadian Patent Application No. 3,168,812, 4 pages.

Examination Report mailed Jul. 10, 2024 in European Patent Application No. 19907538.3, 4 pages.

Examination Report mailed Sep. 16, 2024 in Australian Patent Application No. 2019419502, 4 pages.

Ichioka, M. et al., "Increased expression of macrophage-inducible C-type lectin in adipose tissue of obese mice and humans," Diabetes, 2011, vol. 60, pp. 819-826.

International Search Report and Written Opinion mailed Jan. 31, 2025 in International Patent Application No. PCT/US24/51836, 10 pages.

Keuper, M. et al., "An inflammatory micro-environment promotes human adipocyte apoptosis," Molecular and cellular endocrinology, 2011, vol. 339, pp. 105-113.

Office Action mailed Apr. 16, 2024 in Japanese Patent Application No. 2021-538451, 4 pages, English Translation.

Tanaka, M. et al., "Macrophage-inducible C-type lectin underlies obesity-induced adipose tissue fibrosis," Nature communications, 2014, vol. 5, article:4982, pp. 1-13.

Examination Report mailed Sep. 5, 2025 in Canadian Patent Application No. 3,168,812, 4 pages.

(56) References Cited

OTHER PUBLICATIONS

Examination Report mailed Jul. 11, 2025 in Canadian Patent Application No. 3,125,291, 4 pages.
Invitation to Pay Additional Fees mailed Jul. 21, 2025 in International Patent Application No. PCT/US25/32063, 2 pages.
Invitation to Pay Additional Fees mailed Jul. 17, 2025 in International Patent Application No. PCT/US25/32067, 3 pages.
International Search Report mailed Sep. 9, 2025 in International Patent Application No. PCT/US25/32067, 16 pages.

* cited by examiner

302

302

1102

1102

1102

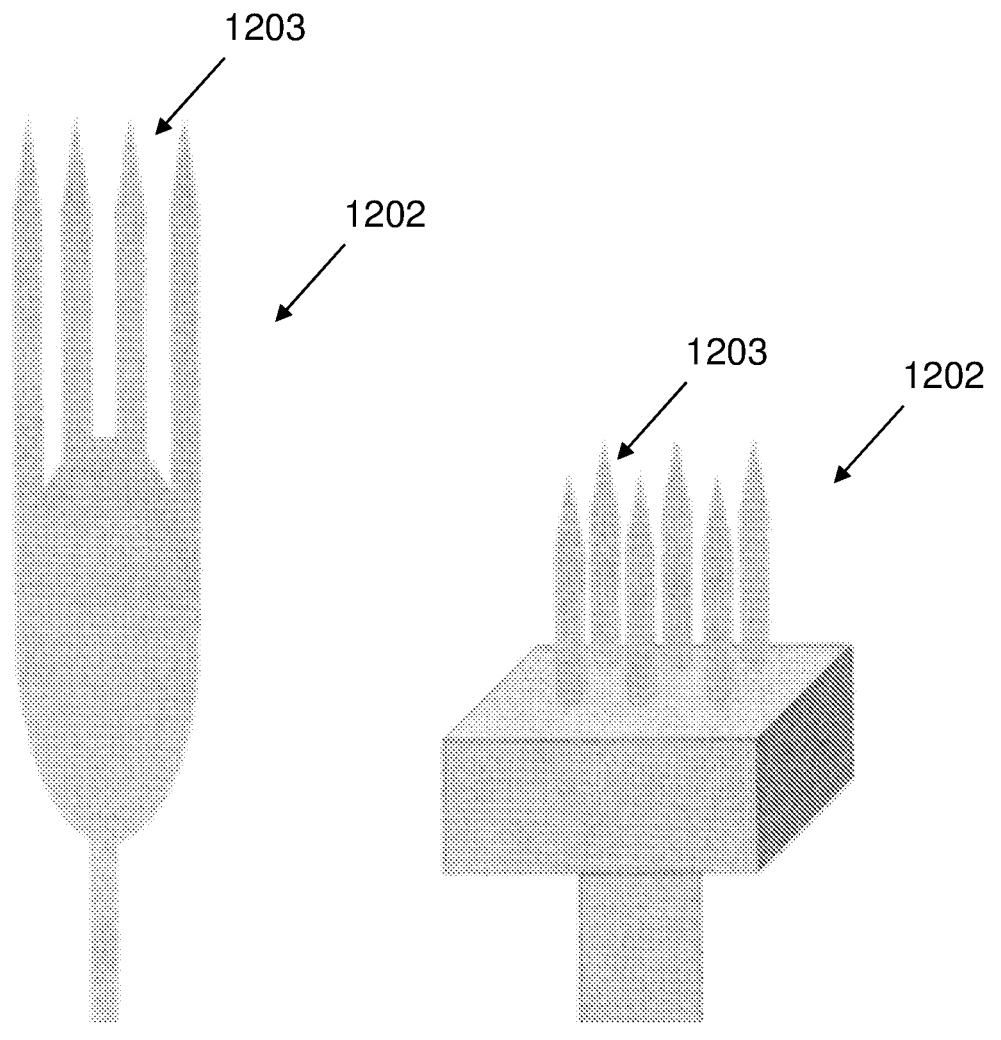
FIG. 12A      FIG. 12B

1502

1512

1514

1902

1913

2028

APPLICATOR

2432

2432

SYSTEMS AND METHODS FOR TREATMENT OF OBSTRUCTIVE SLEEP APNEA

CROSS REFERENCE TO RELATED APPLICATIONS

This application claims the benefit of priority to U.S. Provisional Application No. 62/787,125, filed December 31. 2018, titled "APPARATUS AND METHODS FOR TREATMENT OF OBSTRUCTIVE SLEEP APNEA UTILIZING CRYOLYSIS OF ADIPOSE TISSUES", and to U.S. Provisional Application No. 62/890,884, filed Aug. 23, 2019, titled "SYSTEMS AND METHODS FOR TREATMENT OF OBSTRUCTIVE SLEEP APNEA", both of which are herein incorporated by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present disclosure relates generally to minimally invasive treatment of obstructive sleep apnea.

BACKGROUND

Obstructive sleep apnea (OSA) is a sleep disorder that affects up to 20% of the adult population. OSA generally occurs during sleep when soft tissue enlarges and obstructs the pharyngeal airway, creating cessation of, or impeding, breathing due to the decrease in size of the upper airway, resulting in the breathing of the patient to repeatedly stop and restart.

Obstruction can occur at one or more levels including the retropalatal and retrolingual areas, and if untreated could leave to the development of serious complications, including atrial fibrillation and heart failure.

This enlargement of the tongue generally occurs due to excess body weight, causing adipose tissue to accumulate within the tongue. With the accumulation of adipose tissue, organs in the oral cavity, including the tongue, become enlarged and lose their firmness and grow in volume. Due to their inability to maintain their tone and their increase in size, they move into the airway and restrict airflow. One condition that is particularly concerning occurs when there is excess fat near the base of the tongue, which is adjacent the airway.

Surgical correction (such as glossectomy) of such obstructions remains a challenge, specifically for the retrolingual area. Removal or ablation of tongue tissue has been utilized with poor results due to complications, such as severe bleeding, abscess formation, and/or the inability to move the tongue anterior enough to relieve the obstruction. Medical devices such as tongue trainers also result in limited mobility or inconvenience to the patient.

Continuous positive airway pressure (CPAP) is a more noninvasive technique in relieving OSA than surgical operation, but is a remedy and not a permanent solution. Applying a stream of compressed air through the pharyngeal airway to overcome the collapsing soft tissue results in the patient being uncomfortable and fully dependent on the machine and its limitations, such as a stuffy nose, claustrophobia, skin irritation, pressure sores, and dry mouth. Additionally, the mechanics of the machine result in the CPAP mask possibly falling off during sleep, bothersome noises, and a leaky mask, all while being costly and electrically dependent. These factors lead to the patient having trouble falling asleep, demonstrating a faulty solution to curing OSA, since the patient will never be cured of their disease and will still have complications during sleep.

Adipose cryolysis is the use of cold to selectively target the submucosal adipose tissue, leading to a reduction in tissue volume via the removal of effected fat cells. However, it is known that the effect of cold on cells depend on various factors, including the cell type, duration that the cells are exposed to cold, rate of cooling and warming, as well as the number of cooling and warming cycles. When the adipocytes are exposed to temperatures below −15° C., necrosis occurs. At temperatures around −10° C., adipocytes are forced into a pathway that is reminiscent of apoptosis. When the temperatures are in the range of −5° C. to +10° C., cells may move into a hyper-metabolic state, resulting in thermogenesis, which may also reduce the lipid volumes, or result in adipocyte cell death.

Above observations may indicate that the exposure to temperatures in the range of +5° C. to −15° C. for 1-100 minutes may cause maximum damage to the adipose tissue while minimizing the damage to muscle. Furthermore, even when the 70-80% of the skeletal muscle is damaged, muscle does recover within few days, thanks to its regenerative capacity. These facts can be used during the design of the devices that can be used for the selective elimination of the adipose tissue while preserving the other types of tissues such as the skeletal muscle, blood vessels and the nerves.

The removal of adipocyte tissue (fat) from the tongue is expected to reduce the volume of tissue in the oropharynx, and the reduction of this tissue is known to cure or reduce the severity of obstructive sleep apnea, as demonstrated by the clinical outcomes of other procedures, such as the glossectomy of the tongue and the mandibular advancement.

Furthermore, the removal of the fat from within key tongue muscles, such as the genioglossus muscle, will improve the ability of these muscle groups to function, which in turn may result in the reduction of obstructive sleep apnea. These muscles do keep the tongue from falling back into the airway, in both their activated and passive states. Adipose tissue that is interspersed within the muscle act as a restriction to the muscle due to the mass and inability of the adipose tissue to move in the same manner as the adjacent muscle fibers.

To date, however, cryolitic treatment of OSA has involved procedures analogous to ablation, merely substituting cryolitic cold for electrolytic heat and non-selectively destroying all tissues in a similar manner—and with the same complications as the non-cryolitic therapies.

It is known that patients with OSA have a higher percentage of adipose deposits in the areas of obstruction, specifically, the soft palate and uvula, base of tongue and lateral pharyngeal walls. The adipose tissue may be up to or greater than 40% of the total volume of tissues in these areas. Removal of the fat deposits in these areas would permit relief from OSA symptoms while preserving surrounding tissue. To date, however, cryolytic treatment of OSA has involved procedures analogous to ablation, merely substituting cryolytic cold for electrolytic heat and nonselectively destroying tissue in a similar manner—and with the same complications.

Technologies that are used for the treatment of obstructive sleep apnea range from non-invasive ones such as continuous positive air pressure (CPAP), to surgical modifications such as glossectomy where the part of the tongue is removed, to medical devices such as tongue trainers. Unfortunately, many of these technologies either provide limited results or create much inconvenience to the patients. Hence, there is an unmet medical need to build a minimally invasive technique for the treatment of the patients with obstructive sleep apnea.

SUMMARY OF THE DISCLOSURE

The present invention employs adipose cryolysis in a tissue-selective manner by selectively removing fat cells from the tissues responsible for the OSA, such as the oropharyngeal tissues, and exploits the fact that adipocytes have a heightened to susceptibility to cooling compared to other types of cells, resulting in the slow and steady digestion of the effected tissues by the surrounding macrophages. Related systems, methods of use, and design parameters are provided herein.

In various embodiments, this disclosure exploits the particular cryolitic vulnerability of adipose tissue to provide a medical device to treat OSA without damaging and/or reducing the function of oropharyngeal tissue. Certain embodiments of the medical device may include engagement members that are formed in the shape of each specific area to be cooled, or are configured to cool multiple organs at once. Some embodiments may utilize grasping portions configured to grasp or pinch targeted anatomical structures, such as the soft palate, base of the tongue and the soft tissues of the pharynx, which are known to be associated with OSA, thereby cooling the tissue between the grasping portions and ensuring good mechanical contact during cooling. In some embodiments, the medical device may pierce the mucosa to cool the underlying tissues. The medical device may also be configured to inject a cooling agent into the underlying tissue to reduce the temperature of the deeper tissues. Additionally, the medical device may include engagement members configured to pierce the lower submaxillary triangle in order to reach more inaccessible areas of the adipose tissue on the lower tongue.

Accordingly, in a first aspect, the disclosure pertains to a device for the treatment of obstructive sleep apnea. In various embodiments, the device comprises a liquid cooling unit for chilling a cooling fluid and an applicator for receiving the cooling fluid. The applicator is configured for contact with oropharyngeal tissue, and the applicator and liquid cooling unit cooperatively cause cooling of the oropharyngeal tissue to a temperature between approximately 5° C. and approximately −25° C. for approximately 1 to approximately 100 minutes, whereby a volume of adipose tissue in the contacted oropharyngeal tissue is subsequently reduced.

In various embodiments, the applicator comprises an engagement member complementary to a target portion of the oropharyngeal tissue, and the applicator further includes a recirculation conduit for facilitating heat transfer between the engagement member and the cooling fluid. In some implementations the engagement member is flexible and conformal, while in other implementations the engagement member is rigid. The engagement member can comprise varying shapes depending on the target tissue. For example, the engagement member can be a substantially flat plate, "C"-shaped and complementary to a base of a tongue, 'V'-shaped and configured to engage a soft palate or a uvula, 'M' shaped and configured to engage the uvula, tonsils, and fat pads, cylindrical and hollow to cradle the uvula, or cylindrical to reach the lateral walls/fat pads. A rigid engagement member may be hinged, and the applicator may further include a control member, such as a wire, facilitating the closure of the engagement member to grasp the tissue. The applicator may be attached to a handle of the device by one of many techniques such as a free or motorized ball joint to increase mobility and to improve the pressure distribution across the surface of the tissue.

In some embodiments, the applicator may be configured to provide suction to the engagement member to enhance the mechanical contact with the oropharyngeal tissue. In other embodiments, the applicator comprises a needle configured for the injection of cooling fluid into the target portion of the oropharyngeal tissue, whether it be through the oral cavity or through the submaxillary triangle.

In various embodiments, the cooling fluid or the coolant is a liquid, e.g., a refrigerant or a water and glycerin or sropylene glycol solution. The cooling unit may be configured for feedback operation to maintain a substantially constant temperature at the target portion of the oropharyngeal tissue. To facilitate feedback operation, the cooling unit may be responsive to a temperature sensor that senses the temperature of the target tissue. In another embodiment, the temperature of the coolant entering the applicator can be compared to the temperature of the coolant exiting the applicator which can be used to determine the amount of heat or watts removed from the tissue. In other embodiments, the cooling fluid is chilled gas, such as air or nitrogen. For example, the applicator may comprise of a tube for introducing the chilled gas into the oropharynx and an inflatable member for scaling the esophagus and preventing the chilled air from entering the lower respiratory tract. In various implementations, the tube comprises inner and outer coaxial lumens, where the inner lumen has a portion extending past an end of the outer lumen and an inflatable member thereon. The cooling unit sends chilled air through the outer lumen and breathable air through the inner lumen. In other embodiments, the cooling fluid is a chilled biocompatible liquid, and the applicator comprises a tube for introducing the liquid into the oropharynx and an inflatable member for sealing the esophagus and preventing aspiration.

Other objects, features and advantages of the present disclosure will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the teachings of the present invention, and the invention includes all such modifications.

In the ensuing discussion, unless defined otherwise, all technical and scientific terms used herein generally have the same meaning as commonly understood by one of ordinary skill in the relevant art.

The term "coupled" is defined as connected, although not necessarily directly, and not necessarily mechanically; two items that are "coupled" may be integral with each other.

The terms "substantially," "approximately," and "about" are defined as largely but not necessarily wholly what is specified, as understood by a person of ordinary skill in the art. In various embodiments, these terms connote+10% and in some embodiments+5%.

The terms "comprise" (and any form of comprise, such as "comprises" and "comprising"), "have" (and any form of have, such as "has and "having"), "include" (and any form of include, such as "includes" and "including") and "contain" (and any form of contain, such as "contains" and "containing") are open-ended linking verbs. As a result, a system that "comprises." "has." "includes," or "contains" one or more elements possesses those one or more elements, but is not limited to possessing only those elements. Likewise, a method that "comprises." "has," "includes," or "contains," one or more steps possesses those one or more steps, but is not limited to possessing only those one or more steps. For example, in a method that comprises providing a tongue stabilization device, the method includes the specified steps but is not limited to having only those steps. For example, such a method could also include inserting the device through an incision into the tongue of a patient.

Further, a device or structure that is configured in a certain way is configured in at least that way, but it can also be configured in other ways than those specifically described.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 12A-12C illustrate the design of an applicator with a plurality of penetrating cryo needles.

SUMMARY OF THE DISCLOSURE

Figure 1:
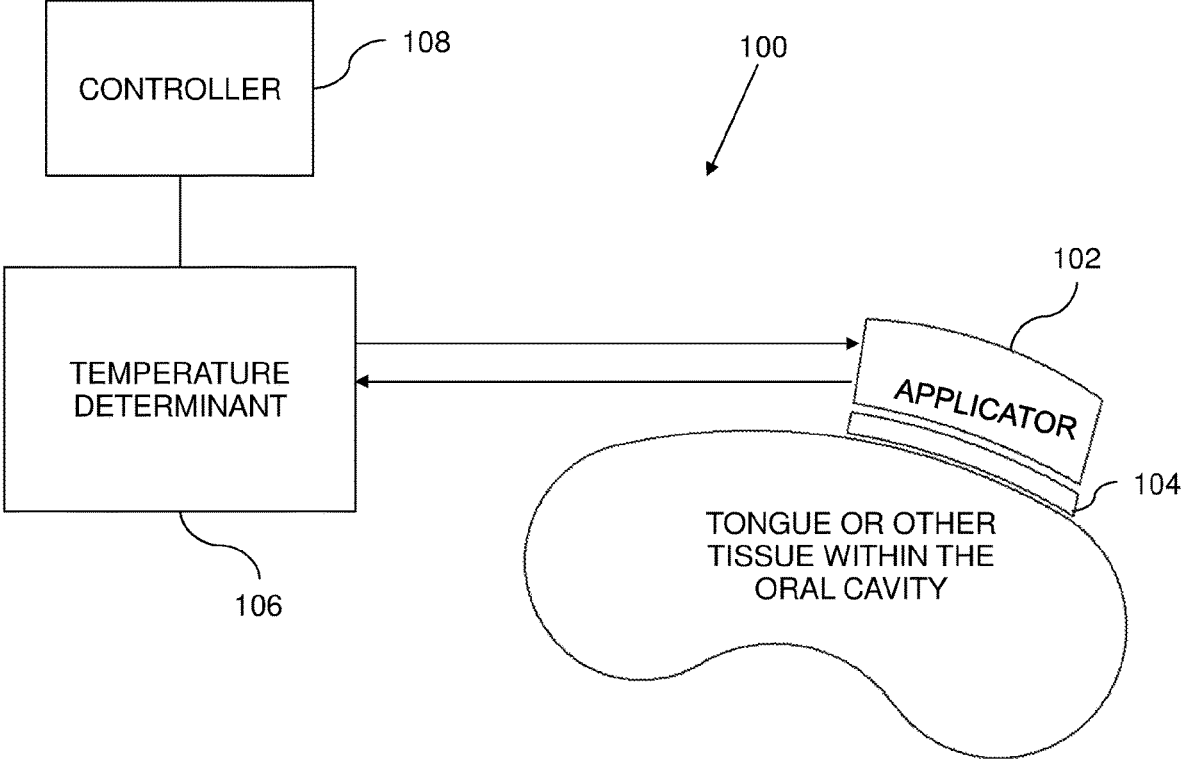
FIG. 1 depicts one example of a medical device for treatment of OSA.

A device for treatment of obstructive sleep apnea is provided, the device comprising a cooling unit for chilling a cooling fluid, an applicator configured to receive the cooling fluid, the applicator comprising a distal portion having a plurality of cryo therapy needles and a proximal portion, wherein the plurality of cryo therapy needles are shaped and configured to be inserted into a dorsal portion of a tongue of a subject, and wherein the proximal portion is shaped and configured to contact an adjacent portion of the tongue, and a recirculation conduit configured to facilitate heat transfer between the applicator and the cooling fluid, the applicator and cooling unit being configured to cooperatively cause cooling of the tongue for a time sufficient to cause cryolysis of adipose tissue within the tongue and thereby reduce a volume of the adipose tissue.

In some embodiments, the plurality of cryo therapy needles are arranged in a planar configuration. In other embodiments, the plurality of cryo therapy needles are arranged in a three-dimensional configuration.

In some examples, the distal portion is curved or substantially flat. In other embodiments, the proximal portion is curved or substantially flat.

In one example, the cooling fluid is configured to circulate within the plurality of cryo therapy needles.

In one example, the cooling unit comprises a two-stage cooling unit. In one embodiment, the two-stage cooling unit further comprises a first stage having a chiller, a first fluid circuit, and a pump, a second stage having a pump and a second fluid circuit, and a peltier booster disposed between the first stage and the second stage.

A method for treating obstructive sleep apnea in a subject is provided, the method comprising steps of inserting a penetrating cooling device through a submaxillary triangle of a subject with obstructive sleep apnea into an oropharyngeal tissue of the subject, cooling the penetrating cooling device for a time sufficient to cause cryolysis of adipose tissue within the oropharyngeal tissue, and reducing a volume of the adipose tissue within the oropharyngeal tissue.

In some embodiments, the target surface of the oropharyngeal tissue includes one or more of: a soft palate, a uvula, a tongue, or a pharyngeal wall.

In some embodiments, the cooling surface is configured to be placed in contact with the surface of the oropharyngeal tissue between approximately one minute and approximately one hundred minutes to cause cryolysis of adipose tissue within the oropharyngeal tissue.

In some embodiments, cooling the target surface of the oropharyngeal tissue or the underlying tissue in the subject with obstructive sleep apnea for a time sufficient to cause cryolysis of adipose tissue within the oropharyngeal tissue includes cooling the adipose tissue to a temperature of between about 0° C. and a body temperature.

In some embodiments, the penetrating cooling device is in fluid communication with a cooling unit for chilling a cooling fluid, and further comprising: chilling the cooling fluid with the cooling unit prior to cooling the penetrating cooling device.

In some embodiments, the method further comprises applying a cryoprotectant to a surface of the oropharyngeal tissue.

A device for treatment of obstructive sleep apnea is also provided, the device comprising a cooling unit for chilling a cooling fluid, an applicator configured to receive the cooling fluid, the applicator comprising a hollow cylindrical shape configured to receive a uvula of a subject with sleep apnea when the applicator is placed over the uvula, and a recirculation conduit configured to facilitate heat transfer between the applicator and the cooling fluid, the applicator and cooling unit being configured to cooperatively cause cooling of the uvula for a time sufficient to cause cryolysis of adipose tissue within the uvula and thereby reduce a volume of the adipose tissue.

A device for treatment of obstructive sleep apnea is provided, the device comprising a cooling unit for chilling a cooling fluid, an applicator configured to receive the cooling fluid, the applicator being shaped and configured to simultaneously contact a uvula, one or more tonsils, and one or more fat pads of a subject's oral cavity, and a recirculation conduit configured to facilitate heat transfer between the applicator and the cooling fluid, the applicator and cooling unit being configured to cooperatively cause cooling of the uvula, the one or more tonsils, and the one or more fat pads for a time sufficient to cause cryolysis of adipose tissue within the uvula, the one or more tonsils, and the one or more fat pads and thereby reduce a volume of the adipose tissue.

In some embodiments, the applicator comprises a pair of tonsil contacting extensions on each side of the applicator.

In other embodiments, the applicator comprises a uvula contacting portion.

In one embodiment, the uvula contacting portion comprises a cylindrical shape.

In some embodiments, the device further comprises a pair of connecting member portions between the tonsil contacting portions and the uvula contacting portion.

A device for treatment of obstructive sleep apnea is provided, the device comprising a cooling unit for chilling a cooling fluid, an inflatable applicator configured to contact an oropharyngeal tissue of a subject, the inflatable applicator having a therapy portion configured to receive the cooling fluid and an insulative portion that does not receive the cooling fluid, and a recirculation conduit configured to facilitate heat transfer between the therapy portion of the applicator and the cooling fluid, the therapy portion of the applicator and cooling unit being configured to cooperatively cause cooling of the oropharyngeal tissue of the subject for a time sufficient to cause cryolysis of adipose tissue within the oropharyngeal tissue and thereby reduce a volume of the adipose tissue.

A method for treating obstructive sleep apnea in a subject is provided, the method comprising steps of applying an inflatable applicator to an oropharyngeal tissue of a subject with obstructive sleep apnea, applying a cooling fluid to a therapy portion of the inflatable applicator for a time sufficient to cause cryolysis of adipose tissue within the oropharyngeal tissue, reducing a volume of the adipose tissue within the oropharyngeal tissue, and insulating targeted locations of the oropharyngeal tissue with an insulated portion of the inflatable applicator.

A method for treating obstructive sleep apnea in a subject is provided, the method comprising steps of applying an applicator to an oropharyngeal tissue of a subject with obstructive sleep apnea, measuring a force applied by the applicator to one or more locations of the oropharyngeal tissue with one or more force sensors of the applicator, adjusting a force applied by the applicator to the oropharyngeal tissue based on the measured force, applying a cooling fluid to the applicator for a time sufficient to cause cryolysis of adipose tissue within the oropharyngeal tissue, and reducing a volume of the adipose tissue within the oropharyngeal tissue.

A method for treating obstructive sleep apnea in a subject is provided, the method comprising steps of applying an applicator to an oropharyngeal tissue of a subject with obstructive sleep apnea, measuring a temperature of one or more locations of the oropharyngeal tissue with one or more temperature sensors of the applicator, applying a cooling fluid to the applicator for a time sufficient to cause cryolysis of adipose tissue within the oropharyngeal tissue, and reducing a volume of the adipose tissue within the oropharyngeal tissue.

A method for treating obstructive sleep apnea in a subject is provided, the method comprising steps of applying an applicator to an oropharyngeal tissue of a subject with obstructive sleep apnea, applying a cooling fluid to the applicator for a time sufficient to cause cryolysis of adipose tissue within the oropharyngeal tissue, reducing a volume of the adipose tissue within the oropharyngeal tissue, and rapidly warming the oropharyngeal tissue immediately after applying the cooling fluid to prevent damage to mucosal layers adjacent to the oropharyngeal tissue.

In some embodiments, the cooling fluid has a temperature ranging from 5 deg C. to −20 deg C.

In other embodiments, the rapidly warming step comprises heating the cooling fluid.

DETAILED DESCRIPTION

Provided herein are devices and methods to treat obstructive sleep apnea. A sleep apnea treatment system 100 according to the disclosure herein, and illustrated in FIG. 1, can include four major components: an oral applicator 102, a cryoprotectant 104, a temperature determinant 106, and a controller 108. The following description provides details and examples of design and operation of the overall system and its individual components. Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the teachings of the present invention, and the invention includes all such modifications.

FIG. 1 demonstrates one overall configuration of a sleep apnea treatment system 100 in a clinical setting with four major components, in which a controller 108 is connected to a temperature determinant 106, which has one or more lines connected to an oral applicator 102. The temperature determinant can be configured to store, generate, or produce a volume of coolant. For example, the temperature determinant can be a simpler refrigerant chiller that couples the cold to a recirculating fluid that goes through the applicator. In another embodiment, the temperature determinant can also be a peltier device, either positioned locally on the probe or remotely from the applicator, whereby the peltier device chills a recirculating fluid that goes through the applicator. In this example, there can also be a secondary loop of coolant to cool the peltier device. Gas expansion systems could also be used by allowing a compressed gas to expand in or near the applicator resulting in rapid cooling.

In the illustrated example, one line is configured to allow the flow of coolant from the temperature determinant 106 into the applicator and the other line is configured for the outflow of the coolant from the applicator to the temperature determinant. In some embodiments, the circulation of the coolant can be facilitated by a pump disposed on or in the temperature determinant, the lines, or the applicator. At the site of the application to the tongue, a cryoprotectant 104 can be configured to cover at least a portion of the surface of the applicator, being placed over the targeted oral tissue. Cryoprotectant may be applied directly or by a carrier, such as a sheet.

The controller 108 can be an electronic controller or computer/CPU system and be configured to control the overall operation of the system 100, including managing the temperature of the coolant in the temperature determinant and the flow of coolant to/from the applicator. In some examples, the controller controls the system based on feedback from one or more sensors of the system, including for example, temperature sensors on or within the targeted tissue.

The applicator of the sleep apnea treatment system is designed and configured to be placed within the oral cavity of the subject. The applicator is the part of the system that is in direct contact with the target tissue or tissues of the patient to be treated. In some examples, the applicator is constructed using metal, plastic, or ceramic components and can be sanitized or sterilized before use. The applicator can be rigid or flexible, depending on the target tissue. Furthermore, the applicator can also be reusable or disposable. The applicator is designed and configured to both remove and deliver heat at rates in the range of 0.2 Watts to 95 Watts to and from the tongue of a patient for a period of 1 minute to 100 minutes.

In some embodiments, the applicator is composed of multiple parts. Each part of the applicator may be connected to another part of the applicator or may be independent of the other parts of the applicator. Each part of the applicator is capable of extracting heat and/or delivering heat from the tissue segments that it gets in contact. Furthermore, each segment could be different shape and size, and maybe designed to treat different parts of the tissues in the oral cavity. Coolant flow to these individual parts of the applicator could be configured to be in parallel, series or in combination of parallel or series. Furthermore, the design of each applicator part may be different. For example, the applicator part that is treating the tongue could be a rigid metal device while the applicator part that is treating the lateral walls could be balloon type.

Since the anatomy of the oral structures vary from subject to subject, it is advantageous to design a range of applicators and select the one that is most suitable for a given patient. Alternatively, the applicator can be made from a compliant or a deformable material. In one embodiment of the invention, the applicator is a constructed using a soft and stretchable elastic material, allowing it to have characteristics of an inflatable balloon. In that case, the balloon is initially advanced into place in the oral cavity and then inflated using a warm fluid to make sure that it makes firm contact with the surfaces. Afterwards, the fluid is chilled while maintaining the pressure to deliver the cryolysis therapy. At the end of the treatment period, the liquid that is in the applicator is warmed and the applicator is deflated before its removal. In some embodiments of the invention, the compliant balloon has uniform thermal conductivity and delivers the therapy to all surfaces that it comes in contact with. In other embodiments, the balloon has thermal insulation features, consisting of different materials and thickness at different sites, or additional air filled chambers, to form thermal insulation to protect the oral structures that are not supposed to experience cold temperatures.

Figure 2A:
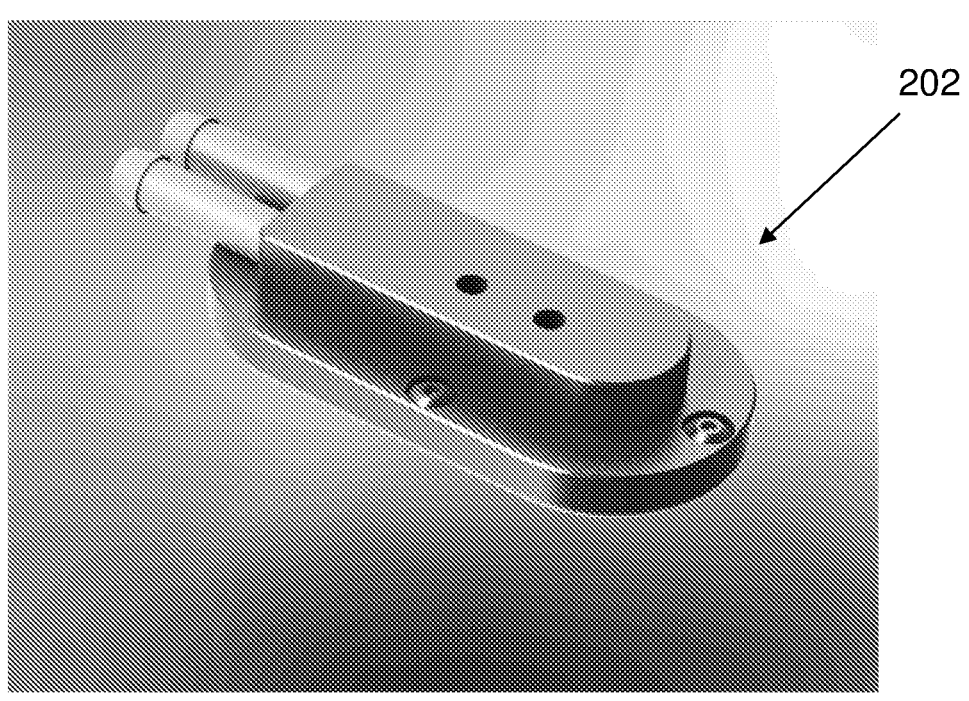
FIG. 2A shows an exemplary design of the applicator with a flat bottom surface, where
Figure 2B:
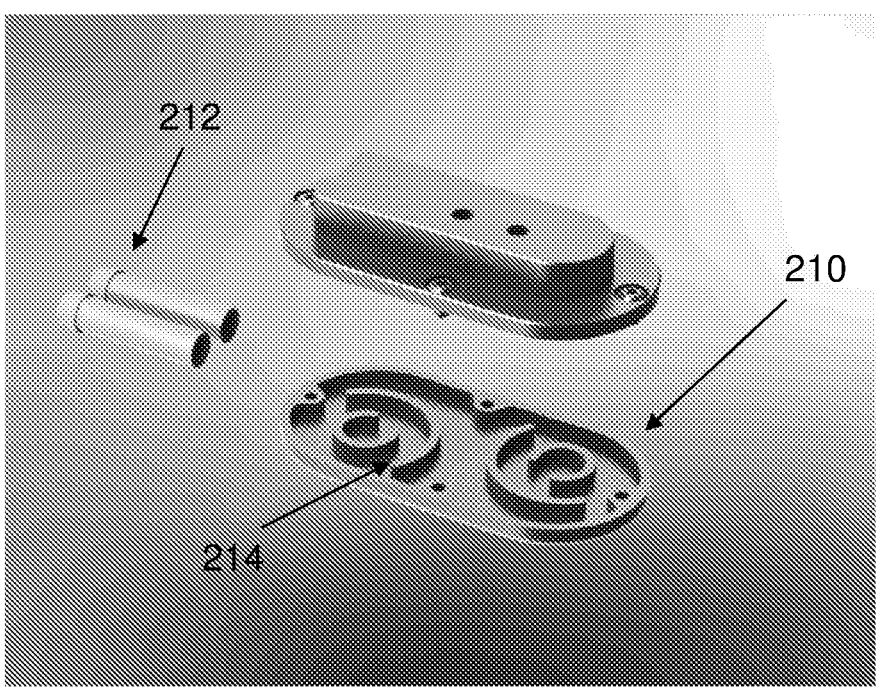
FIG. 2B shows the applicator that is assembled.

A flat bottomed applicator 202 is shown in FIGS. 2A-2B. Such an applicator can have width in the range of 1 cm to 5 cm and length in the range of 1 cm to 8 cm. The applicator can include a hollow cavity 210 and tubing 212 configured to provide a cooling fluid into the cavity of the applicator. The hollow cavity may include, for example, flow paths 214 for the cooling fluid defined. For example, referring to FIG. 2B, the hollow cavity may include two distinct flow paths characterized by partial circular walls or baffles to promote circular and even flow of the fluid on both halves of the applicator. Furthermore, the tubing carrying the coolant are also insulated. A typical target temperature for the applicator can be in the range of +15° C. to −25° C., preferably in the range of −5° C. to −15° C.

Figure 3A:
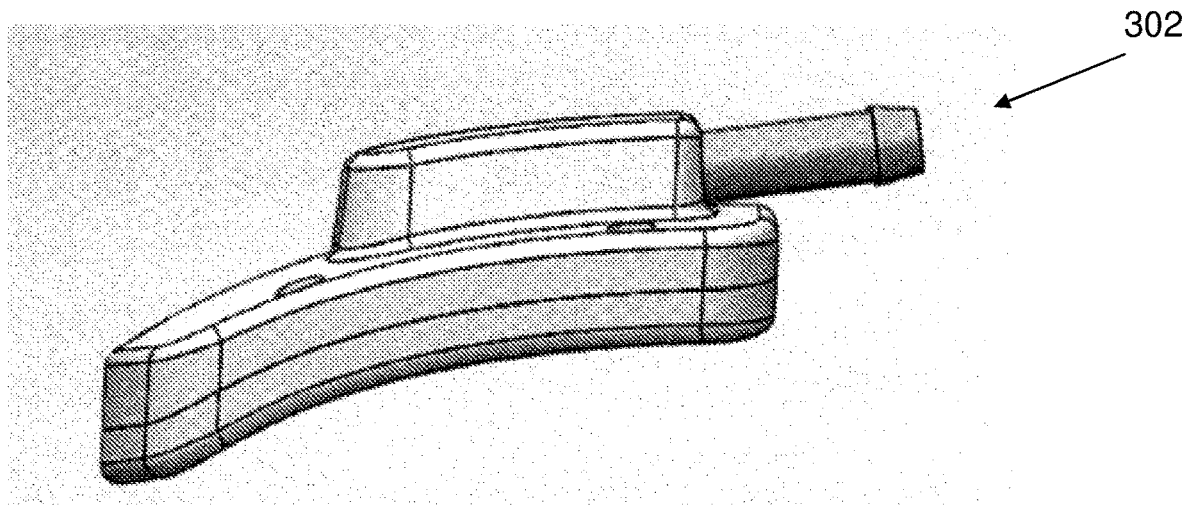
FIG. 3A shows a side view of an applicator with a curved shape to match the tongue anatomy, particularly the base of tongue curvature.

Some embodiments of the applicator may have a flat bottom, and other embodiments of the applicator may have a curved bottom. Since the target tissue may be toward the base of the tongue, it may be advantageous to use an applicator with curved bottom. FIG. 3A shows the side view of an applicator with a curved shape configured to match the typical tongue anatomy, particularly the base of tongue curvature. The surface mating the tongue may be smooth or may have texture or ridges that increase surface area and/or hold the cryoprotectant in place during the treatment.

Figure 3B:
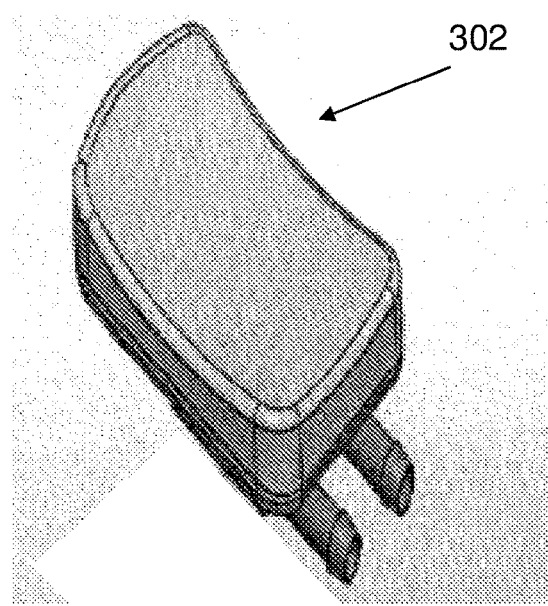
FIG. 3B shows a bottom view of an applicator with a curved shape to match the tongue anatomy, particularly the curvature of the base of the tongue.

FIG. 3B shows a bottom view of an applicator 302 with a curved shape to match the tongue anatomy, particularly the curvature of the base of the tongue.

Figure 3C:
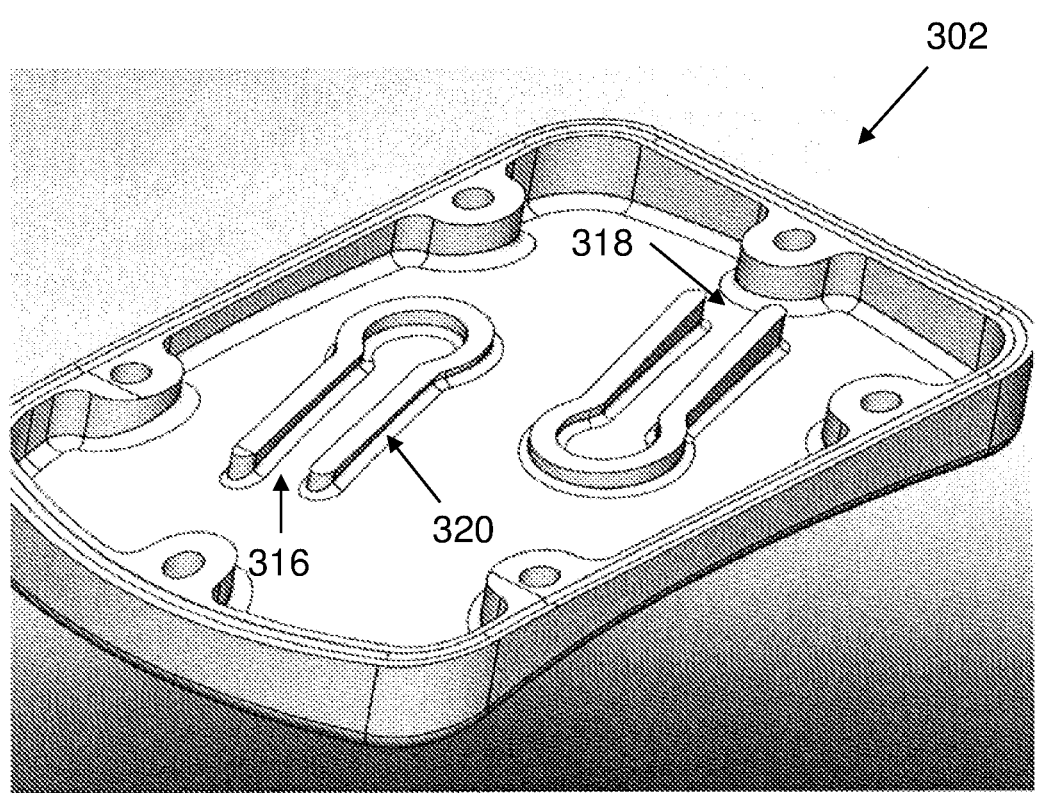
FIG. 3C shows an internal view of the applicator with cryo fluid inlet and outlet shown, with baffles to direct cryo fluid for even distribution of cryo temperatures across the applicator surface.

FIG. 3C shows an internal view of the applicator with a cryo fluid inlet 316 and outlet 318 shown, with baffles 320 configured to direct cryo fluid for even distribution of cryo temperatures across the applicator surface.

Figure 4:
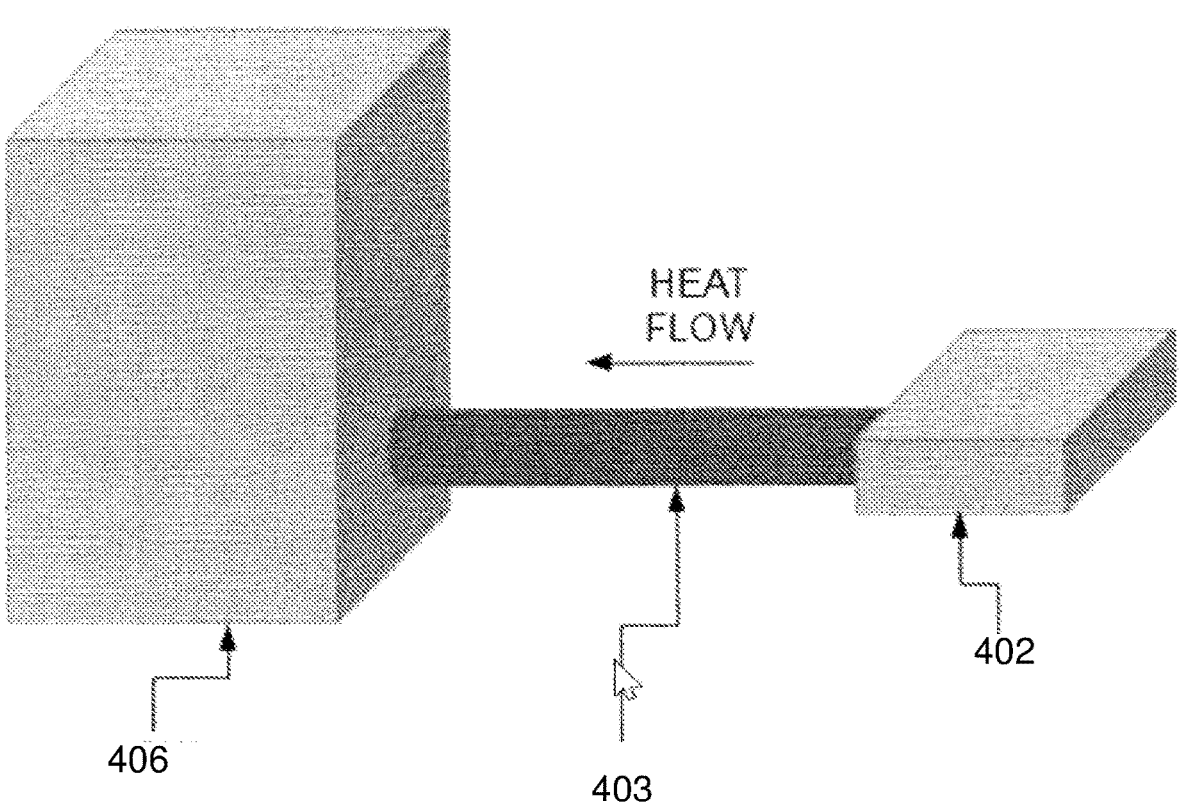
FIG. 4 shows one implementation of the medical device where the heat extraction is done by conduction.

The applicator described herein is configured to provide a cooling therapy which is essential for heat extraction from the target tissue. The cooling can be accomplished by for example, including onsite cooling, cooling by conduction, and cooling by convention. For onsite cooling, the cooling device can be placed in the applicator itself. The cooling device can be a thermoelectric cooler, such as a Peltier cooler, a Joule-Thompson device where a gas is allowed to expand, or a phase change device where a fluid is allowed to evaporate by taking heat from the applicator. Referring to FIG. 4, the applicator 402 is connected to an external cooling unit or heat extractor 406 by a heat conductor 403, such as a metal rod, as shown in FIG. 4.

Thermal power that is being transmitted by a metal rod is given by:

$$P = \left(\frac{kA}{L}\right)\Delta T. \qquad \text{Equation. 1}$$

where P is the thermal power in Watts,
k is the conductivity of the material,
A is the cross section of the material,
L is the length of the material, and ΔT is the temperature difference between the two ends of the material.

If the metal rod is made out of copper with conductivity value of k=401 Watts/(m.° C.), having a radius of R=2 cm and length of L=20 cm used, and one end of the rod is kept at −20° C. while the other end is in contact with the applicator at +37° C., then the heat flow can be calculated as P=143 Watts using the Equation 1.

Figure 5:
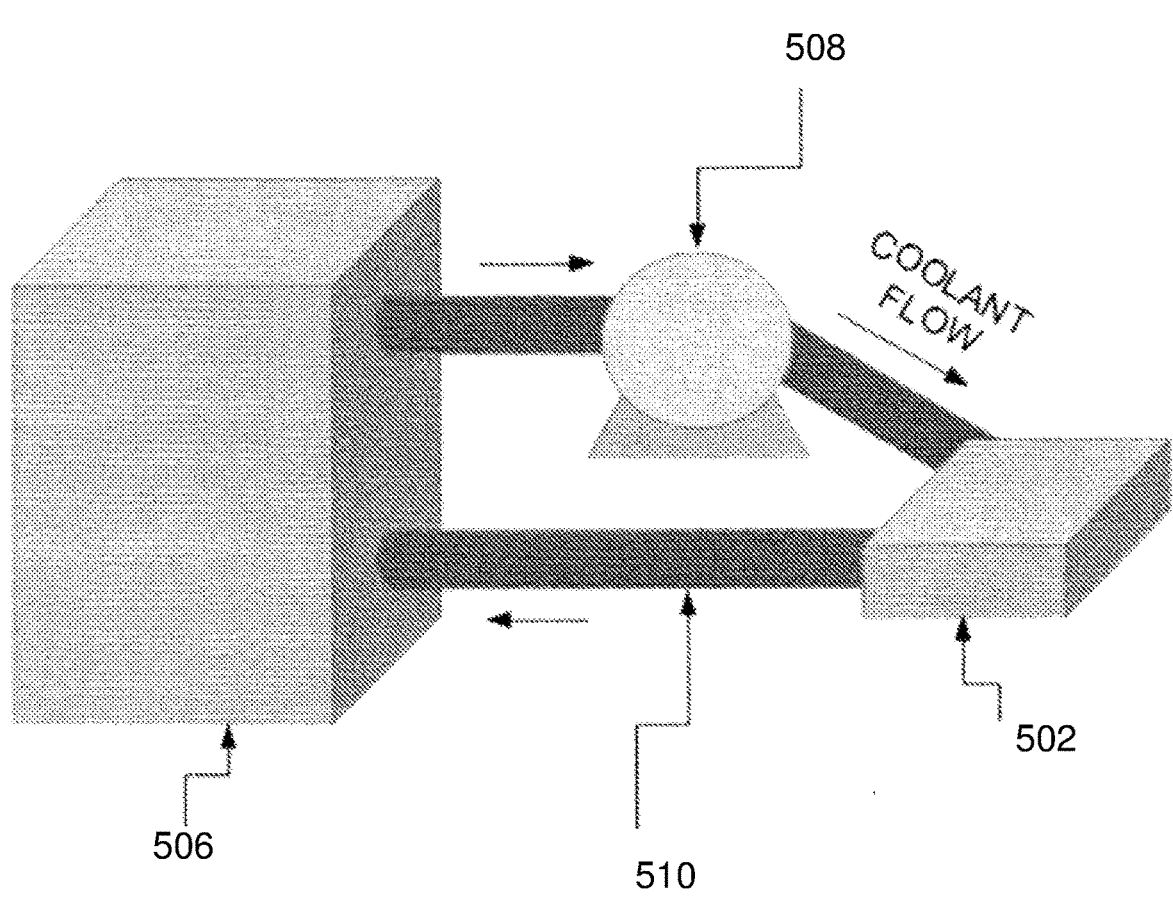
FIG. 5 shows one embodiment of a heat extractor.

Referring to FIG. 5, for convective cooling, the applicator 502 receives a coolant, in the form of chilled fluid or gas, from an external cooling unit 506 where the coolant is circulated via pump 508 and conduit 510 to remove the heat that is being extracted by the applicator, as shown in FIG. 5.

Heat removed by a fluid flow system is given by:

$$P = \varphi(\Delta T)c \qquad \text{Equation 2.}$$

where P is the thermal power in Watts,
φ is the coolant flow rate,
ΔT is the temperature rise in the coolant, and
c is the specific heat of the coolant.

If a coolant with a specific heat of c=4 Joules/(cc.° C.) is used with a flow rate of q=15 mL/sec and the temperature drop across the is ΔT=2° C., then the heat that is being extracted from the tissue can be calculated as P=120 Watts using the Equation 2.

Figure 6:
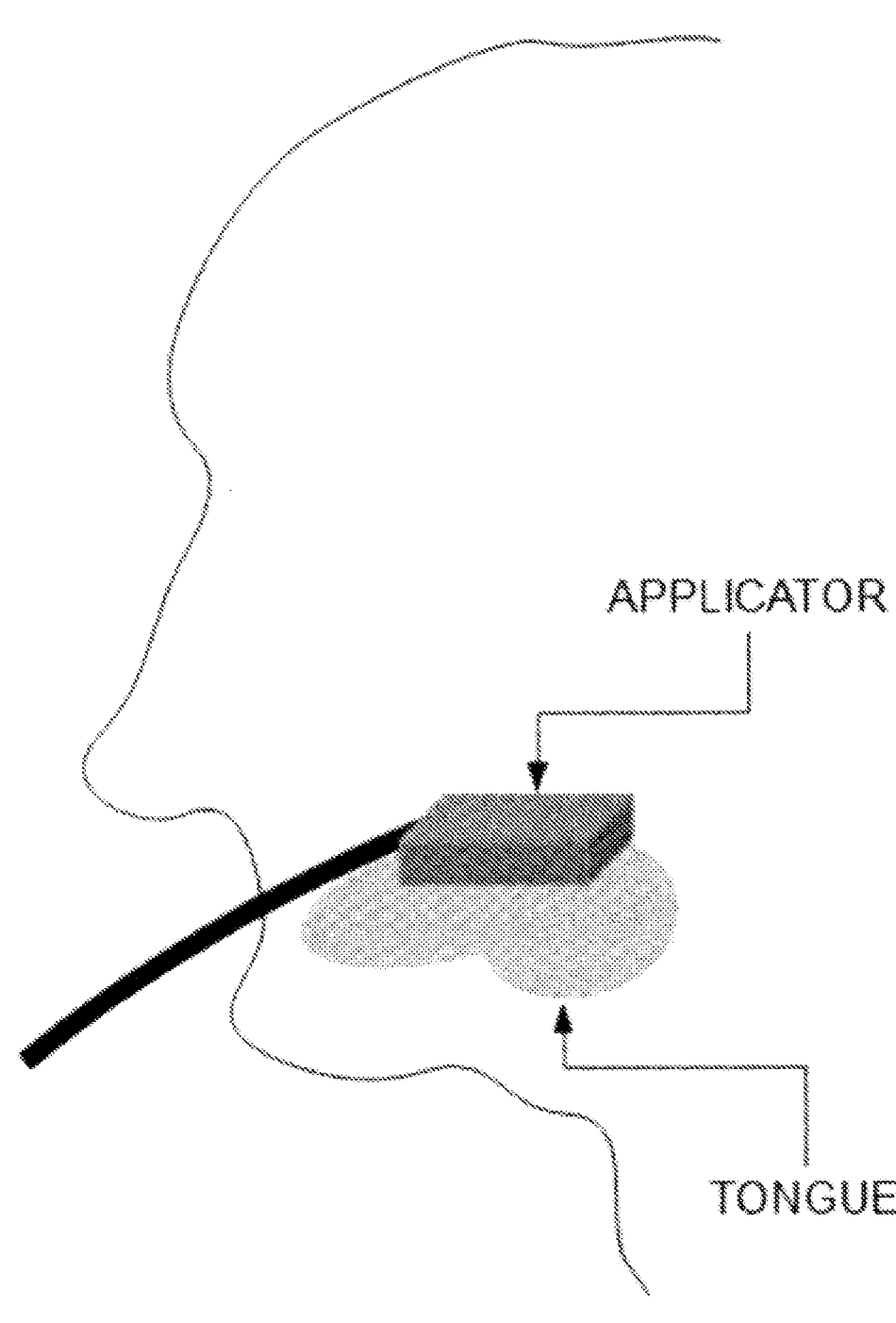
FIG. 6 shows another implementation of the applicator that is designed to be used on top of the tongue tissue.
Figure 7:
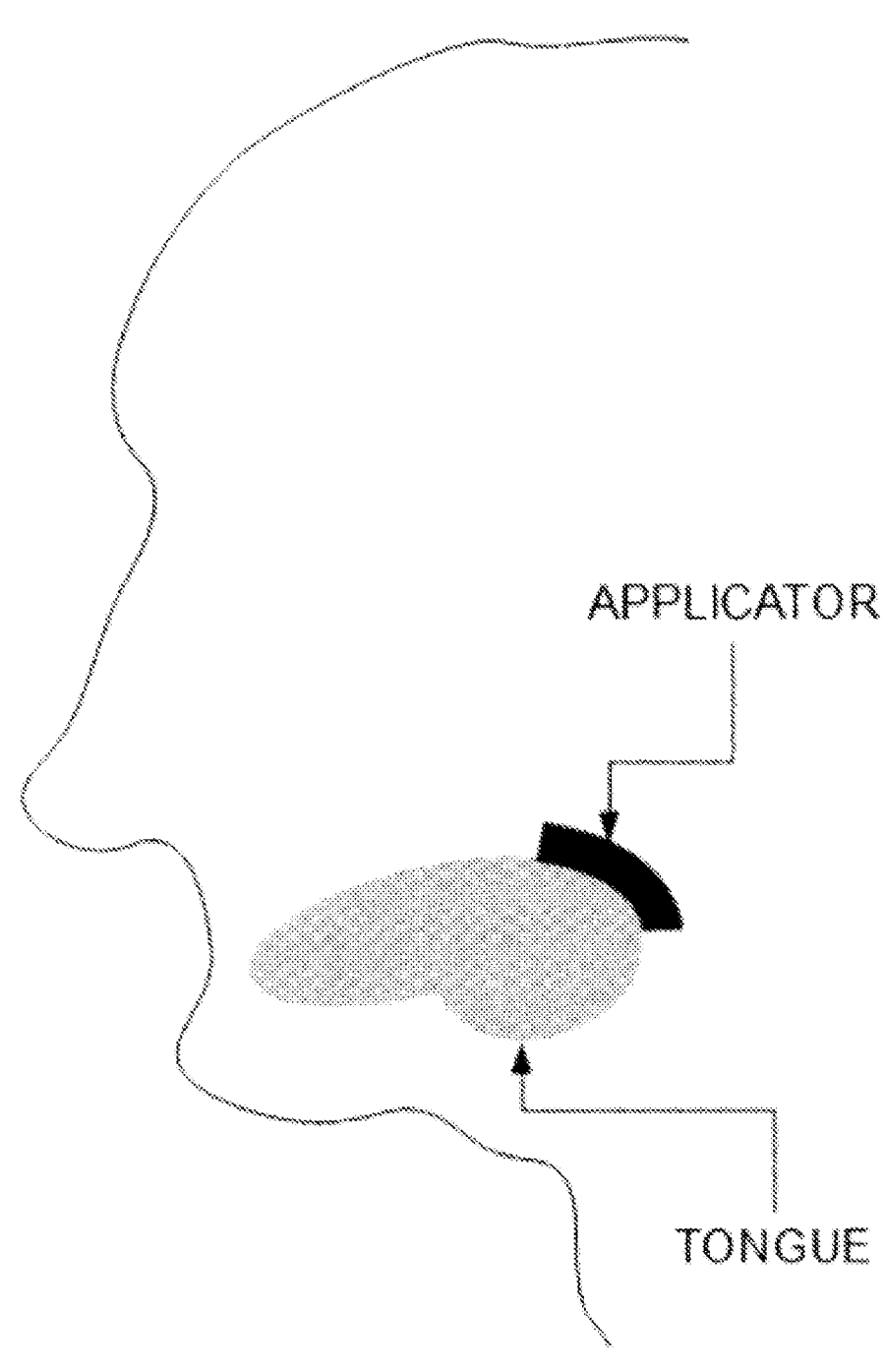
FIG. 7 shows one implementation of the applicator that is designed to reach to the back of the tongue.
Figure 8:
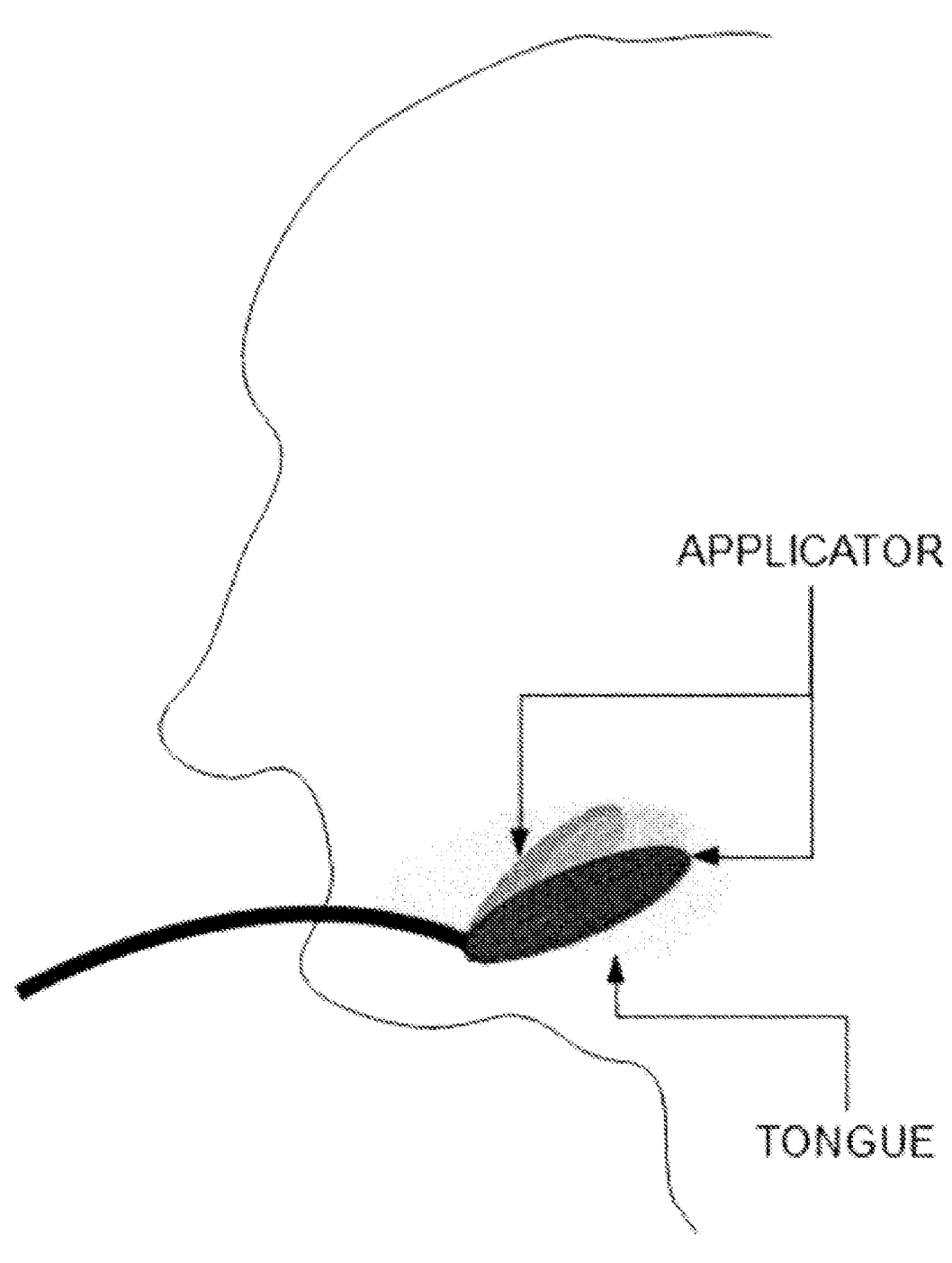
FIG. 8 shows another implementation of the applicator that is designed to extract heat from the bottom or the sides of the tongue.

The applicator may be designed to be placed on top of the tongue, on the sides of the tongue, or underneath the tongue, as shown in FIGS. 6, 7, and 8, respectively. Since the fat that is to be targeted may be located near the base of the tongue, the applicator may need to be shaped to fit to the back of the mouth as shown in FIGS. 3A-3B. Alternatively, the applicator may be designed to house the tongue by encompassing it to deliver the cold therapy from multiple directions. In some embodiments of the invention, the applicator is designed to for application to the tongue with a predetermined force or pressure. Yet in other embodiments, the applicator contains pores to apply suction to enhance the contact between the applicator and the tissue which in turns assures the conformation of the tissue to the rigid shape of the applicator.

Figure 9A:
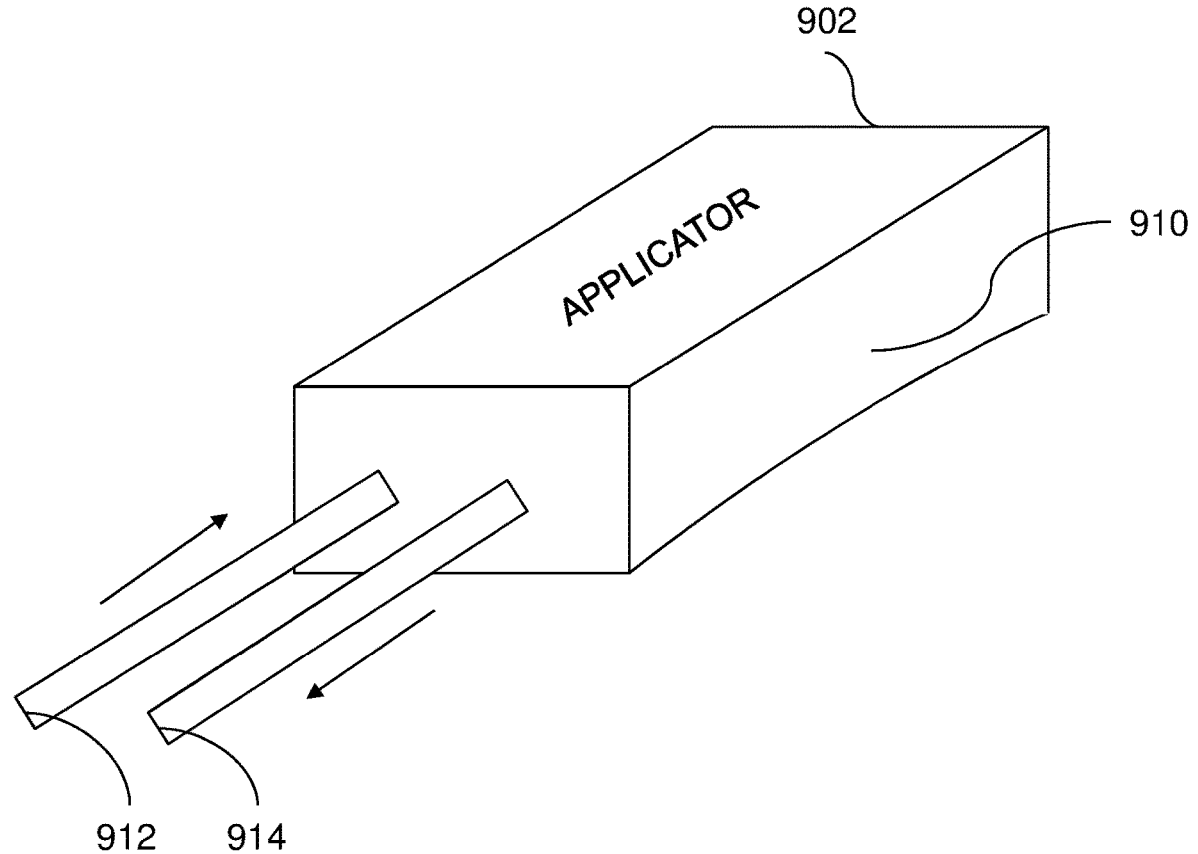
FIGS. 9A-9B depict one implementation of an applicator of the medical device that has a concave and convex cooling surface, respectively to match the tongue anatomy.
Figure 9B:
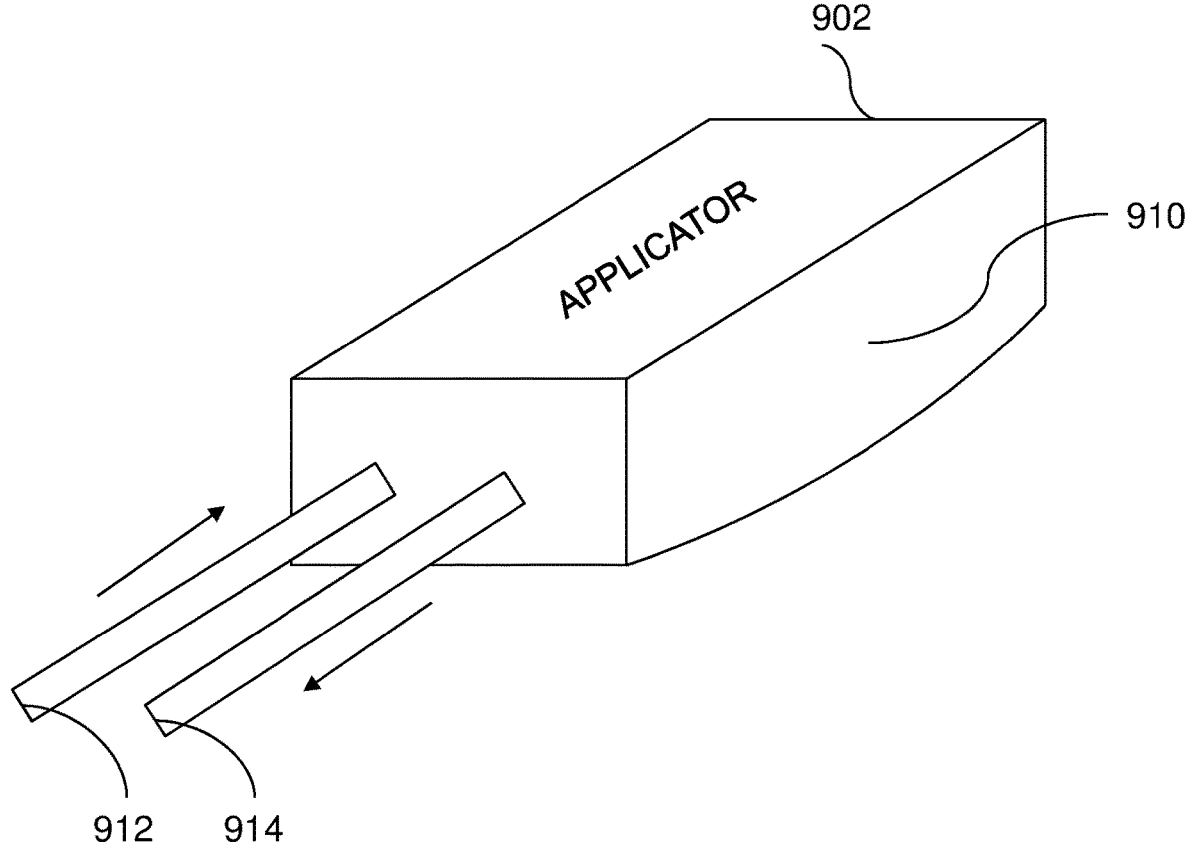

FIGS. 9A-9B illustrate various embodiments of an applicator 902 that includes a tissue contacting surface 910. The tissue contacting surface 910 can be concave, as shown in FIG. 9A, convex, as shown in FIG. 9B, or any number of other types of configurations including flat, curved, or the like. The applicator 902 can be connected to the temperature determinant of FIG. 1 via inlet line 912 and outlet line 914, which are configured to deliver coolant from the temperature determinant to the applicator and remove coolant from the applicator back to the temperature determinant.

In one example, the applicator can be shaped and configured to be inserted into the oral cavity, having a width in the range of 0.5 cm to 5 cm and length in the range of 1 cm to 8 cm. It is preferred to keep the height of the device to a minimum to allow its positioning within the oral cavity with minimal contact with the palate. Furthermore, the parts of the applicator that are not intended to be in contact with the tissue can be covered with thermal insulation to prevent thermal power loss and accidental damage to surrounding tissues. Such insulation can be constructed using, for example, ceramic or plastic materials. Furthermore, the tubing or lines carrying the coolant can also be insulated for the same purposes. Typical target temperature for the applicator is in the range of −30° C. to +40° C. preferably in the range of −20° C. to +35° C.

Figure 10A:
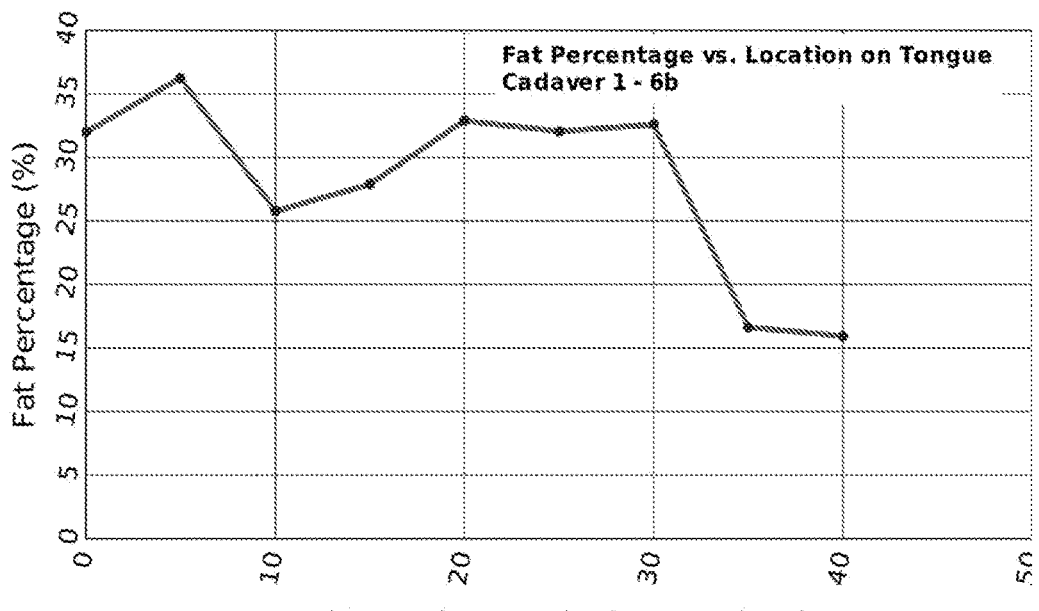
FIGS. 10A and 10B show graphs of the fat percentage of in the tissue as function of distance from the base of the tongue for human and pig, respectively.
Figure 10B:
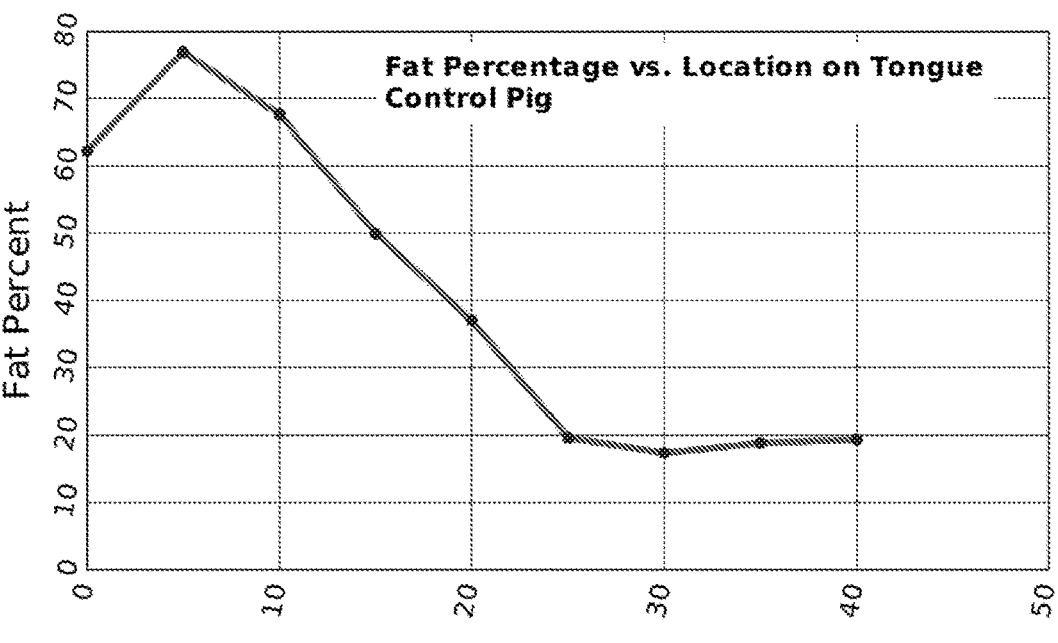

The shape of the applicator tissue contacting surface can be determined by the target tissue. For example, the target tissue may be toward the base of the tongue, in which case it may be advantageous to use an applicator with a concave surface. FIGS. 10A and 10B show graphs of the fat percentage of in the tissue as function of distance from the base of the tongue for human and pig, respectively. Given the fact that the base of the tongue has more fat and also has more volume, it is advantageous to target that area for the removal of tissue.

Figure 11A:
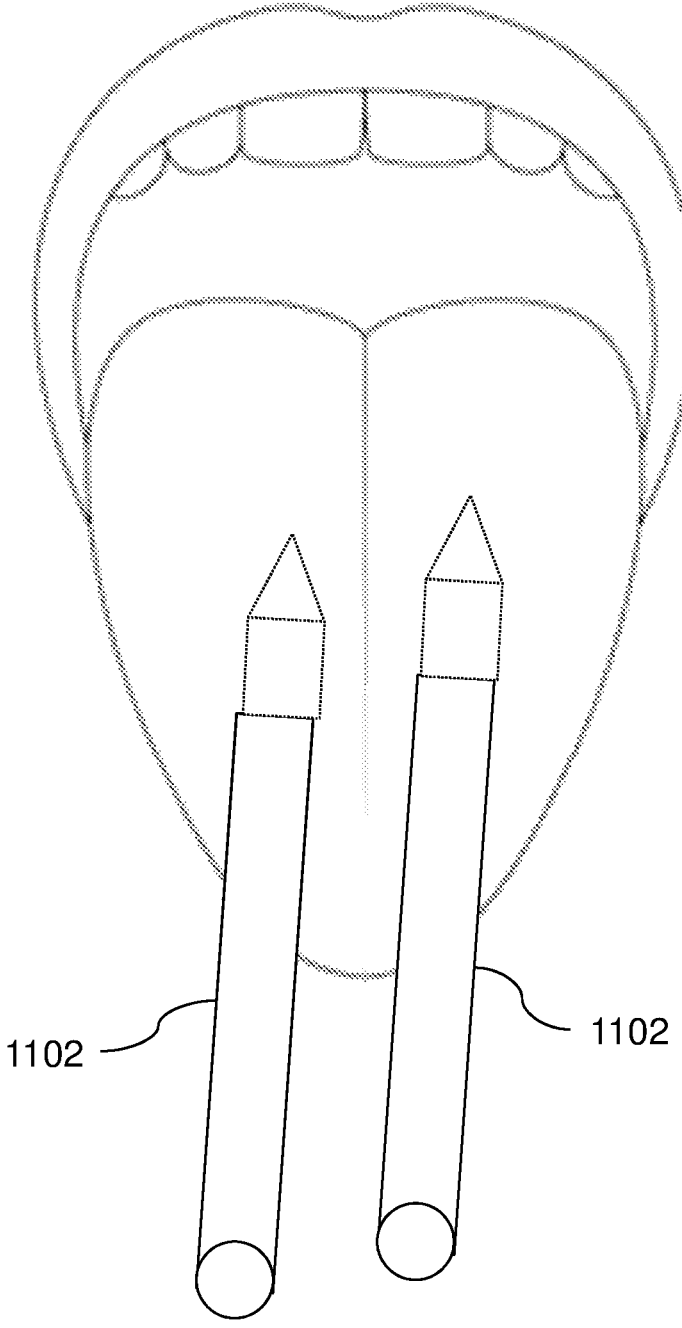
FIG. 11A depicts an implementation of the medical device in which the applicators penetrate into the tongue tissue from the dorsal surface of the tongue.
Figure 11B:
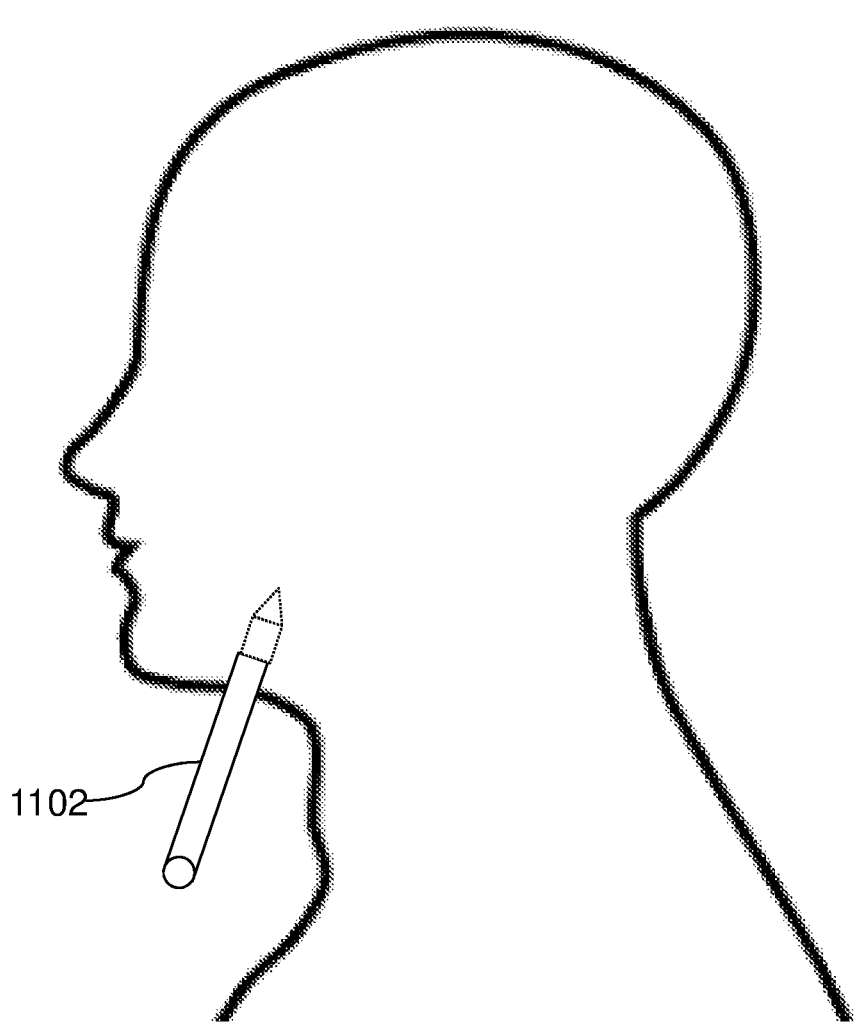
FIG. 11B shows an implementation of the medical device in which probes penetrate through the submaxillary triangle into the lower tongue tissue.

Some patients may have the anatomical features that may make it difficult to treat them using the applicators that are placed on the dorsal surface of the tongue. In that case, it may be necessary to use applicators that penetrate into the tissue. FIG. 11A illustrates an example of one or more penetrating applicators 1102 configured to enter the tongue tissue from the dorsal surface to provide therapy to the target tissue. In one embodiment, the penetrating applicators can include vacuum sealed insulated shafts and an active region for a specified length at the tip of the penetrating applicator. In one example, a chilled nitrogen gas can be pre-cooled with liquid nitrogen to cool the tip. In other embodiments a Joule Thompson gas expansion cooling technique could be used where the gas is allowed to expand at the tip. Since the penetrating applicators are likely to be thin to reduce the trauma to tissue, high capacity heat removal techniques must be employed. Furthermore, they must have the strength to remain rigid during insertion. Their active cooling region may not extend along their axial length, but may be limited to a portion on the distal end of the device. In this example, the penetrating applicators 1102 can be connected to other components of a sleep apnea treatment system as described above, including a temperature determinant, a controller, and lines for delivering coolant from the temperature determinant to the applicator(s). FIG. 11B illustrates one embodiment where the penetrating applicator 1102 is configured to enter into the low tongue tissue underneath the chin of the patient through the submaxillary triangle. In one example, the penetrating applicator can have a diameter of approximately 2 mm and an active cooling length of approximately 30 mm.

Figure 12C:
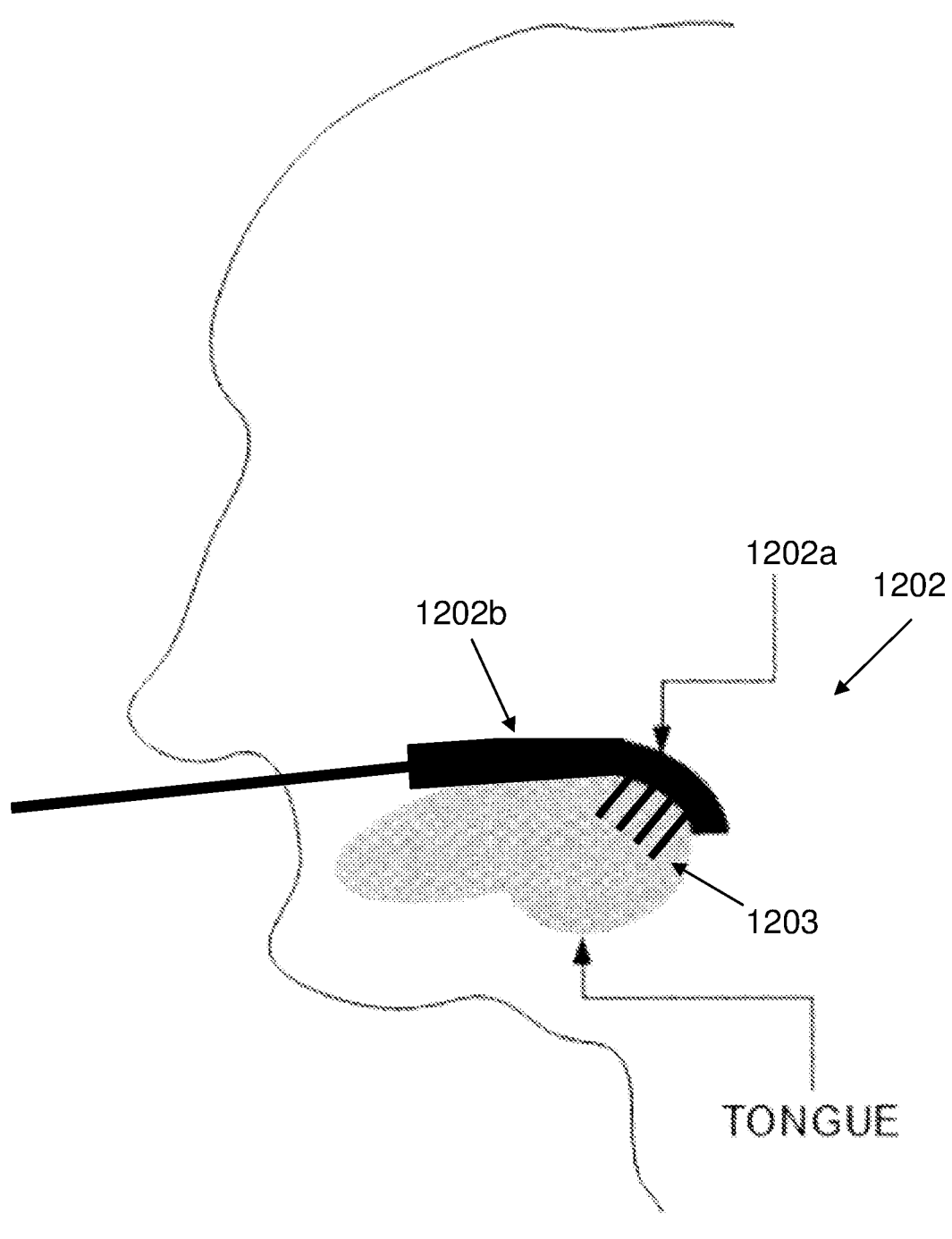

Embodiments of a penetrating applicator 1202 are shown in FIGS. 12A-12C, where FIG. 12A illustrates an applicator with multiple penetrating components 1203 that are designed to be planar while FIG. 12B shows a tissue penetrating applicator design that is three dimensional with a plurality of penetrating components 1203. For example, referring to the embodiment of FIG. 12C, the applicator 1202 may include therapy prongs or penetrating components 1203 oriented on a distal portion 1202a of the applicator and configured to be inserted into the back of the tongue, and a proximal portion 1202b with or without penetrating components configured to be placed upon some or all of the remaining portion of the tongue. It should be understood that each of the distal and proximal portions of the applicator 1202 can be flat or curved. Therefore, both distal and proximal portions of the applicator can be curved, both can be flat, the distal portion can be curved and the proximal portion can be flat, or vice versa.

A tissue penetrating applicator may remove heat from the tissue by conduction.

Using Equation 1, one can calculate the conductive heat that is removed by a 3 cm long copper pin with a radius of 1 mm as 2.39 Watts, if the tissue is at 37° C. and the base of the applicators shown in FIGS. 12A-12C are at −20° C. If the average heat to be removed from the tissue is P=50 Watts, then a design with N=21 rods is needed. Such a device can be constructed as 3 rows of 7 pins attached to a base, using the design that is shown in FIG. 12B. Since the average power to be extracted is about 5 Watts for most applications, it may be possible to use fewer pins.

A tissue penetrating applicator may remove heat from the tissue by convection. In that case, the penetrating pin can be constructed as a double barrel or concentric pipes. Fluid flow through a cylindrical pipe is given by the Hagen-Poiscuille equation which is:

$$\phi = \frac{(\Delta P)\pi D^4}{128\ \mu L}. \qquad \text{Equation 3}$$

where φ is the fluid flow rate,
ΔP pressure differential between the two ends of the pipe,
D is the inner diameter of the pipe,
μ is the dynamic viscosity of the fluid, and
L is the length of the pipe.

Using Equation 3, one can calculate the flow rate of a fluid with viscosity of 0.89 cP in a 3 cm long pipe with a diameter of 0.5 mm and pressure differential of 1 Atmosphere as 5.74 mL/sec. If the coolant has a specific heat of c=4 Joules/(cc.° C.) is used and the temperature drop across the is ΔT=2° C., then the heat that is being extracted from the tissue by a single pin can be calculated as P=45.9 Watts using the Equation 2.

One specific example of an applicator system will now be described. The applicator system 1300 shown in FIG. 13 includes an applicator 1302 connected to a two stage heat extractor 1304. Stage 1 of the heat extractor can comprise a compressor (e.g., condenser type) that is configured to produce a coolant at the temperature of 0° C. while the stage 2 of the heat extractor can comprise thermoelectric type configured to reduce the temperature of the coolant to a range of −10° C. to −20° C. The two stages of the heat extractor can be thermally coupled with a peltier booster. Each stage of the heat extractor can include its own fluid pump configured to pump coolant fluid through the circuits. In some embodiments, both stages of the heat extractor can be closed loop fluid circuits.

Figure 13:
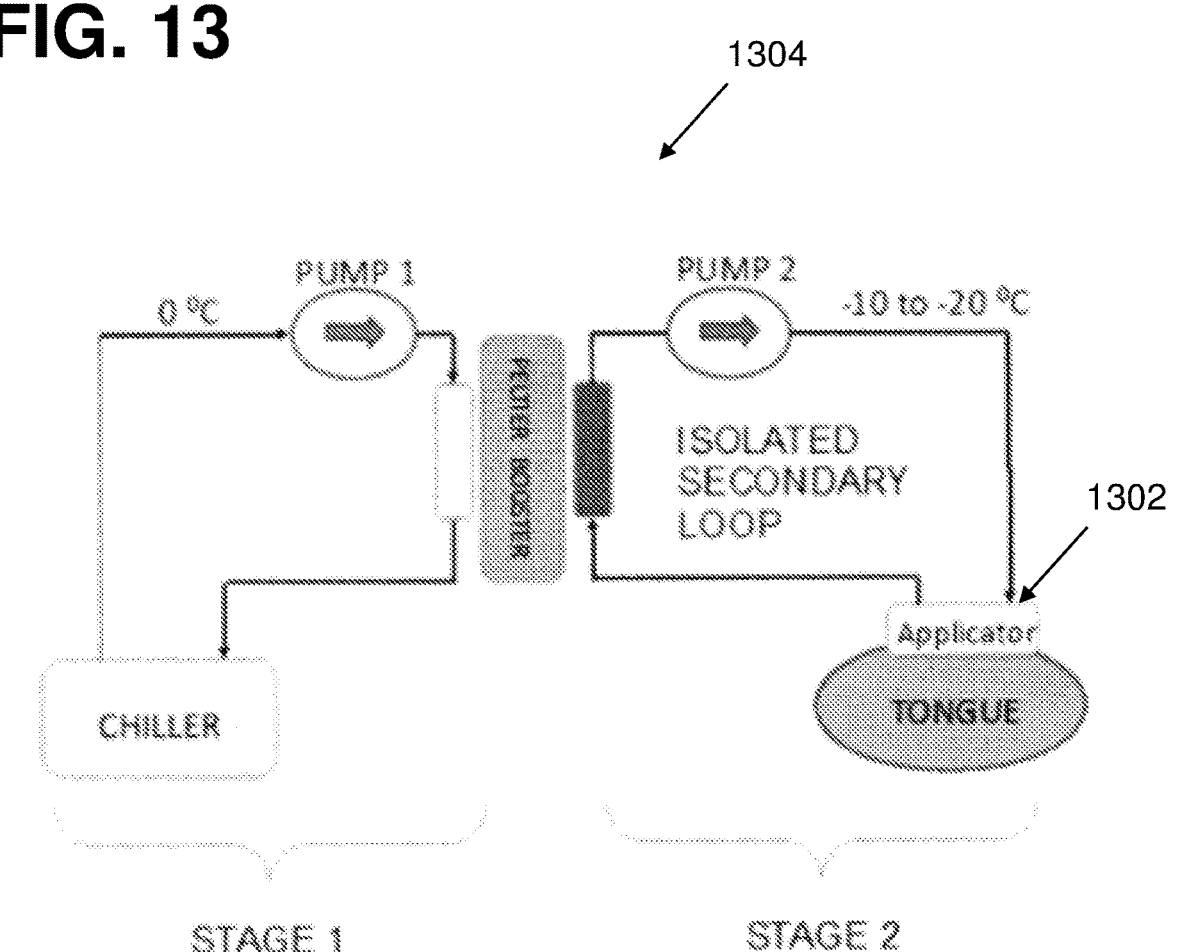
FIG. 13 shows another example of an implementation of a two stage heat extractor with isolated secondary circuit.
Figure 14:
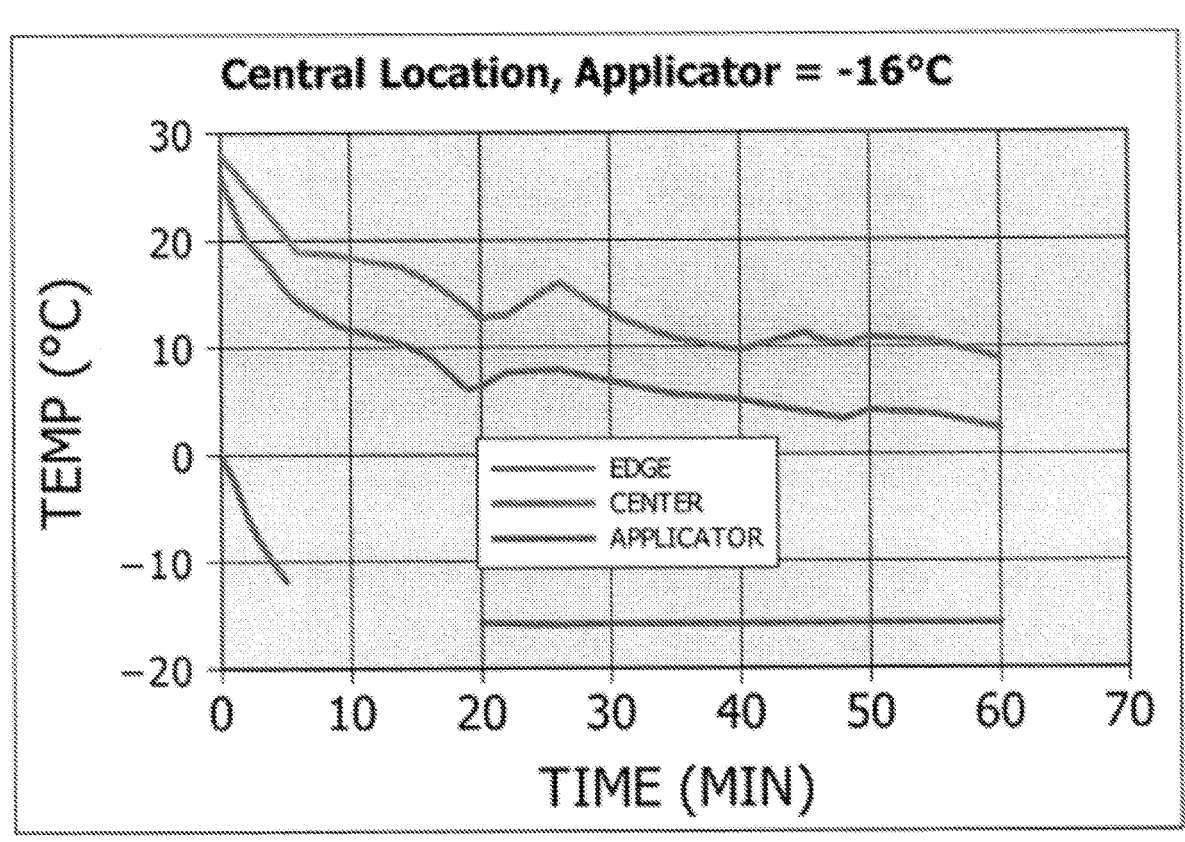
FIG. 14 shows some resulting temperature profiles of the applicator and the tissue underneath the applicator when the applicator is brought to −16° C.

In a lab trial using the system of FIG. 13, an applicator was placed on the tongue of a 6 month old pig and kept in place for 60 minutes while monitoring the temperature of the tissue under the applicator at two different locations. During the first trial, the applicator temperature was −11° C. During the second trial, the applicator temperature was −16° C. and the resulting tissue temperatures are shown in FIG. 14. After 3 hours, animal was sacrificed and the tongue was removed and examined following Hematoxylin and Eosin (H&E) and Masson's trichrome staining. Temperature measurements done in the tissue were in agreement with the computer simulations that were carried out using a theoretical model indicating that the device was functioning as designed and was providing the cooling of the tissue. Furthermore, the trichrome stained tissues showed the expected alterations in the morphology of the cells. Observations resulting from the pathological examination of the tissue indicate that the mucosal lining was preserved. Tissue that is up to 5 mm below the surface showed the effects of the cryo-procedure where the deeper tissues appear to be unaffected.

Cryoprotectant can be applied to tissue with the applicator for the preservation of mucosal layers. The cryoprotectant can be, for example, propylene glycol, glycerin, fructose, sucrose (for example) or other agents that can be safely used for the reduction of the damage to tissues during freezing, or could be a combination of these cryoprotective agents. These agents are configured to prevent the formation of large ice crystals, which results in cell damage and necrosis or apoptosis. The protection of the mucosal layer is important to reduce or eliminate the side effects from the delivery of cold temperatures. Preservation of nerves and surface glands is desirable. The cryo applicator is also required to deliver very cold temperatures at the surface of the treatment area in order to create therapeutic cryo temperatures deep into the tissue. The top 0.1 to 5 mm of tissues and muscle may also be protected from this extreme cold as the cryoprotectants diffuse into the tissue. A time delay of 1, 5, 10 or 30 minutes may be desirable in order to achieve this perfusion and protection. Salt ions may be added to the cryoprotectant to increase perfusion and equilibration into the tissues. The cryoprotectant may be formulated as a gel with adequate viscosity to prevent migration and flow of the cryoprotectant away from the treatment zone. Cryoprotectant may also be applied to the vallecula, soft palate, epiglottis, gums, cheeks or any other oral structures that may come in contact the cryo probe or tubing or mounting apparatus of the cryo system.

Some embodiments of the applicator are configured to maintain the presence of cryoprotectants, such as propylene glycol, glycerin, sucrose and fructose and their combinations. Cryoprotectants can be used for the reduction of the freeze damage to the tissues, especially those that are in the immediate vicinity of the applicator. They also improve the thermal coupling between the applicator and the target issue. In some embodiments, the applicator may carry the cryoprotectant agents on its surface, or may store it for release during the treatment process.

The applicator may also be configured to preflush the oral cavity with cold fluids before the onset of the treatment session. The surface of the applicator may have dimples or recesses or ridges which capture and maintain cryoprotectant gels or fluids to maintain the cryoprotectant at the surface of the tongue. The pores can be configured to store and release/deliver cryoprotectants during therapy. Furthermore, having some space for a volume of cryoprotectant between the tongue and applicator allows for the cryoprotectant to absorb excess water, saliva, or moisture from the surface of the tongue. Water moisture can freeze causing damage to the tongue. Cryoprotectants with hydrophilic properties aid in the absorption of water. Cryoprotectant may be pumped in via ports or holes on the bottom of the applicator to replenish the cryoprotectant during the procedure, which may last 1 to 100 minutes.

Penetrating probe designs can be inserted mid-line along the frenulum. The tongue innervation and vascular structures are minimal in the midline. The target adipose tissue is accessible via a probe inserted through the midline. Slight lateral deviations from midline area are also safe. The position of the surgical probe can be tracked via an ultrasound probe, applied either via the dorsal tongue surface or by the placement of an ultrasound probe under the chin. The applicator probe could be inserted 25%, 50%, 90% or 110% with respect to the base of the tongue. The applicator probe may be allowed to penetrate the base of the tongue (110% penetration) to register exact positioning. An umbrella or hook may release upon exiting the base of tongue allowing the physician to then snuggly pull the probe forward, locking it in the position for the duration of the treatment. The distal hook can be released by cutting the distal tip or using a higher force to pull the applicator probe out. The applicator probe can also be inserted into the tissue from the top surface of the tongue, preferably near the midline to avoid damaging the nervous innervation and the existing vasculature, and angling toward the base of tongue. The surgically inserted probe can apply the cryo therapy to a cylinder shaped region of the tongue. Multiple sticks of the applicator probe can treat a larger area, or multiple applicator probes can be inserted simultaneously, which in turn will cool the tissue that is in between the applicator probes. The applicator probe can also be advanced or retracted in 1 cm steps, for example, to step-wise treat a longer length of tissue. Another approach is to insert two or more probes simultaneously that are approximately parallel, either lateral to each other or superior/inferior. Such tools are designed to target deeper tissues in the ventral surface of the tongue, specifically between a line drawn from the mandible to the base. As a result, the penetrating parts of the applicator may be straight or curved to reach to the locations where the fat is concentrated.

Figure 15A:
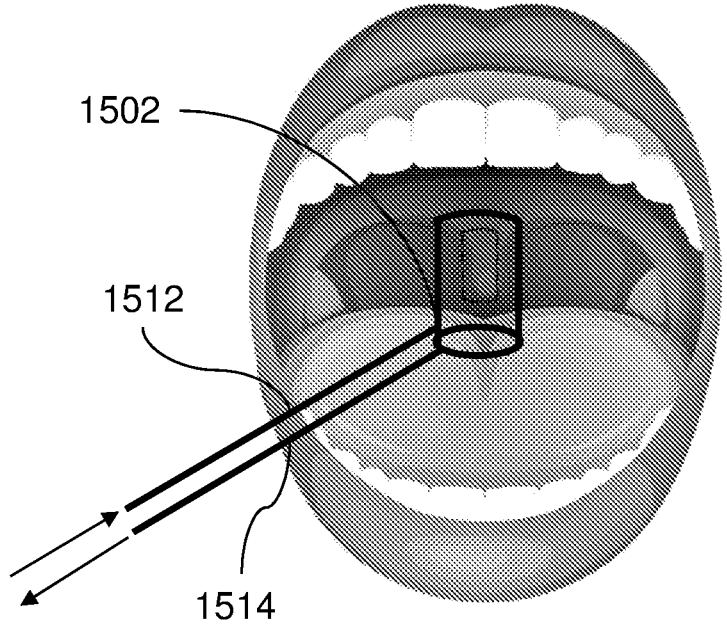
FIG. 15A depicts one implementation of a cylindrical device configured to house and cool the uvula during treatment.

Additional target tissues in the oral cavity can be targeted for treatment, including the tissues of uvula and the lateral fat pads in the oral cavity. FIG. 15A illustrates one example of a cylindrical applicator 1502 specifically designed and configured to target the fat tissue in the uvula. In this embodiment, the applicator can be cylindrical in shape and can include a hollow portion within the cylinder configured to receive the uvula when the applicator is placed over the uvula. Inlet line 1512 and outlet line 1514 can transfer coolant between the temperature determinant and the applicator during therapy. The human uvula is an irregular triangle shaped tissue. The size (estimate) ranges from 3 mm at the tip of uvula widening to 2 cm as the uvula joins the soft palate. Although the inside of the cylindrical applicator can be hollow to allow the capture of the uvula within, its bottom end can be closed in some embodiments to increase the contact area with the uvula for better heat extraction. Furthermore, suction maybe applied to enhance the physical contact between the cylinder and the tissue.

Figure 15B:
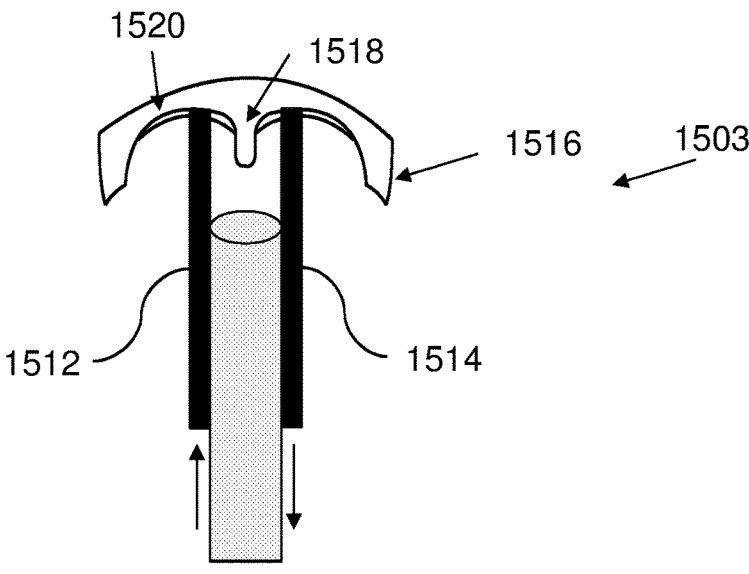
FIG. 15B illustrates one embodiment in which the applicator is "M" shaped to cool the uvula, tonsils, and fat pads.
Figure 15C:
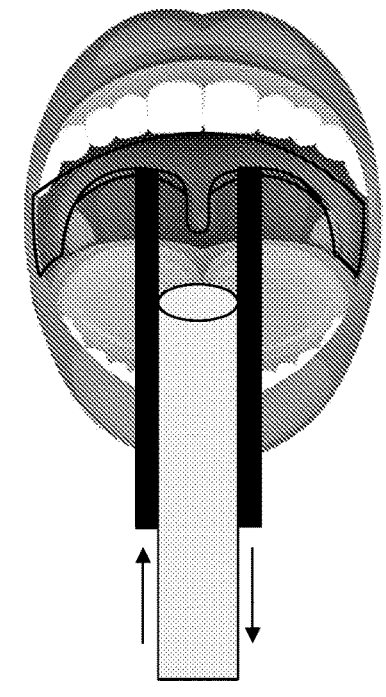
FIG. 15C shows a method of applying the "M" shaped applicator to the oral tissue to cool of the uvula, tonsils, and the fat pads.
Figure 16:
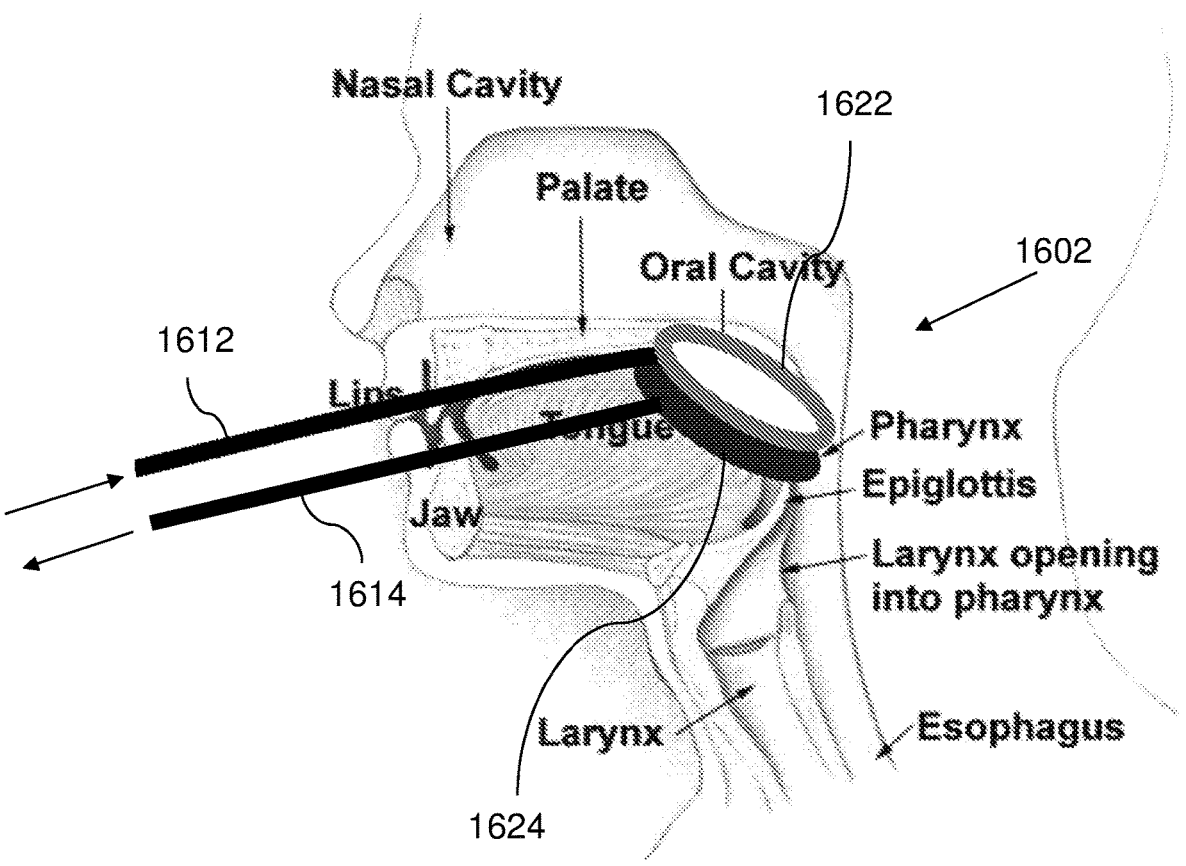
FIG. 16 shows an implementation of a balloon cryoablation applicator configured to cool multiple organs such as the tongue, palate, uvula, and tonsils.

FIGS. 15B-15C illustrate another embodiment of an applicator 1503 configured to simultaneously target, cool, and treat the uvula, tonsils, and fat pads of the oral cavity. In this embodiment, the applicator can include a pair of tonsil contacting extensions 1516 on each side of the applicator to directly cool the tonsils. Additionally, the applicator includes a uvula contacting portion 1518 centrally located on the applicator. The uvula contacting portion can be, for example, a solid cylinder, a hollow cylinder (as shown in FIG. 15A), or any other flat or curved shape configured to contact or conform to the uvula. The connecting member portions 1520 between the uvula contacting portion and the tonsil contacting extensions can be configured to contact and cool fat pads within the oral cavity at the back of the mouth. As described above, inlet line 1512 and outlet line 1514 can transfer coolant between the applicator and the temperature determinant. FIG. 15C shows the applicator 1503 positioned in the oral cavity such that the tonsil contacting extensions are in contact with the tonsils, the uvula contacting portion is in contact with the uvula, and the connecting member portions are in contact with fat pads in the mouth.

In some examples, the applicator is designed and configured to be in a pliable form such as a balloon, so that it confirms to the shape of the target tissue. When in place, first the pressure unit is inflated to position the applicator within the oral cavity. Afterwards, the cooling unit of the balloon can be filled with a warm coolant to inflate and make contact with the organ. Once a full contact with the target organ is made, the coolant temperature can be reduced to extract heat from the organ. A multi-balloon applicator system is also desirable in that one (or multiple balloons) balloon could serve the pressure unit for holding the system in place and a second (or multiple balloons) balloon could apply cryo therapy to the target location(s).

FIGS. 16-18 and 19A-19B show examples of applicators that are designed and configured to target more of the tissues in the back of the mouth, including the lateral walls and the fat pads. For example, the embodiment of FIG. 16 includes a balloon applicator 1602 configured to cool multiple organs in the oral cavity, including the tongue, palate, uvula, and tonsils. The balloon applicator can include one or more inflatable structures 1622 and 1624. In this example, inflatable structure 1622 can be insulated so as to prevent cooling tissue in contact with the structure, while structure 1624 has no insulation and can be allowed to cool and treat tissue. In another embodiment, the balloon applicator is a single inflatable structure (e.g., only structure 1624). In one embodiment, the balloon applicator can be inserted into the oral cavity in a deflated state, and advanced to the target tissues. Once in position, the balloon applicator can be inflated with a coolant to treat the target tissues. Coolant can be transferred between the balloon applicator and the temperature determinant (not shown) via inlet line 1612 and outlet line 1614, as described above.

Thermocouples can be mounted on the surface of the balloons using thermocouple wires and or flex circuits printed on the balloons. Thermocouples can measure the temperature at the target site to ensure an efficacious therapy and good tissue contact. Thermocouples on the pressure unit balloon(s) can protect surrounding tissues from cryo damage. Other sensors such as pressure sensors and optical sensors can be used to monitor balloon pressure and tissue contact. Electrodes can be placed on the balloons via printed circuits. These electrodes can be used to measure impedance on the surface of the tongue to verify adequate contact with the tissue. Multiple measurement points can be used to verify contact across the intended contact and treatment area. The balloon can be inflated until full contact with the target area is achieved, as measured by the impedance or pressure measurements. Contact with the tongue can also be determined by the temperature sensors warm when in direct contact with the tongue or target tissue. Electrodes to measure impedance, thermocouples, or pressure sensors can also be applied to non-balloon applicator designs, for the similar purpose of verifying and measuring contact with the intended treatment area. Other temperature sensing devices, including but not limited to RTD (resistive temperature devices), solid state temperature sensors or optical temperature sensors can be used in addition or instead of the thermocouples.

Figure 17:
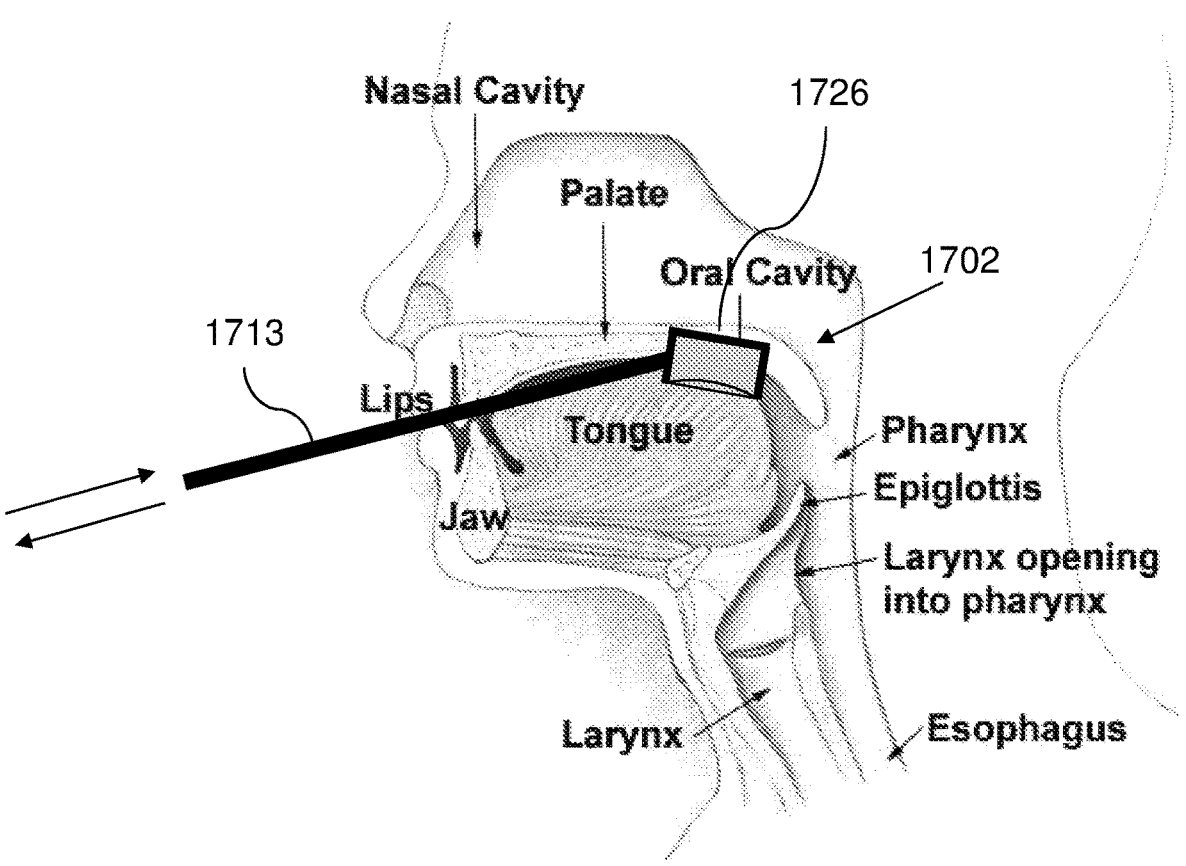
FIG. 17 illustrates the design of an applicator in which all sides are insulated except for the bottom of the device.
Figure 18:
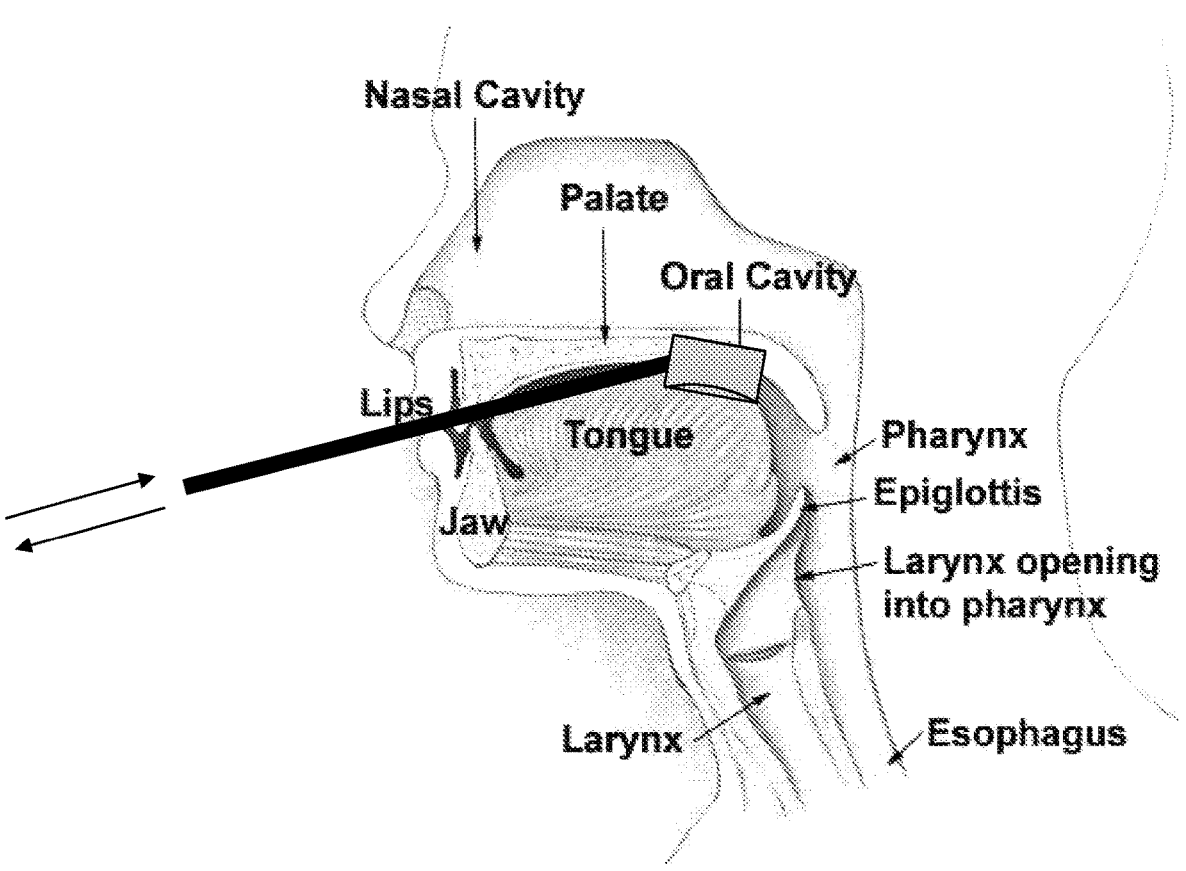
FIG. 18 shows the design of an applicator in which no sides of the device are insulated.

FIG. 17 is another example of an applicator 1702 configured to target tissues towards the back of the mouth. The applicator 1702 can include insulation 1726 on one or more surfaces of the applicator. In this example, the applicator is not insulated on the surface that contacts the tongue, but is insulated on all other surfaces, including the surface that contacts the palate, the checks, the epiglottis, etc. The insulation is designed and configured to protect tissues in the oral cavity that are not being targeted for cryo therapy. As described above, inlet/outlet lines 1713 (shown as a single line in this example) can facilitate the transfer of coolant to and from the applicator for therapy. In contrast, the applicator of FIG. 18 does not include any insulation on the applicator.

Figure 19A:
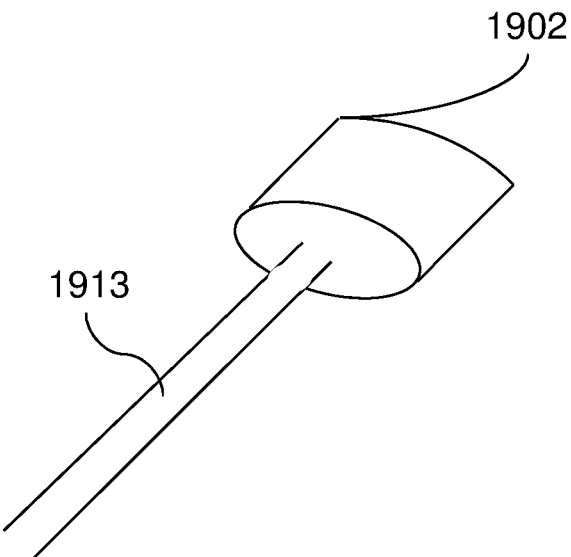
FIG. 19A is another embodiment of an applicator that can be pushed against the lateral wall in order to cool the fat pads.
Figure 19B:
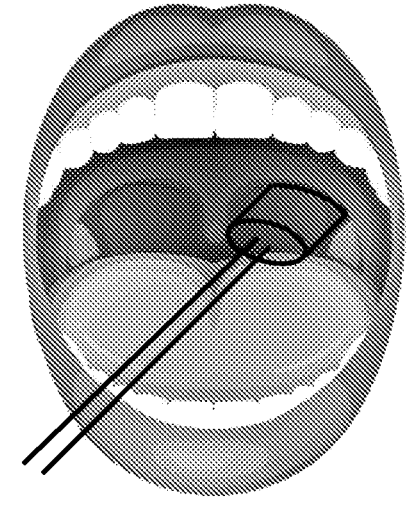
FIG. 19B shows a method of applying the applicator of FIG. 19A to the lateral wall in order to cool the fat pads.

FIG. 19A is one example of another applicator 1902 configured to apply cooling therapy to a lateral wall in the oral cavity so as to treat the fat pads. The applicator itself can be a metallic object, preferably stainless steel, aluminum, titanium. It is also possible to construct it using thin plastics with high thermal conductivity, such as the ultra-high molecular weight polyethylene. Since the tissue that the applicator is pressed against is a soft one, the applicator can be a rigid structure. However, one can use a balloon type applicator also to enhance the contact with the tissue and to reduce the sensitivity of the treatment to the positioning of the applicator. As shown, the applicator 1902 can include a distal portion sized and configured to contact the fat pads. The distal portion can be generally cylindrical in shape. In some embodiments, the distal portion can be pliable in order to conform to the fat pads when placed in contact with the fat pads. Coolant can be transferred to/from the applicator with an inlet/outlet line 1913, as described above. FIG. 19B illustrates a method of applying the applicator 1902 of FIG. 19A to the lateral wall to col the fat pads.

The applicator can be designed to be pushed onto the tissue surface with a given pressure. The design may maintain the force or the pressure within a given range, or it can be such that the application pressure or the force meets a minimum. Application of the force or the pressure assures a good contact with the tissue while minimizing the convective heating of the tissue by the warm blood arriving from the other parts of the body of the patient. The force needs to be equal to or greater than the arterial blood pressure to minimize the arrival of new blood flow to the treatment area to reduce the convective heating of the tissue. Maintenance of the force could be via mechanical elements such as springs, or electrical elements such as actuators, and may involve passive or active control of the applied force. A balloon structure could also be used to provide a controlled force to the applicator, by inflating the balloon between the hard or soft palate and the applicator, or similarly, by placing force between the posterior oropharynx wall and the applicator or between the upper teeth and the applicator. A push against the hard pallet, soft pallet, teeth, or posterior oropharynx could be used separately or in combination to provide an opposition force that holds the applicator in correct position with the correct pressure on the tongue.

Figure 20:
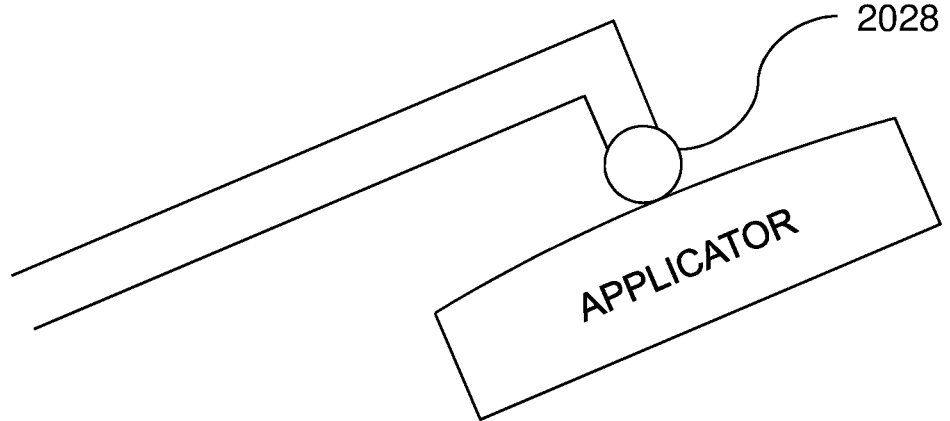
FIG. 20 depicts one embodiment of a handle attached to the applicator by a ball and socket joint to increase the conformity of the applicator to the tongue tissue.
Figure 21:
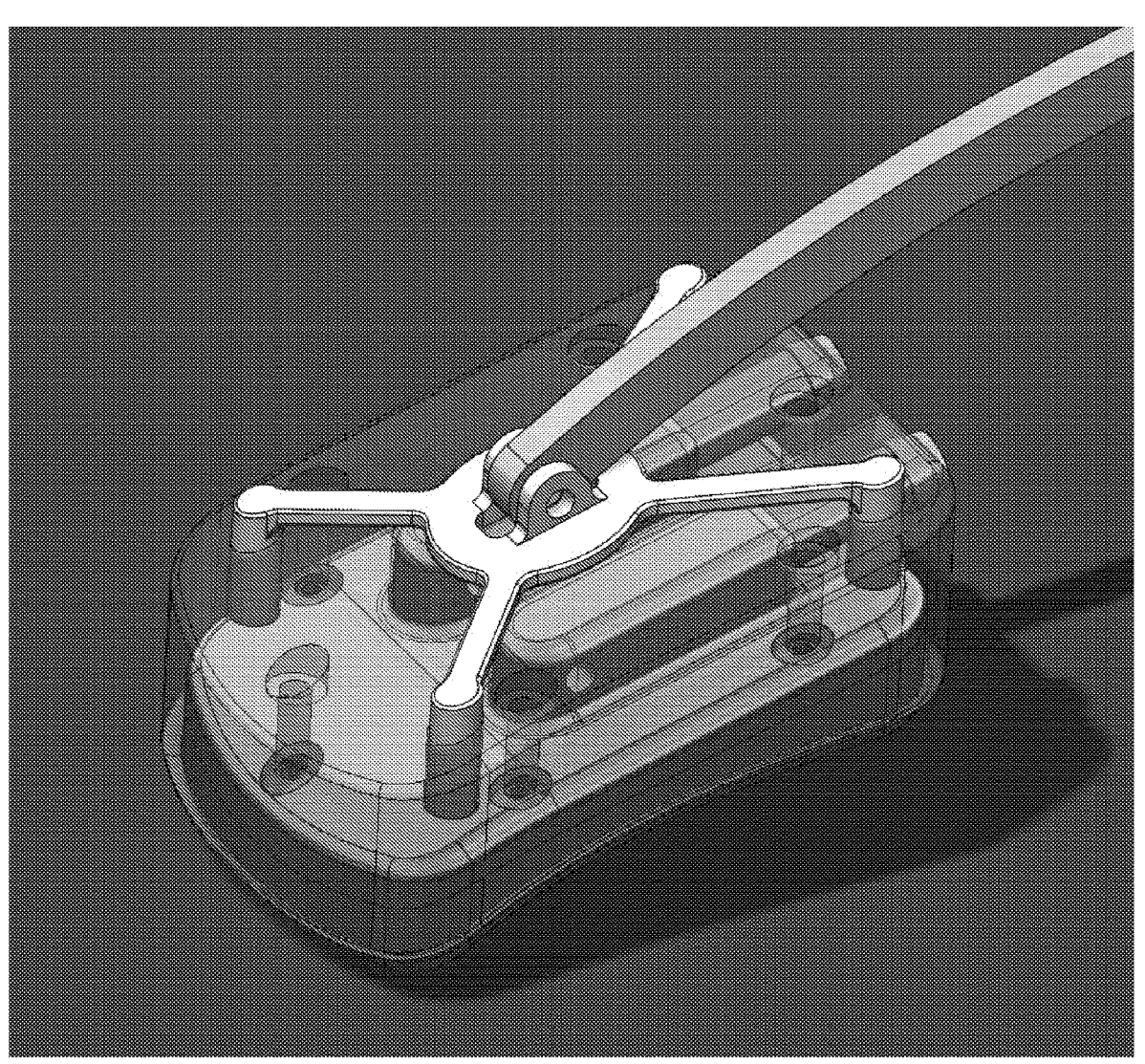
FIG. 21 is one example of an applicator that has an ability to pivot around its push arm while accommodating multiple sensors for the measurement of application pressure and surface temperatures.
Figure 22:
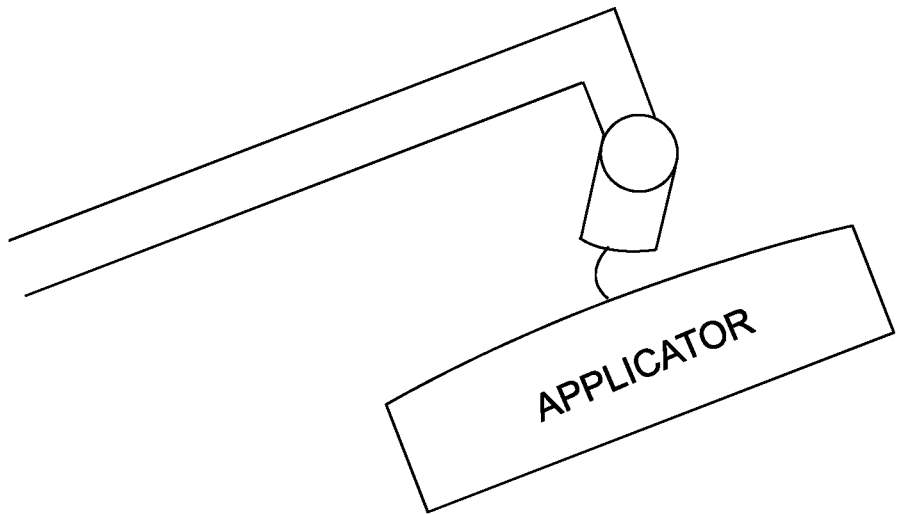
FIG. 22 is another embodiment of a handle attached to the applicator by a motorized ball joint in order to manipulate the application of the device to the tongue tissue.

To ensure a good contact between the applicator and the tissue surface, one of many design modifications can be utilized. FIGS. 20-22 show embodiments in which the applicator is configured to pivot around a joint that attaches the applicator to a handle. This joint can be, for example, a multi axis joint such as a ball and socket joint as it is illustrated in FIG. 20, or a single axis rotary joint as shown in FIG. 21. In some embodiments, the joint may also be a motorized joint, such as the one that is shown in FIG. 22 to allow the correct positioning of the applicator at the desired orientation to obtain the optimal contact profile between the tissue and the applicator surface.

Figure 23:
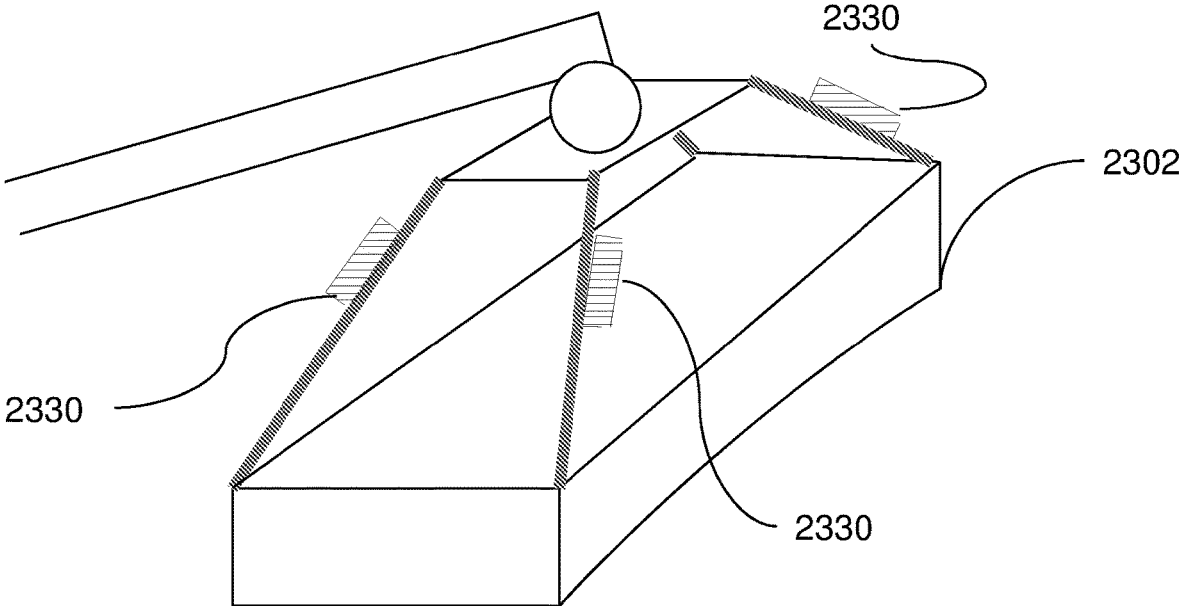
FIG. 23 is an example of an applicator with one or more force sensors.
Figure 24A:
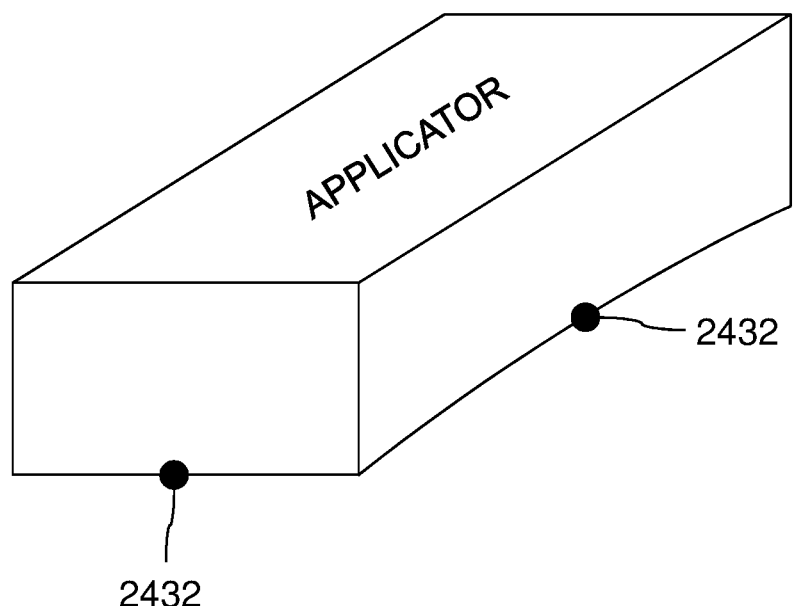
FIG. 24A illustrates an applicator with one or more temperature sensors on the face of the applicator to measure surface temperatures.
Figure 24B:
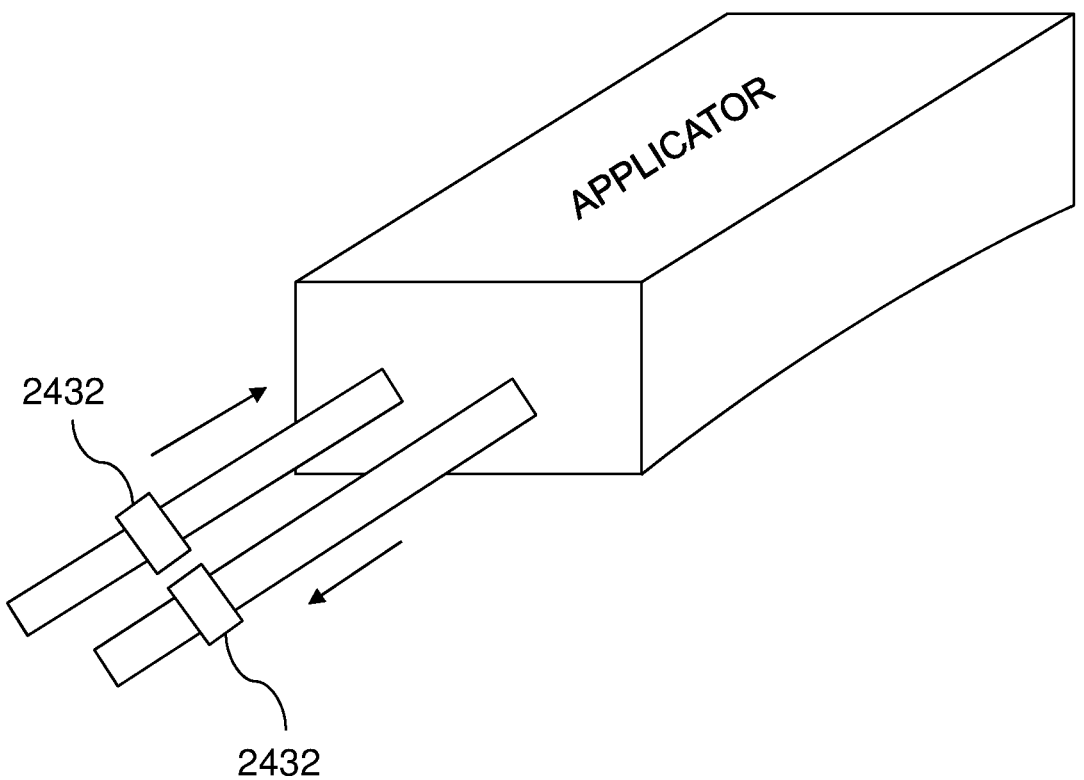
FIG. 24B depicts an applicator with multiple temperature sensors attached to inlet and outlet fluid lines to measure absolute temperature of the coolant as well as the temperature differential between coolant in the outlet and inlet fluid lines.

Deviations from the desired force and temperature ranges can be detected using a set of sensors, such as temperature sensors and strain gauges. FIG. 23 shows the implementation of an applicator 2302 with a plurality of force sensors 2330 disposed on the applicator. In this example, the force sensors are positioned towards each corner of the applicator. The force sensors can be used to determine or identify if the appropriate force is being applied by the applicator to the target tissue. Furthermore, the force sensors can be configured to determine if an un-even force is being applied to the target tissue. For example, if one or more force sensors on a first side of the applicator measure a different force than one or more force sensors on an opposite side of the applicator, then the operator or user knows to re-adjust the applicator to apply an even force across the entirety of the target tissue. Similarly, temperature sensors 2432 can be positioned at the bottom surface of the applicator, as shown in FIG. 24A, and on the fluid lines, as shown in FIG. 24B. The temperature sensors can be used to determine if various sections of the target tissue are being cooled to the desired temperature. The temperature sensors can further provide measurements of the temperature of the applicator itself. In some embodiments, methods can include applying an applicator to a target tissue, delivering cryo therapy from the applicator to the target tissue, measuring a temperature of the target tissue at one or more locations within the target tissue, and adjusting a position of the applicator based on the measured temperatures.

Heat removed or delivered by a fluid flow system is given by:

$$P = \phi \Delta T C \qquad \text{(Equation 4)}$$

Where P is the thermal power in Watts,
$\Phi$ is the coolant flow rate,
$\Delta T$ is the temperature rise in the coolant, and
C is the specific heat of the coolant If a coolant with a specific heat of c=4 Joules/(cc.° C.) is used with a flow rate of q=15 mL/sec and the temperature drop across the is $\Delta T$=2° C., then the heat that is being extracted from or added to the tissue can be calculated as P=120 Watts using the Equation 4. However, to determine the amount of heat being added or removed, one must know the temperature differential, namely $\Delta T$. This can be accomplished by measuring the temperatures of the inlet and outlet fluids, as shown in FIG. 25B.

Figure 25:
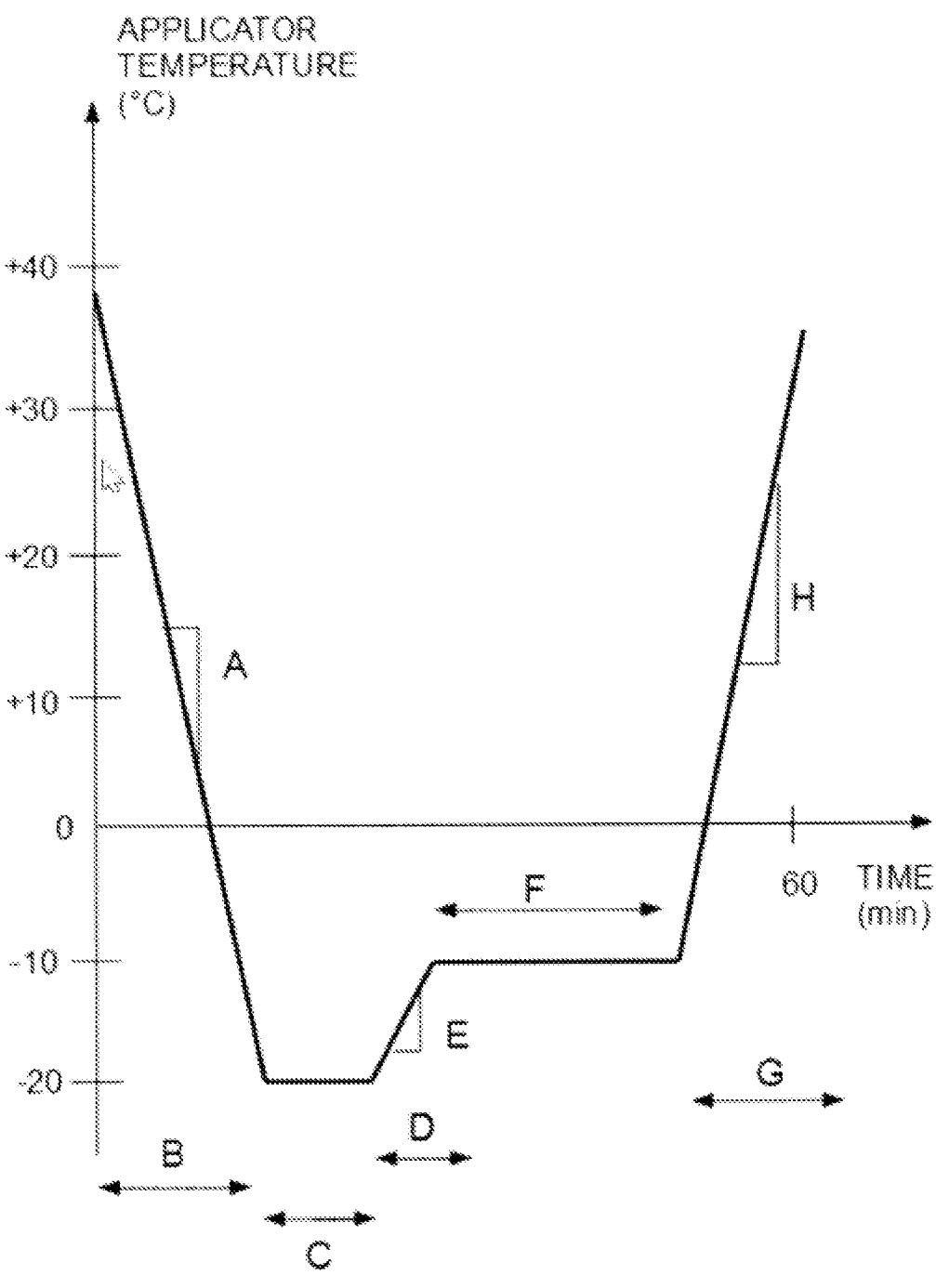
FIG. 25 shows another exemplary format for the temporal variation in the temperature of the applicator where the temperature is cycled between cold and warm.

FIG. 25 shows an exemplary temperature trace of the applicator for a treatment duration of 60 minutes. In this example, the temperature of the applicator is dropped at a rate of A degrees per minute for the period of B. Afterwards, the applicator temperature is kept at a cold temperature for a duration of C for the removal of substantial amount of stored heat from the tissue. Subsequently, the applicator temperature is allowed to raise at a rate of E degrees per minute for a period of D and maintained at a fixed temperature for a period of F. Finally, the applicator temperature is allowed to increase at a rate of H degrees per minute for a period of G to conclude the treatment session.

Figure 26:
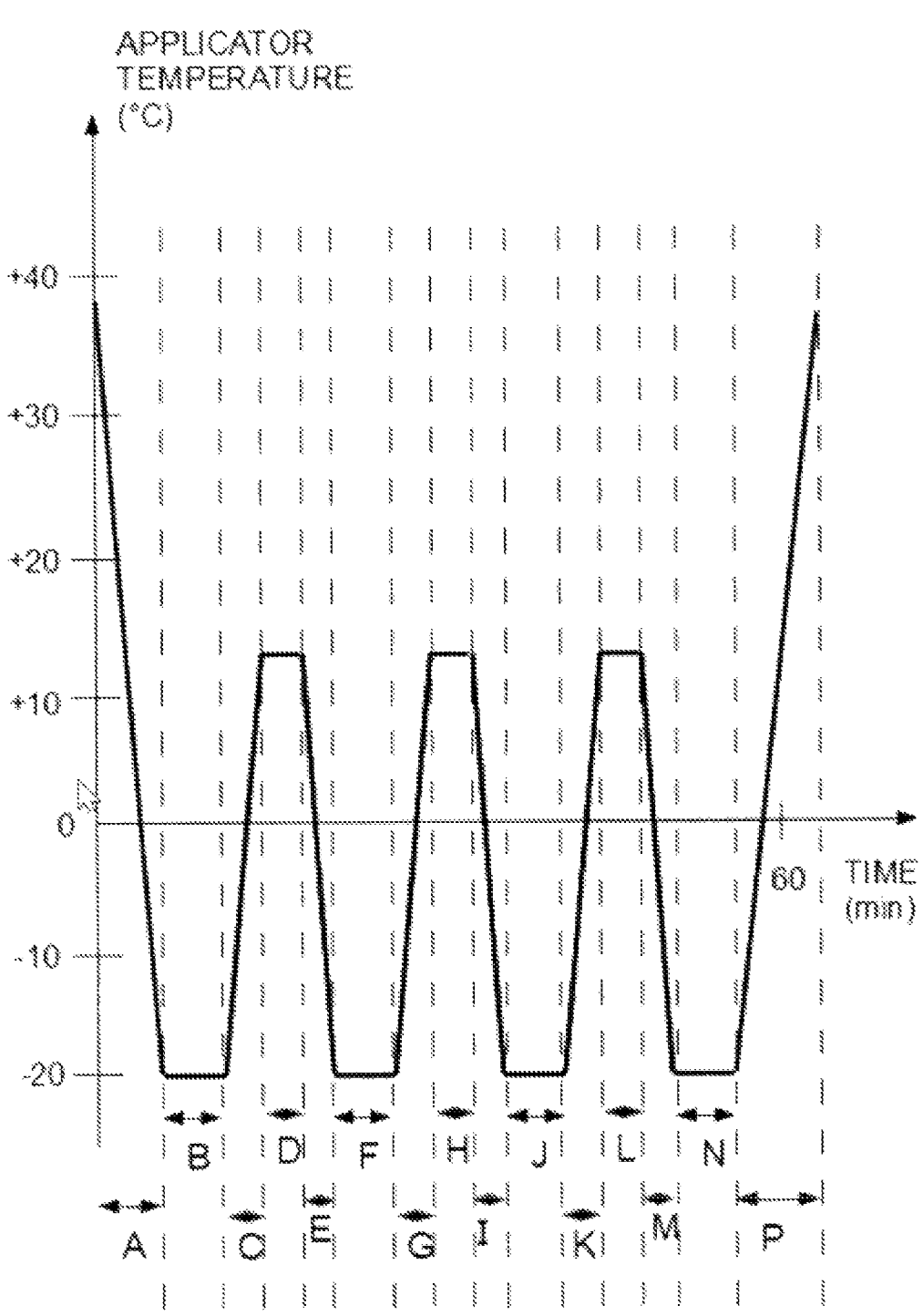
FIG. 26 shows another time profile of the applicator temperature which is cycled between a cold and warm setting throughout the treatment duration.

FIG. 26 shows another time profile of the applicator temperature which is cycled between a cold and warm setting throughout the treatment duration. Cycle lengths, duration at each stage and the rate of change in temperature setting can be the same for each cycle or vary from one cycle to the next. This type of treatment could be advantageous as temperature transitions further enhance the effects of the cryolysis.

Figure 27:
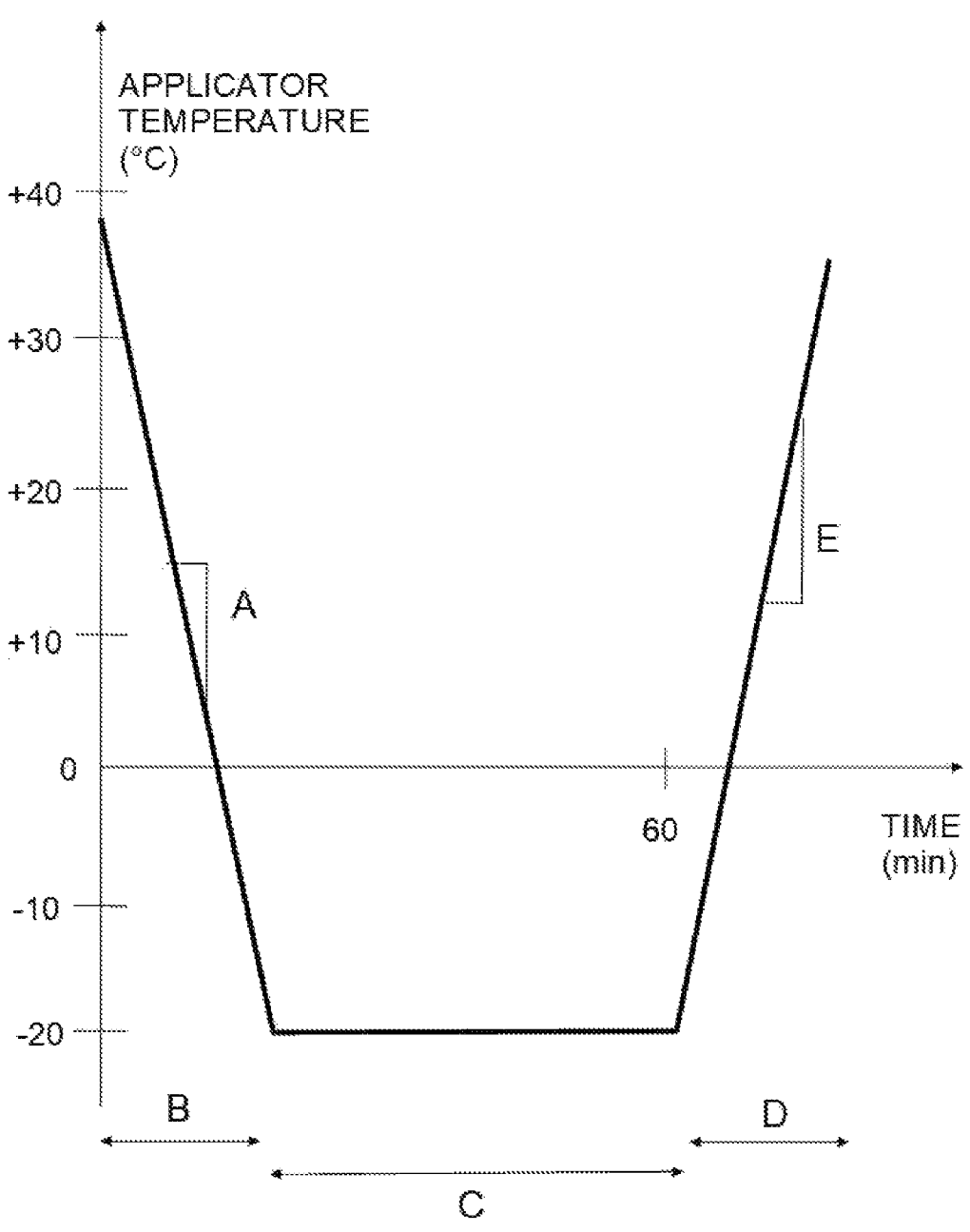
FIG. 27 illustrates a graph of applicator temperature as function of time, according to one implementation.

Cryolysis of the adipocytes is accomplished by reducing their temperature to values in the range of +5° C. to −20° C., and more specifically to the range of 0° C. to −5° C. To achieve such temperatures at the depths of the tissue, one must bring the applicator to temperatures in the range of −15° C. to −30° C., or perhaps lower. Such temperatures could cause damage to the mucosal membranes of the tongue, especially to the mucosal layers that are near the base of the tongue. Such damage can be prevented by the rapid warming of the tissue at the end of the treatment period. FIG. 27 shows an idealized version of the applicator temperature as a function of time. During the period that is labeled as "D", rapid warming is needed. The warming rate, which is labeled as "E" in FIG. 27 should be higher than 10° C./min, preferably 10° C./min to 30° C./min.

Figure 28:
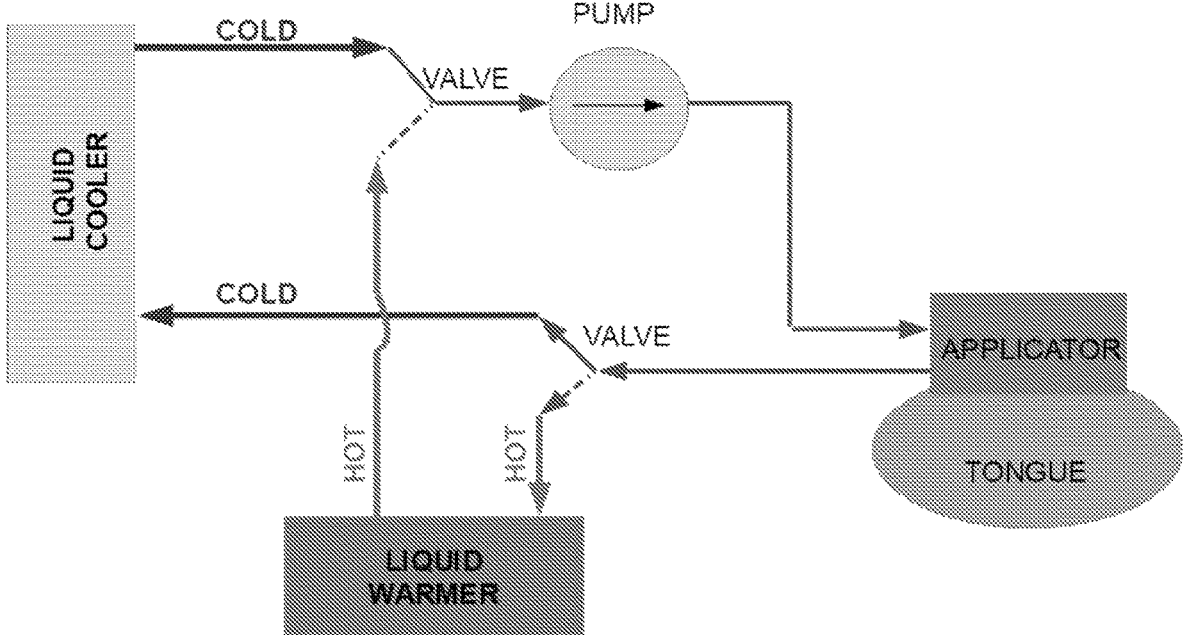
FIG. 28 shows the implementation of a temperature determinant where both a chiller and a heater are utilized.

To implement the rapid warming function as described above, the temperature determinant must be able to provide both the heating and the cooling functions. FIG. 28 shows the implementation of a temperature determinant where both a chiller and a heater are utilized. A pair of valves can be used to select the source where the fluid travels through, that is the heater or the chiller. During the phases that are labeled as B and C in FIG. 27, the chiller can be used to reduce the temperature of the fluid that is being sent to the applicator, which in turn removes heat from the tissue causing cryolysis. During the phase that is labeled as D in FIG. 27, fluid can be cycled through the heater to rapidly warm the applicator and the mucosal membrane to reduce the unintentional damage.

The heat extractor is the part of the system that provides the low temperature operation which in turn enables heat extraction from the tissue. The heat extractor can be an integral part of the applicator, such as a thermoelectric cooler residing within the applicator or a Joule-Thompson type cooler. But in general, the heat extractor is located external to the applicator. Chilled coolant is pumped from the heat extractor to the applicator.

Figure 29:
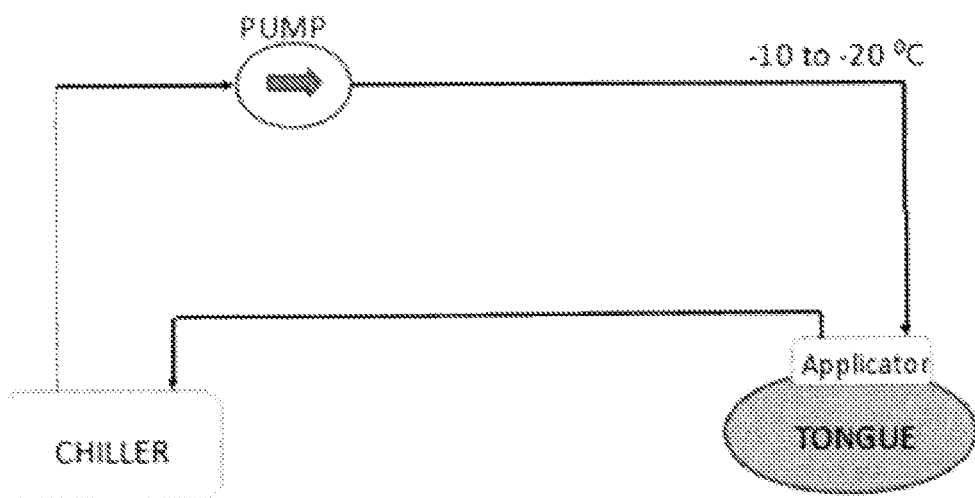
FIG. 29 shows another implementation of a single stage heat extractor.
Figure 30:
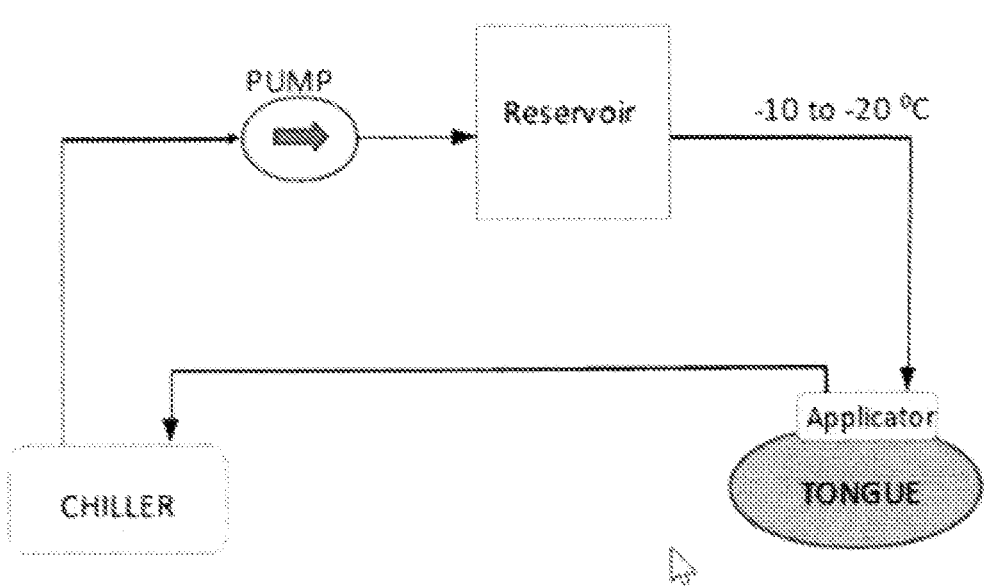
FIG. 30 shows one possible implementation of a single stage heat extractor with a coolant reservoir.

The heat extractor may include one or more stages. If the heat extractor is a single stage device, as shown in FIG. 29, then the chilled fluid is delivered directly to the applicator from the chiller/heat extractor via a pump. FIG. 30 shows a single stage heat extractor unit where a reservoir is used to store the pre-chilled coolant. The presence of the reservoir reduces the power requirements for the chiller and allows a rapid cooling of the tissue.

In the case of multi stage heat extractor, as shown in FIG. 13, multiple heat extractors are stacked to increase the cooling capacity and the overall control of the cooling of the tissue. Multi stage heat extractors can be isolated or non-isolated type, and they can have reservoirs also. FIG. 13 shows the block diagram of a two stage heat extractor with isolated secondary loop and no reservoir. The first stage can include a chiller, a first pump to move fluid through the first stage, and a first heat exchange surface adjacent to a peltier booster. The second isolated stage can include a second heat exchange surface adjacent to the peltier booster and a second pump to move fluid into the applicator.

Figure 31:
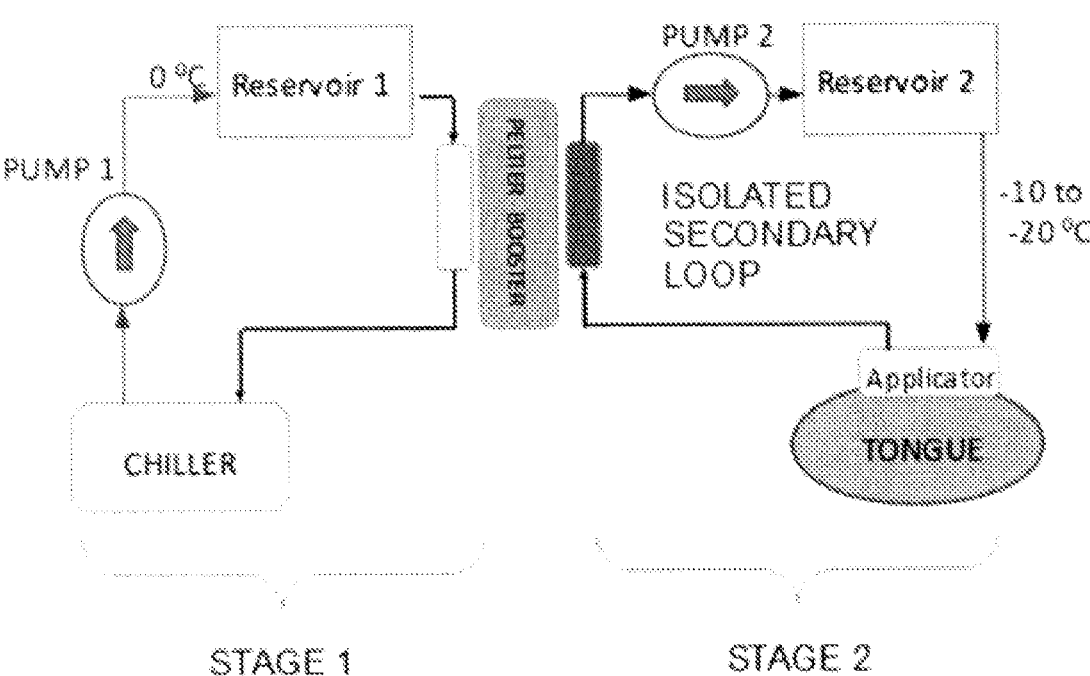
FIG. 31 shows another example of an implementation of a two stage heat extractor with isolated secondary circuit.

FIG. 31 shows the block diagram of a two stage heat extractor with isolated secondary loop and two reservoirs. The design of the heat extractor in this embodiment is similar to that of FIG. 13, however each stage includes a reservoir to store chilled fluid.

Figure 32:
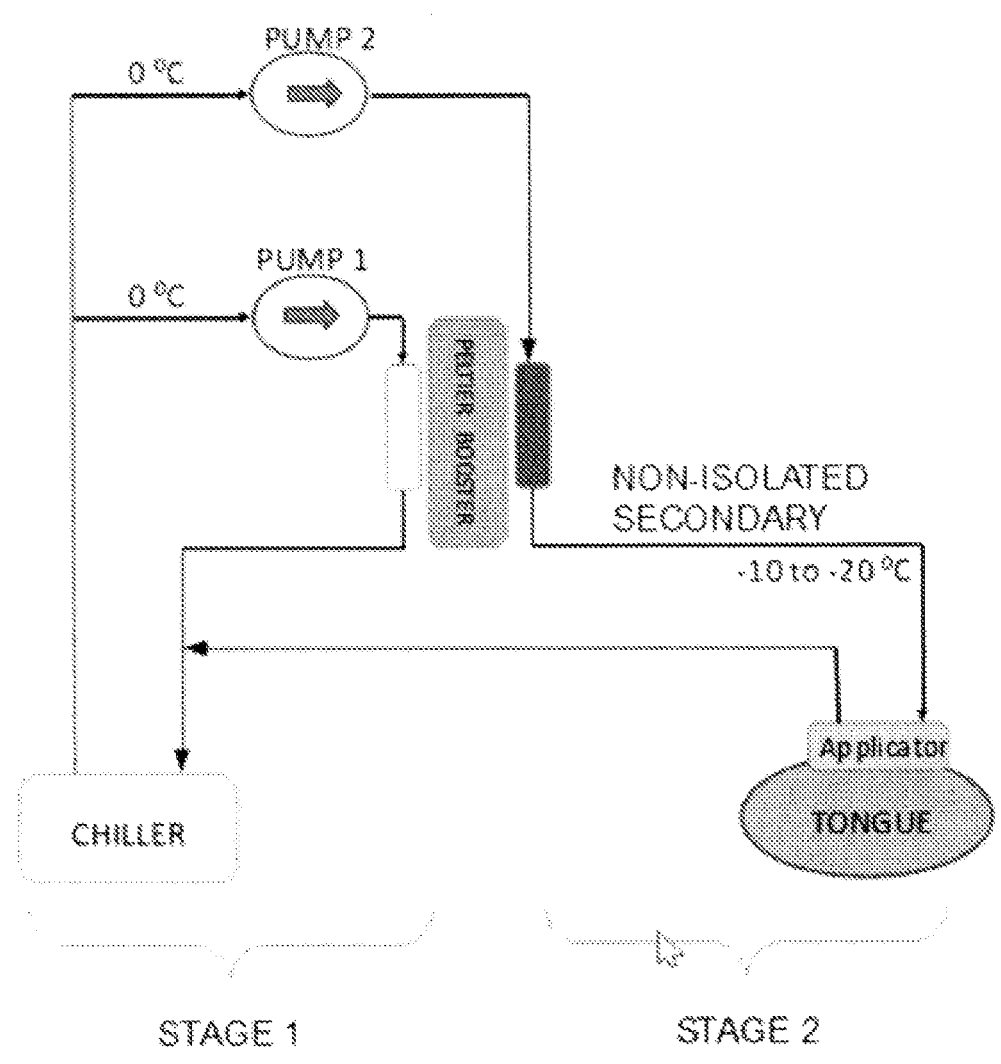
FIG. 32 shows one implementation of a two stage heat extractor with isolated secondary circuit and two coolant reservoirs.

FIG. 32 shows the block diagram of a two stage heat extractor with non-isolated secondary loop and no reservoirs. In isolated multi stage heat extractors, the coolants used in different stages do not mix while a non-isolated multi-stage heat extractor uses the same coolant for all stages. Heat extractors with non-isolated secondary loop have higher ability to cool warm tissues, but they are not as efficient when it comes to lowering of the temperature of cold tissues. On the other hand, the heat extractors with isolated secondary loop are not very good at cooling warm tissues, but they are highly efficient at further lowering of the temperature of tissues that are already cold. Hence, some implementations combine these two designs, where the heat extractor is configured as a non-isolated secondary during the beginning of the treatment session and then switched, via solenoid or manual valves, for example, to the isolated secondary configuration afterwards. Coolant used could be a gas or a fluid type.

The heat extractor can utilize one or more of the traditional cooling techniques, including the compressor-condensers, Joule-Thompson devices, phase change devices and thermoelectric coolers (TEC) which are also known as Peltier coolers. A booster unit can be used in a multi stage heat extractor, utilizing Peltier coolers. The booster unit consists of one or more Peltier devices that work as heat pumps to remove heat from the cold side and pass this heat to the hot side of the Peltiers. The chiller unit described above serves to cool the hot side of the Peltier devices. The cold side of the Peltier devices is used to chill an isolated secondary loop of coolant that extracts heat from the applicator on the tongue. The Peltier devices could also be directly applied to tongue tissue.

A fluid pump carries fluid across the hot side through a heat exchanger region in the booster. Likewise, a second fluid pump carries fluid across the cold size and delivers this cold fluid to the applicator device. An optimal flow rate for each pump is controlled and determined to optimize the transfer of heat in the booster. The controller system can adjust and control the pump flow rate. The peltier devices operate via an applied voltage and drawing current from a DC power supply. Setting the applied voltage will set the operating state of the Peltier. Controlling the cold side flow rate and/or the peltier voltages, the Controller can quickly set the temperature at the applicator, cooling or warming as desired to achieve the temperature profiles in FIGS. 25-26. The natural body warming due to blood flow can warm chilled tissue. Or, the peltier devices create heat and slowing the hot side pump flow rate will result in an overall warming of the booster to provide a warming of the applicator.

Figure 33:
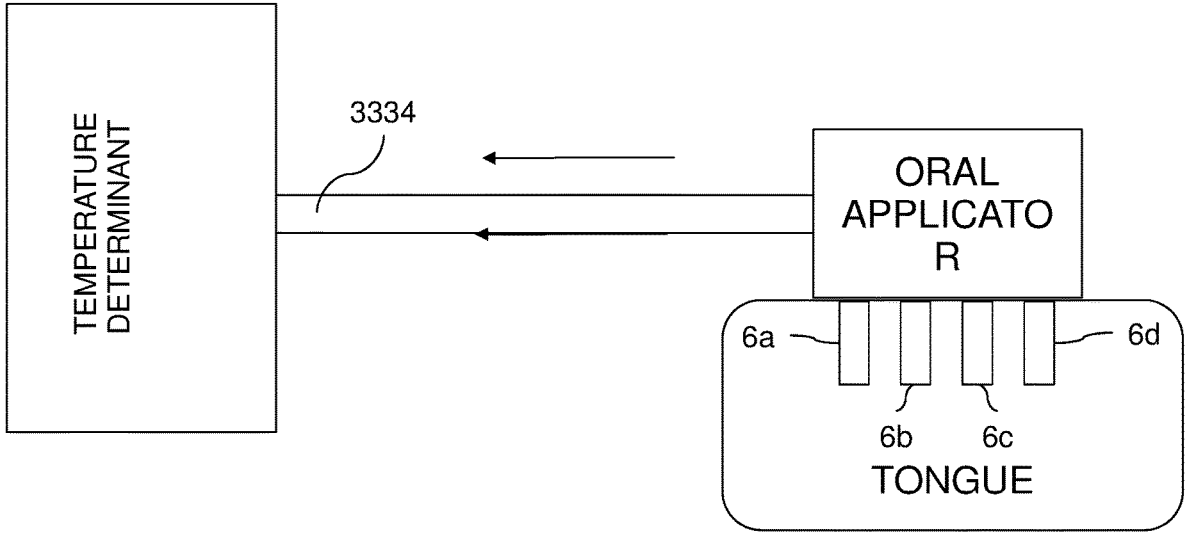
FIG. 33 shows another implementation of a two stage heat extractor with non-isolated secondary circuit.
Figure 34:
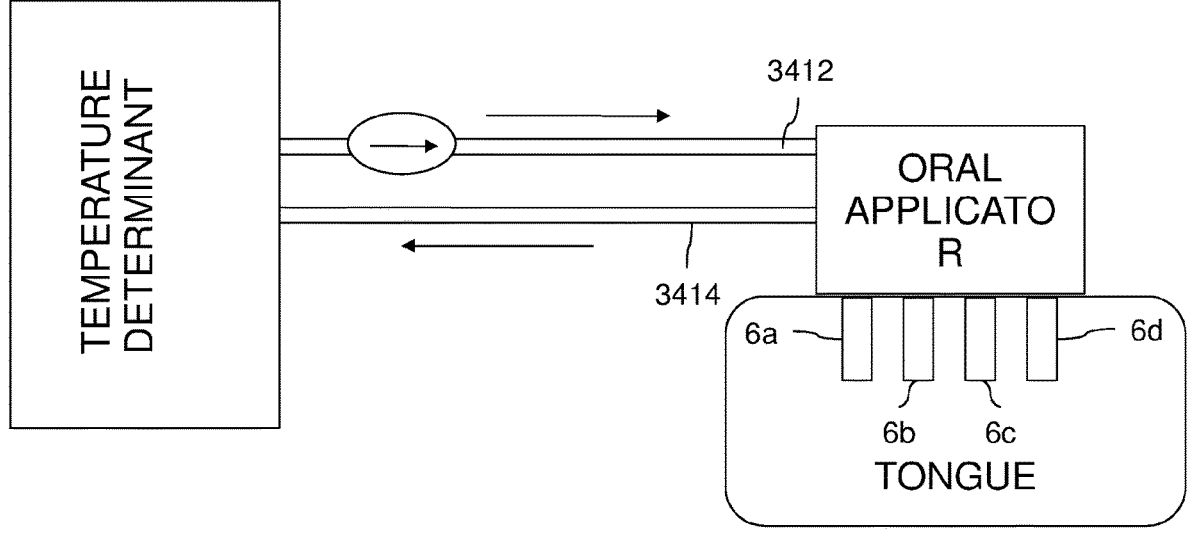
FIG. 34 shows a case where heat transfer between the temperature determinant and the applicator takes place by convective means, i.e., fluid that is flowing between the temperature determinant and the applicator via inlet and outlet lines carries the heat.
Figure 35:
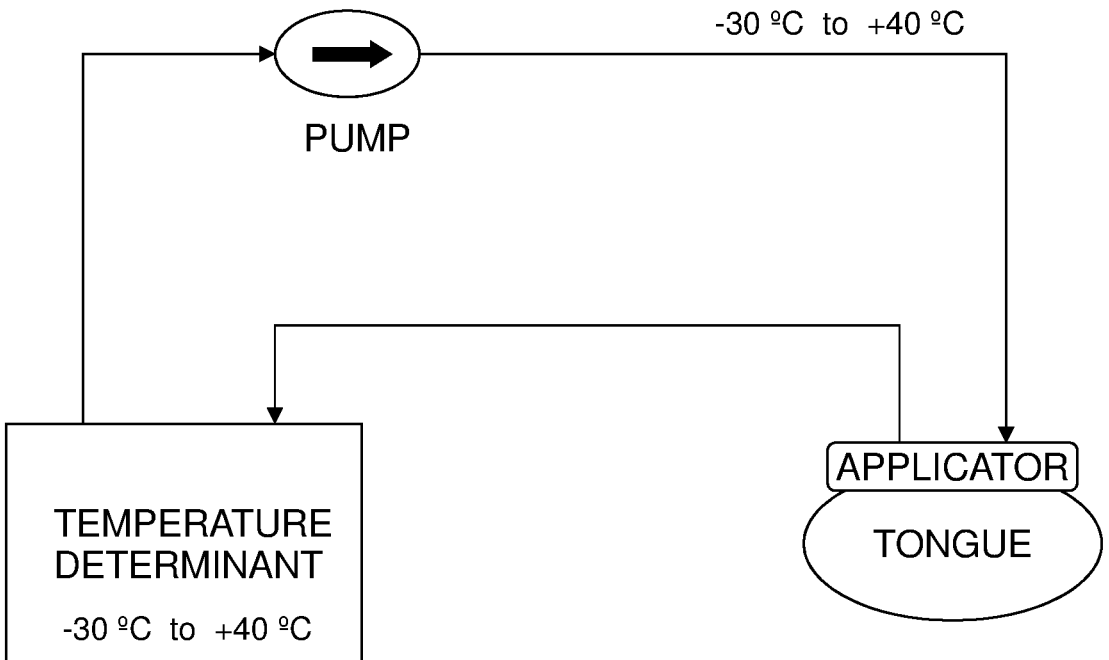
FIG. 35 is a schematic diagram of a system that uses a liquid pump to cause coolant to flow from the temperature determinant to the applicator and vice versa.

Heat transfer between the temperature determinant and the applicator can be accomplished using conductive or convective techniques. FIG. 33 shows an implementation where there is a solid conductor 3334 between the temperature determinant and the applicator, and the heat transfer takes place by conductive means. In this example, any thermally conductive structure, such as a metal rod, would allow the flow of heat from one end to the other. For example, an aluminum rod with length of 10 cm and a cross section of 1 square centimeter could carry 14 Watts of heat when the temperature difference between its end points is 60 C, as would be the case when one end of the rod is in contact with tissue at +37 C and the other end is chilled to –23 C. In this situation, the applicator is cooled only by the conductive flow of the heat through the metal rod with no circulating fluid in and out of the applicator. FIG. 34 however shows a case where heat transfer between the temperature determinant and the applicator takes place by convective means, i.e., fluid that is flowing between the temperature determinant and the applicator via inlet and outlet lines 3412 and 3414 carries the heat. FIG. 35 is a schematic diagram of a system that uses a liquid pump to cause coolant to flow from the temperature determinant to the applicator and vice versa.

Figure 36:
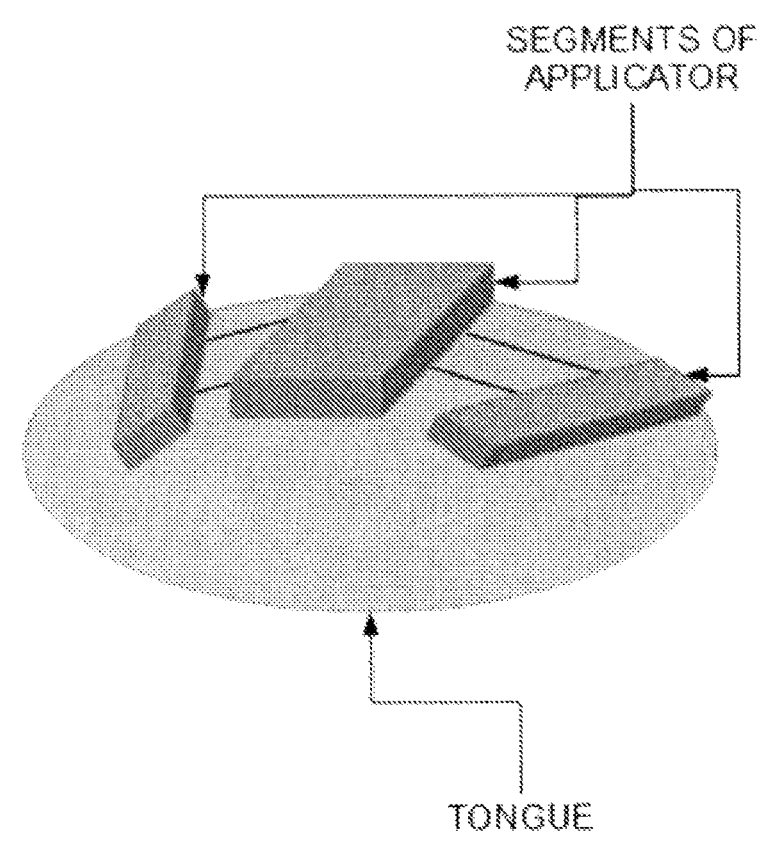
FIG. 36 shows the implementation of the applicator that is designed to have multiple segments for better conformation to tissue surface.

In some examples, the applicator can be constructed to have multiple separate segments that contact the tongue, as shown in FIG. 36. Each of the individual segments can be thermally coupled together with a conductor or fluid conduit. Such a device can be used to conform to the shape of the tissue and allows the medical professionals to use the same device to target different parts of the organ. The applicator can also be designed to keep the different segments at different temperatures, which would allow the temperature profile within the tissue to be altered by making the heat being extracted by each segment different for each segment.

Similarly, heat extraction rates from each segment could be controlled separately such that the temperature of each segment is maintained at the ideal temperature, such as-10C for example. Furthermore, it is possible to construct the segments of the applicator to be rigid or flexible, as would be in the case where the segments of the applicator were constructed using nitinol. Other materials that can be used for the construction of the applicator are metals, plastics and ceramics including glasses.

The controller governs the operation of the entire system and provides a user interface to the operator, which is usually a medical professional. The controller monitors the temperature of the applicator as well as the operation of the heat extractor along with all its stages, including the flow rate of the coolants. The controller can be used to change the slope of the cooling and warming phases of the therapy. Slower cooling can induce ice crystals which induce adipose cell death. A fast warming phase can induce reperfusion injury. As oxygen returns to the tissue damage is impacted to the cell due to inrush of oxygen to the oxygen starved cell. The absence of oxygen and nutrients from blood during the ischemic period creates a condition in which the restoration of circulation results in inflammation and oxidative damage through the induction of oxidative stress, rather than (or along with) restoration of normal function.

The controller of the system may work in open loop or in closed loop configuration. In open loop configuration, the controller can be programmed to follow a given treatment pattern which is defined in terms of temperature or power values for pre-specified durations. For example, the device may be programmed to cool the applicator by delivering fluid at –25° C. for 50 minutes, and then to heat the tissue as quickly as possible by delivering fluid at +37° C. for 10 minutes. In the closed loop configuration, the controller may utilize the data coming from the temperature sensors as feedback and perform more complex tasks. For example, the device may be programmed to keep the surface temperature at –27° C. for 50 minutes, and then warm the tissue by delivering 25 Watts of heat until the surface temperature reaches to +35° C.

Based on its programming, the controller changes the temperature of the applicator and its segments to provide temporal and spatial control of the heat removal from the tissue. These changes could be a preprogrammed sequence or a result of the temperature measurements made by the controller. Temperature measurements can be made from the segments of the applicator and the coolants of the heat extractor.

Another function of the controller is to monitor the usage of the medical device for maintenance and billing purposes. In addition to generating reports on the component life, use period is also reported. These reports can be made available via on board display or internet connectivity. An exemplary design of the controller is shown on FIG. 29.

The controller is fully programmable, so it can operate autonomously to generate the temperature profiles described above. It can also be operated manually, and it allows the operator to override the programming parameters at will, such as switching the temperature determinant from chilling to warming, in the case of an emergency requiring the removal of the applicator quickly from the patient.

An optical electronic camera and/or a port to hold a flexible scope may be provided with the purpose of aiding the physician in placing the probe in the correct location. The visualization of the base of tongue, including the vallecula and epiglottis is very difficult due to the presence of the applicator and, typically, an intubation tube. Placing a very small camera on the applicator and having a video screen show an image of the cephalic (posterior) view during insertion allows the physician to visualize location. A camera in this location also verifies that the epiglottis is not stuck under the applicator or in any unusual positions, which could damage the epiglottis due to mechanical forces or undesired exposure to cryo temperatures. The applicator probe will be insulated on all surfaces except the area desired to be in contact with the tongue. The insulation material could be foam, plastics, or any other suitable insulation that does not conduct heat. Instead of a camera, an alternative is to provide a port to accept and position a flexible ENT scope. This port maintains the position of the scope pointing in the cephalic direction and at an angle adequate to visualize the epiglottis.

In some embodiments of the invention, the applicator is positioned manually using visual clues. In other embodiments, the device is positioned under imaging guidance, such as an ENT scope, ultrasound or X-ray fluoroscopy. Yet in other embodiments, the applicator is positioned using the mechanical guidance provided by other tools, such as a ring sliding over the endotracheal tube.

It is to be understood that although the above description of the applicator is based on its use on tongue tissue, nothing in the description prevents its use on the fat containing tissues including but not limited to the oropharynx, soft palate and the hard palate, the uvula, the lateral pharyngeal wall, or the lingual tonsils. Furthermore, various kinds of applicators, including but not limited to the surface contact type, penetrating type, multi-segment type and balloon type can be designed and used on one or more of the fat containing tissues as listed above.

The various illustrative embodiments of devices, systems, and methods described herein are not intended to be limited to the particular forms disclosed. Rather, they include all modifications and alternatives falling within the scope of the claims.

The various illustrative embodiments of devices, systems, and methods described herein are not intended to be limited to the particular forms disclosed. Rather, they include all modifications and alternatives falling within the scope of the claims. The claims are not intended to include, and should not be interpreted to include, means-plus- or step-plus-function limitations, unless such a limitation is explicitly recited in a given claim using the phrase(s) "means for" or "step for," respectively.

What is claimed is:

1. A device for treatment of obstructive sleep apnea, the device comprising:

a temperature determinant configured to chill and heat a fluid; and an applicator including an inlet line having an inlet tube configured to receive the fluid from the temperature determinant, and an outlet line having an outlet tube configured to remove the fluid from the applicator, the applicator having a tissue contacting surface sized and configured to contact a tongue of a patient, wherein the inlet tube and the outlet tube are vertically aligned and in parallel to one another at a proximal end of the applicator, such that the inlet tube and the outlet tube are each spaced apart from the tissue contacting surface by the same distance, wherein the tissue contacting surface comprises a curvature along an axis extending from a proximal end portion of the tissue contacting surface toward a distal end portion of the tissue contacting surface, the applicator further comprising a hollow cavity including baffles having at least two protrusions extending from a bottom surface of the hollow cavity, wherein the at least two protrusions define at least two distinct flow paths that promote flow of the fluid within the hollow cavity;

the applicator and temperature determinant being configured to cooperatively cause cooling of the tongue for a time sufficient to cause cryolysis of adipose tissue within the tongue and thereby reduce a volume of the adipose tissue.

2. The device of claim 1, wherein the applicator has a width ranging from 1 cm to 5 cm and a length ranging from 1 cm to 8 cm.

3. The device of claim 1, wherein the applicator can be cooled with the fluid as low as −30° C.

4. The device of claim 1, wherein the temperature determinant comprises a liquid cooler and a liquid warmer.

5. The device of claim 4, wherein the temperature determinant further comprises a first valve controllable to cause the fluid to pass through the liquid cooler and a second valve controllable to cause the fluid to pass through the liquid warmer.

6. The device of claim 1, wherein cooling of the tongue is performed for up to 60 minutes.

7. The device of claim 1, wherein the applicator and temperature determinant are configured to cooperatively cause rapid warming of the tongue after cooling the tongue to prevent damage to mucosal layers adjacent to the tongue.

8. The device of claim 7, wherein the rapid warming is performed at a warming rate of higher than 10° C./min.

9. The device of claim 7, wherein the rapid warming is performed at a warming rate of 10° C./min to 30° C./min.

10. The device of claim 1, wherein the baffles are partially circular in shape such that the baffles promote circular flow of the fluid within the hollow cavity.

11. The device of claim 1, wherein the temperature determinant comprises a multi-stage heat extractor.

12. The device of claim 11, wherein the multi-stage heat extractor further comprises a coolant reservoir.

13. The device of claim 1, wherein the inlet line and the outlet line are parallel to one another at an interface that fluidically couples the inlet line and the outlet line to the hollow cavity of the applicator.

14. The device of claim 1, wherein the proximal end portion of the tissue contacting surface has a first radius of curvature along the axis and the distal end portion of the tissue contacting surface has a second radius of curvature along the axis.

15. A device for treatment of obstructive sleep apnea, the device comprising:

a temperature determinant configured to chill and/or heat a fluid;

an inlet line fluidically coupled to the temperature determinant;

an outlet line fluidically coupled to the temperature determinant; and an applicator including (i) an inlet tube configured to be coupled to the inlet line and (ii) an outlet tube configured to be coupled to the outlet line, and (iii) a tissue contacting surface sized to contact a tongue of a patient, wherein:

the inlet tube has a proximal end, and a distal end further from the inlet line than the proximal end of the inlet tube, the outlet tube has a proximal end, and a distal end further from the outlet line than the proximal end of the outlet tube, the distal end of the inlet tube and the distal end of the outlet tube are vertically aligned and in parallel to one another such that the inlet tube and the outlet tube are each spaced apart from the tissue contacting surface by the same distance, and the tissue contacting surface comprises a curvature.

* * * * *